US012697093B2

(12) United States Patent
Staebler et al.

(10) Patent No.: US 12,697,093 B2
(45) Date of Patent: Aug. 4, 2026

(54) ACOUSTIC COUPLANT DEVICES AND INTERFACE MEDIUMS

(71) Applicant: Decision Sciences Medical Company, LLC, Poway, CA (US)

(72) Inventors: Zachary Staebler, Poway, CA (US); Allan Wegner, Poway, CA (US)

(73) Assignee: Decision Sciences Medical Company, LLC, Poway, CA (US)

( * ) Notice: Subject to any disclaimer, the term of this patent is extended or adjusted under 35 U.S.C. 154(b) by 0 days.

(21) Appl. No.: 18/691,792

(22) PCT Filed: Sep. 13, 2022

(86) PCT No.: PCT/US2022/043386
§ 371 (c)(1),
(2) Date: Mar. 13, 2024

(87) PCT Pub. No.: WO2023/039397
PCT Pub. Date: Mar. 16, 2023

(65) Prior Publication Data
US 2024/0382175 A1 Nov. 21, 2024

Related U.S. Application Data

(60) Provisional application No. 63/243,670, filed on Sep. 13, 2021.

(51) Int. Cl.
*A61B 8/00* (2006.01)

(52) U.S. Cl.
CPC .......... *A61B 8/4281* (2013.01); *A61B 8/4488* (2013.01)

(58) Field of Classification Search
CPC ... A61B 8/4281; A61B 8/4488; A61B 8/4236; A61B 8/4272; B06B 3/04; G10K 11/24
See application file for complete search history.

(56) References Cited

U.S. PATENT DOCUMENTS

| | | | |
|---|---|---|---|
| 4,105,018 A | 8/1978 | Greenleaf et al. |
| 4,110,755 A | 8/1978 | Zottl |
| (Continued) | | |

FOREIGN PATENT DOCUMENTS

| | | |
|---|---|---|
| CA | 2427186 | 5/2001 |
| CA | 2852801 | 5/2013 |
| (Continued) | | |

OTHER PUBLICATIONS

Extended European Search Report mailed Jun. 30, 2025 for European Patent Application No. 22868211.8, 9 pages.
(Continued)

*Primary Examiner* — Adil Partap S Virk
(74) *Attorney, Agent, or Firm* — Ashurst Perkins Coie US LLP

(57) ABSTRACT

Devices, systems, and methods are disclosed for use in tomographic ultrasound imaging, large aperture ultrasound imaging and therapeutic ultrasound that provide for coupling acoustic signal transducers to body structures for transmitting and receiving acoustic signals. In some aspects, an acoustic couplant device includes an acoustic coupling component including a sonolucent coupling medium (SCM) material; and a coupling assembly to attach the acoustic coupling component to a housing of an array of transducer elements, the coupling assembly comprising: a bracket having a first portion at least partially embedded within the SCM material of the acoustic coupling component and a second portion at least partially extending out of the acoustic coupling component, and a fastener coupled to at least the second portion of the bracket and configured to attach the second portion of the bracket to the housing.

20 Claims, 20 Drawing Sheets

(56) References Cited

U.S. PATENT DOCUMENTS

| | | | |
|---|---|---|---|
| 4,159,462 A | 6/1979 | Rocha et al. | |
| 4,277,367 A | 7/1981 | Madsen et al. | |
| 4,437,468 A | 3/1984 | Sorenson | |
| 4,463,608 A | 8/1984 | Takeuchi et al. | |
| 4,620,546 A | 11/1986 | Aida et al. | |
| 4,821,206 A | 4/1989 | Arora | |
| 4,830,015 A | 5/1989 | Okazaki | |
| 4,888,746 A | 12/1989 | Wurster et al. | |
| 5,039,774 A * | 8/1991 | Shikinami | C08G 18/12 |
| | | | 600/459 |
| 5,078,149 A | 1/1992 | Katsumata | |
| 5,181,513 A | 1/1993 | Touboul et al. | |
| 5,241,964 A | 9/1993 | McQuilkin | |
| 5,269,309 A | 12/1993 | Fort et al. | |
| 5,284,143 A | 2/1994 | Rattner | |
| 5,329,944 A | 7/1994 | Fabian et al. | |
| 5,394,877 A | 3/1995 | Orr et al. | |
| 5,417,218 A | 5/1995 | Spivey et al. | |
| 5,445,144 A | 8/1995 | Wodicka et al. | |
| 5,465,722 A | 11/1995 | Fort et al. | |
| 5,522,878 A | 6/1996 | Montecalvo | |
| 5,533,510 A | 7/1996 | Koch, III et al. | |
| 5,608,690 A | 3/1997 | Hossack et al. | |
| 5,623,928 A | 4/1997 | Wright et al. | |
| 5,753,095 A | 5/1998 | Alpenfels et al. | |
| 5,793,701 A | 8/1998 | Wright et al. | |
| 5,800,356 A | 9/1998 | Criton et al. | |
| 5,803,089 A | 9/1998 | Ferre et al. | |
| 5,806,518 A | 9/1998 | Mittelstadt | |
| 5,829,444 A | 11/1998 | Ferre et al. | |
| 5,868,676 A | 2/1999 | McCabe et al. | |
| 5,873,830 A | 2/1999 | Hossack et al. | |
| 5,882,557 A | 3/1999 | Hayakawa et al. | |
| 5,902,244 A | 5/1999 | Kobayashi et al. | |
| 5,913,823 A | 6/1999 | Hedberg et al. | |
| 5,967,980 A | 10/1999 | Ferre et al. | |
| 6,016,285 A | 1/2000 | Wright et al. | |
| 6,039,694 A | 3/2000 | Larson | |
| 6,045,507 A | 4/2000 | Muzilla et al. | |
| 6,050,945 A | 4/2000 | Peterson et al. | |
| 6,083,164 A | 7/2000 | Oppelt et al. | |
| 6,106,464 A | 8/2000 | Bass et al. | |
| 6,107,365 A * | 8/2000 | Bertozzi | A61L 27/52 |
| | | | 523/105 |
| 6,110,114 A | 8/2000 | Nock et al. | |
| 6,113,544 A | 9/2000 | Mo | |
| 6,123,669 A | 9/2000 | Kanda | |
| 6,132,375 A | 10/2000 | Napolitano | |
| 6,157,592 A | 12/2000 | Kriz et al. | |
| 6,205,411 B1 | 3/2001 | DiGioia, III et al. | |
| 6,231,834 B1 | 5/2001 | Unger et al. | |
| 6,241,676 B1 | 6/2001 | Savord | |
| 6,322,567 B1 | 11/2001 | Mittelstadt et al. | |
| 6,338,765 B1 | 1/2002 | Statnikov | |
| 6,340,363 B1 | 1/2002 | Bolger et al. | |
| 6,341,231 B1 | 1/2002 | Ferre et al. | |
| 6,402,707 B1 | 6/2002 | Ernst | |
| 6,436,045 B1 | 8/2002 | Rafter et al. | |
| 6,445,943 B1 | 9/2002 | Ferre et al. | |
| 6,508,766 B2 | 1/2003 | Sato et al. | |
| 6,537,216 B1 | 3/2003 | Shifrin | |
| 6,583,392 B2 | 6/2003 | Hershey et al. | |
| 6,585,648 B1 | 7/2003 | Robinson | |
| 6,620,101 B2 | 9/2003 | Azzam et al. | |
| 6,626,916 B1 | 9/2003 | Yeung et al. | |
| 6,652,461 B1 | 11/2003 | Levkovitz et al. | |
| 6,687,531 B1 | 2/2004 | Ferre et al. | |
| 6,725,082 B2 | 4/2004 | Sati et al. | |
| 6,736,780 B2 | 5/2004 | Song et al. | |
| 6,757,582 B2 | 6/2004 | Brisson et al. | |
| 6,785,571 B2 | 8/2004 | Glossop | |
| 6,786,097 B2 | 9/2004 | Song et al. | |
| 6,796,988 B2 | 9/2004 | Melkent et al. | |
| 6,808,494 B2 | 10/2004 | Shifrin | |
| 6,843,957 B2 | 1/2005 | Statnikov | |
| 6,918,877 B2 | 7/2005 | Hossack et al. | |
| 6,934,575 B2 | 8/2005 | Ferre et al. | |
| 6,939,300 B2 | 9/2005 | Petersen et al. | |
| 6,960,173 B2 | 11/2005 | Babaev | |
| 7,004,906 B1 | 2/2006 | Guracar et al. | |
| 7,066,886 B2 * | 6/2006 | Song | G01S 15/8961 |
| | | | 600/443 |
| 7,207,939 B2 | 4/2007 | Husher | |
| 7,226,456 B2 | 6/2007 | O'Neil et al. | |
| 7,291,119 B1 | 11/2007 | de Guise et al. | |
| 7,344,609 B2 | 3/2008 | Statnikov | |
| 7,395,181 B2 | 7/2008 | Foxlin | |
| 7,473,250 B2 | 1/2009 | Makin et al. | |
| 7,532,201 B2 | 5/2009 | Quistgaard et al. | |
| 7,542,790 B2 | 6/2009 | Jensen et al. | |
| 7,566,304 B2 | 7/2009 | Nakamura et al. | |
| 7,678,049 B2 | 3/2010 | Tsoref et al. | |
| 7,719,515 B2 | 5/2010 | Fujiwara et al. | |
| 7,719,689 B2 | 5/2010 | Lee et al. | |
| 7,728,487 B2 | 6/2010 | Adachi et al. | |
| 7,763,035 B2 | 7/2010 | Melkent et al. | |
| 7,798,585 B2 | 9/2010 | Oguri | |
| 7,806,823 B2 | 10/2010 | Sakai et al. | |
| 7,826,889 B2 | 11/2010 | David et al. | |
| 7,835,778 B2 | 11/2010 | Foley et al. | |
| 7,835,784 B2 | 11/2010 | Mire et al. | |
| 7,837,625 B2 | 11/2010 | Abe | |
| RE42,194 E | 3/2011 | Foley et al. | |
| 7,905,836 B2 | 3/2011 | Dan | |
| 7,917,317 B2 | 3/2011 | McKeon | |
| 7,938,777 B2 | 5/2011 | Amiot et al. | |
| 7,938,778 B2 | 5/2011 | Sakai | |
| 7,982,362 B2 | 7/2011 | Adachi et al. | |
| 8,002,705 B1 | 8/2011 | Napolitano et al. | |
| 8,038,616 B2 | 10/2011 | Angelsen et al. | |
| 8,043,220 B2 | 10/2011 | Okada et al. | |
| 8,103,461 B2 | 1/2012 | Glaser et al. | |
| 8,105,339 B2 | 1/2012 | Melkent et al. | |
| 8,126,533 B2 | 2/2012 | Lavallee | |
| 8,147,409 B2 | 4/2012 | Shifrin | |
| 8,152,726 B2 | 4/2012 | Amiot et al. | |
| 8,165,658 B2 | 4/2012 | Waynik et al. | |
| 8,241,217 B2 | 8/2012 | Chiang et al. | |
| 8,251,908 B2 | 8/2012 | Vortman et al. | |
| 8,253,578 B2 | 8/2012 | Watabe et al. | |
| 8,311,611 B2 | 11/2012 | Csavoy et al. | |
| 8,323,200 B2 | 12/2012 | Kunita | |
| 8,372,070 B2 | 2/2013 | Tanaka et al. | |
| 8,374,674 B2 | 2/2013 | Gertner | |
| 8,409,099 B2 | 4/2013 | Vitek et al. | |
| 8,409,103 B2 | 4/2013 | Grunwald et al. | |
| 8,444,564 B2 | 5/2013 | Mahfouz et al. | |
| 8,447,388 B2 | 5/2013 | Igarashi | |
| 8,491,476 B2 | 7/2013 | Iwama et al. | |
| 8,556,834 B2 | 10/2013 | Gertner | |
| 8,565,860 B2 | 10/2013 | Kimchy et al. | |
| 8,626,267 B2 | 1/2014 | Lavallee | |
| 8,675,939 B2 | 3/2014 | Moctezuma de la Barrera | |
| 8,771,188 B2 | 7/2014 | Schers et al. | |
| 8,774,900 B2 | 7/2014 | Buly et al. | |
| 8,814,810 B2 | 8/2014 | Roche et al. | |
| 8,864,686 B2 | 10/2014 | Roche et al. | |
| 8,880,152 B2 | 11/2014 | Lavallee | |
| 8,909,325 B2 | 12/2014 | Kimchy et al. | |
| 8,939,909 B2 | 1/2015 | Wegner | |
| 8,986,609 B2 | 3/2015 | Rau et al. | |
| 9,060,794 B2 | 6/2015 | Kang et al. | |
| 9,101,394 B2 | 8/2015 | Arata et al. | |
| 9,174,065 B2 | 11/2015 | Gertner | |
| 9,196,046 B2 | 11/2015 | Meyer | |
| 9,220,571 B2 | 12/2015 | Lavallee | |
| 9,244,169 B2 | 1/2016 | Fan et al. | |
| 9,248,001 B2 | 2/2016 | Colombet et al. | |
| 9,352,171 B2 | 5/2016 | Gertner | |
| 9,387,276 B2 | 7/2016 | Sun et al. | |
| 9,420,999 B2 | 8/2016 | Wegner | |
| 9,572,548 B2 | 2/2017 | Moctezuma de la Barrera | |
| 9,597,058 B2 | 3/2017 | Kanayama et al. | |
| 9,844,359 B2 | 12/2017 | Gerbaulet et al. | |

(56)  References Cited

U.S. PATENT DOCUMENTS

| | | | |
|---|---|---|---|
| 9,872,667 | B2 | 1/2018 | Wegner |
| 10,085,722 | B2 | 10/2018 | Wegner |
| 10,321,889 | B2 | 6/2019 | Wegner |
| 10,336,896 | B2 | 7/2019 | Zheng et al. |
| 10,426,429 | B2 | 10/2019 | Kruse et al. |
| 10,743,838 | B2 | 8/2020 | Freiburg |
| 10,975,205 | B2 | 4/2021 | Illeperuma et al. |
| 11,154,274 | B2 | 10/2021 | Wegner |
| 11,191,521 | B2 | 12/2021 | Freiburg et al. |
| 11,839,512 | B2 | 12/2023 | Freiburg |
| 2002/0068871 | A1 | 6/2002 | Mendlein et al. |
| 2002/0099290 | A1 | 7/2002 | Haddad |
| 2002/0122536 | A1 | 9/2002 | Kerrien et al. |
| 2002/0188198 | A1* | 12/2002 | Hong .................... A61B 8/4494 |
| | | | 600/437 |
| 2002/0188229 | A1 | 12/2002 | Ryaby et al. |
| 2003/0036702 | A1 | 2/2003 | Davidsen |
| 2003/0125628 | A1* | 7/2003 | Song ................... G01S 15/8961 |
| | | | 600/447 |
| 2003/0233045 | A1 | 12/2003 | Vaezy |
| 2004/0066708 | A1 | 4/2004 | Ogawa |
| 2004/0236223 | A1 | 11/2004 | Barnes et al. |
| 2005/0101861 | A1 | 5/2005 | Satoh |
| 2005/0101867 | A1* | 5/2005 | Johnson ............. G01S 15/8915 |
| | | | 600/459 |
| 2005/0113698 | A1 | 5/2005 | Kristoffersen |
| 2005/0203399 | A1 | 9/2005 | Vaezy |
| 2005/0215893 | A1 | 9/2005 | Barnes et al. |
| 2006/0004290 | A1 | 1/2006 | Smith et al. |
| 2006/0119223 | A1 | 6/2006 | Ossman |
| 2006/0173305 | A1 | 8/2006 | Asafusa et al. |
| 2007/0066897 | A1 | 3/2007 | Sekins et al. |
| 2007/0156050 | A1 | 7/2007 | Barnes et al. |
| 2007/0226975 | A1* | 10/2007 | Takeuchi ............. H10N 30/501 |
| | | | 29/25.35 |
| 2007/0226976 | A1 | 10/2007 | Zipparo et al. |
| 2007/0239001 | A1 | 10/2007 | Mehi et al. |
| 2007/0239002 | A1 | 10/2007 | Alam |
| 2007/0265690 | A1 | 11/2007 | Lichtenstein et al. |
| 2007/0276238 | A1 | 11/2007 | Sudol |
| 2008/0051655 | A1 | 2/2008 | Sato |
| 2008/0110263 | A1* | 5/2008 | Klessel ................ A61B 8/4483 |
| | | | 310/322 |
| 2008/0119737 | A1 | 5/2008 | Urbano et al. |
| 2008/0200810 | A1 | 8/2008 | Buchalter |
| 2008/0208055 | A1 | 8/2008 | Bertram et al. |
| 2008/0281202 | A1 | 11/2008 | Fraser et al. |
| 2008/0281237 | A1 | 11/2008 | Slayton et al. |
| 2009/0043206 | A1* | 2/2009 | Towfiq ................... A61B 8/483 |
| | | | 600/447 |
| 2009/0093737 | A1 | 4/2009 | Gerbaulet et al. |
| 2009/0124871 | A1 | 5/2009 | Arshak et al. |
| 2009/0306497 | A1 | 12/2009 | Manzke et al. |
| 2010/0029789 | A1 | 2/2010 | Chen |
| 2010/0179425 | A1 | 7/2010 | Zadicario |
| 2010/0204577 | A1 | 8/2010 | Sekins et al. |
| 2010/0268072 | A1 | 10/2010 | Hall et al. |
| 2010/0274139 | A1 | 10/2010 | Fukukita et al. |
| 2010/0280379 | A1 | 11/2010 | Satoh |
| 2010/0286518 | A1 | 11/2010 | Lee et al. |
| 2010/0286527 | A1* | 11/2010 | Cannon .................... A61B 8/42 |
| | | | 600/459 |
| 2011/0008437 | A1 | 1/2011 | Altman et al. |
| 2011/0092862 | A1 | 4/2011 | Chivers |
| 2011/0264012 | A1 | 10/2011 | Lautzenhiser et al. |
| 2012/0029345 | A1 | 2/2012 | Mahfouz et al. |
| 2012/0087564 | A1 | 4/2012 | Tsujita |
| 2012/0238875 | A1 | 9/2012 | Savitsky et al. |
| 2012/0253071 | A1 | 10/2012 | Rau et al. |
| 2012/0281507 | A1* | 11/2012 | Rikoski ................... G01S 15/89 |
| | | | 367/88 |
| 2013/0060121 | A1 | 3/2013 | Patwardhan et al. |
| 2013/0102875 | A1 | 4/2013 | Dogra et al. |
| 2013/0123635 | A1* | 5/2013 | Wegner ................ A61B 8/4483 |
| | | | 600/447 |
| 2013/0144135 | A1 | 6/2013 | Mahfouz et al. |
| 2013/0144166 | A1 | 6/2013 | Specht et al. |
| 2013/0150863 | A1 | 6/2013 | Baumgartner |
| 2013/0165005 | A1 | 6/2013 | Berard-Anderson et al. |
| 2013/0218013 | A1 | 8/2013 | Barthe et al. |
| 2013/0338503 | A1 | 12/2013 | Cohen |
| 2014/0163377 | A1 | 6/2014 | Kang et al. |
| 2014/0163382 | A1 | 6/2014 | Gubbini et al. |
| 2014/0180116 | A1 | 6/2014 | Lindekugel et al. |
| 2014/0353248 | A1 | 12/2014 | Kuraray |
| 2015/0018682 | A1 | 1/2015 | Schers et al. |
| 2015/0038613 | A1 | 2/2015 | Sun et al. |
| 2015/0080725 | A1 | 3/2015 | Wegner |
| 2015/0088040 | A1 | 3/2015 | Barthe et al. |
| 2015/0133788 | A1 | 5/2015 | Mauldin, Jr. et al. |
| 2015/0141827 | A1* | 5/2015 | Kiyose ................ A61B 8/4483 |
| | | | 29/25.35 |
| 2015/0164467 | A1 | 6/2015 | Suetoshi et al. |
| 2015/0182191 | A1 | 7/2015 | Caluser et al. |
| 2015/0274805 | A1 | 10/2015 | Annabi et al. |
| 2015/0313572 | A1 | 11/2015 | Gerbaulet et al. |
| 2016/0000409 | A1 | 1/2016 | Bruder et al. |
| 2016/0083574 | A1 | 3/2016 | Zheng et al. |
| 2016/0100821 | A1 | 4/2016 | Eggers et al. |
| 2016/0176128 | A1 | 6/2016 | Zhao et al. |
| 2016/0242736 | A1* | 8/2016 | Freiburg ............ G01S 7/52079 |
| 2016/0270763 | A1 | 9/2016 | Hayes et al. |
| 2016/0354520 | A1 | 12/2016 | Sun et al. |
| 2017/0100092 | A1 | 4/2017 | Kruse et al. |
| 2017/0368333 | A1 | 12/2017 | Loudin et al. |
| 2018/0126677 | A1 | 5/2018 | Zhao et al. |
| 2018/0240366 | A1 | 8/2018 | Felsinger et al. |
| 2018/0244858 | A1* | 8/2018 | Illeperuma ............... C08K 3/22 |
| 2019/0070826 | A1 | 3/2019 | Zhao et al. |
| 2019/0167234 | A1 | 6/2019 | Wegner |
| 2020/0138409 | A1 | 5/2020 | Lindekugel et al. |
| 2020/0187900 | A1* | 6/2020 | Seitel ................... A61B 8/4209 |
| 2020/0337674 | A1* | 10/2020 | Wegner ................ A61K 49/226 |
| 2021/0361259 | A1 | 11/2021 | Wegner |
| 2022/0106424 | A1 | 4/2022 | Staebler |
| 2022/0134608 | A1 | 5/2022 | Staebler |
| 2024/0358349 | A1 | 10/2024 | Freiburg et al. |
| 2025/0144853 | A1 | 5/2025 | Staebler |
| 2025/0359559 | A1* | 11/2025 | Carbone ............. A61B 8/4455 |

FOREIGN PATENT DOCUMENTS

| | | |
|---|---|---|
| CN | 100354651 | 12/2007 |
| CN | 101325913 | 12/2008 |
| CN | 102686245 | 9/2012 |
| CN | 102258399 | 11/2012 |
| CN | 104169739 | 11/2014 |
| CN | 104311841 | 1/2015 |
| CN | 105778125 | 7/2016 |
| CN | 107635470 | 1/2018 |
| EP | 0120410 | 11/1989 |
| EP | 0420758 | 4/1991 |
| EP | 952461 | 10/1999 |
| EP | 1707124 | 4/2006 |
| EP | 1795917 | 6/2007 |
| EP | 1854406 | 11/2007 |
| EP | 1955668 | 8/2008 |
| EP | 2033579 | 3/2009 |
| GB | 2379392 | 3/2003 |
| GB | 2472066 | 1/2011 |
| IL | 232148 | 7/2019 |
| JP | 55051351 | 4/1980 |
| JP | 58195550 | 11/1983 |
| JP | 60048736 | 3/1985 |
| JP | 62117535 | 5/1987 |
| JP | H03114453 | 5/1991 |
| JP | 8038473 | 2/1996 |
| JP | 2000041980 | 2/2000 |
| JP | 2000166922 | 6/2000 |
| JP | 2000287988 | 10/2000 |
| JP | 2001515924 | 9/2001 |
| JP | 2003190157 | 7/2003 |

(56) References Cited

FOREIGN PATENT DOCUMENTS

| JP | 2004147852 | 5/2004 |
|----|------------|--------|
| JP | 2005152608 | 6/2005 |
| JP | 2005527336 | 9/2005 |
| JP | 2010082425 | 4/2010 |
| JP | 2011062531 | 3/2011 |
| JP | 2011177461 | 9/2011 |
| JP | 2012002586 | 1/2012 |
| JP | 2013056156 | 3/2013 |
| JP | 2018506416 | 3/2018 |
| WO | 2002024094 | 3/2002 |
| WO | 2007023477 | 3/2007 |
| WO | 2007069156 | 6/2007 |
| WO | 2009009064 | 1/2009 |
| WO | 2009020617 | 2/2009 |
| WO | 2009063421 | 5/2009 |
| WO | 2013066821 | 5/2013 |
| WO | 2013103956 | 7/2013 |
| WO | 2014128593 | 8/2014 |
| WO | 2014150780 | 9/2014 |
| WO | 2014150961 | 9/2014 |
| WO | 2014186904 | 11/2014 |
| WO | 2015038554 | 3/2015 |
| WO | 2016044830 | 3/2016 |
| WO | 2016138257 | 9/2016 |
| WO | 2016149427 | 9/2016 |
| WO | 2017164902 | 9/2017 |
| WO | 2020168087 | 8/2020 |
| WO | 2020181213 | 9/2020 |

OTHER PUBLICATIONS

Notice of Requisition mailed Aug. 20, 2024 in Canadian Patent Application No. 2,977,975, 4 pages.

Second Office Action mailed Dec. 20, 2024 in Chinese Patent Application No. 202080018988.8, 14 pages, English translation.

Australian Exam Report mailed Nov. 1, 2019 for Australian Application No. 2016233279, filed on Mar. 16, 2016 (3 pages).

Australian Exam Report mailed Oct. 18, 2019 for Australian Application No. 2016222637, filed on Feb. 25, 2016 (3 pages).

Callow, H.J., "Signal Processing for Synthetic Aperture Sonar Image Enhancement," Thesis for Ph.D. in Electrical and Electronic Engineering at the University of Canterbury, Christchurch, New Zealand, 273 pages, Apr. 2003.

Cao, Z. et al., "Fabrication and properties of thermosensitive organic/inorganic hybrid hydrogel thin films," Langmuir, American Chemical Society, vol. 24, No. 10, May 20, 2008, pp. 5543-5551.

Chiao, R., "Coded Excitation for Diagnostic Ultrasound: A System Developer's Perspective," IEEE Transactions on Ultrasonics, Ferroelectrics, and Frequency Control, 52(2):160-170, Feb. 2005.

Choe, J.W., et al., "Volumetric real-time imaging using a CMUT ring array," IEEE Transactions on Ultrasonics, Ferroelectrics, and Frequency Control, 59(6):1201-1211, Jun. 2012.

Demi, L., et al., "In Vitro and In Vivo Tissue Harmonic Images Obtained With Parallel Transmit Beamforming by Means of Orthogonal Frequency Division Multiplexing," IEEE Transactions on Ultrasonics, Ferroelectrics, and Frequency Control, 62(1):230-235, Jan. 2015.

European Search Report mailed Oct. 26, 2022 in European Patent Application No. 20767211.4, 13 pages.

European Search Report mailed on Apr. 19, 2017 for European Application No. 14844538.0, filed on Sep. 9, 2014 (10 pages).

European Search Report mailed on Feb. 1, 2019 for European Application No. 16756353.5, filed on Feb. 25, 2016 (14 pages).

European Search Report mailed on Jun. 29, 2015 for European Application No. 12845256.2, filed on Oct. 29, 2012 (8 pages).

European Search Report mailed on Nov. 9, 2018 for European Application No. 16765701.4, filed on Mar. 16, 2016 (6 pages).

European Search Report mailed on Oct. 17, 2022 in European Patent Application No. 20756147.3, 6 pages.

Extended European Search Report mailed Jan. 26, 2023 for European Patent Application No. 20767211.4, 11 pages.

Extended European Search Report mailed on Feb. 15, 2019 for European Application No. 16765701.4, filed on Mar. 16, 2016 (14 pages).

Extended European Search Report mailed on Jul. 2, 2019 for European Application No. 16756353.5, filed on Feb. 25, 2016 (14 pages).

Extended Search Report mailed on Jun. 18, 2019 for European Application No. 16854507.7, filed on Oct. 7, 2016 (11 pages).

Hunter, A.J., et al., "A Comparison of Fast Factorised Back-Projection and Wavenumber Algorithms for SAS Image Reconstruction," Proceedings of the World Congress on Ultrasonics, 4 pages, (2003).

International Search Report and Written Opinion mailed Jul. 16, 2020 for International App. PCT/US20/29564 filed Apr. 23, 2020, 11 pages.

International Search Report and Written Opinion mailed on Dec. 29, 2016 for International Application No. PCT/US2016/056159, filed on Oct. 7, 2016 (7 pages).

International Search Report and Written Opinion mailed on Feb. 7, 2023 for International Application No. PCT/US22/43386, filed on Sep. 13, 2022, 14 pages.

International Search Report and Written Opinion mailed on Jul. 2, 2020 for International Application No. PCT/US2020/021456, filed on Mar. 6, 2020, 16 pages.

International Search Report and Written Opinion mailed on Jul. 6, 2016 for International Application No. PCT/US2016/019554, filed on Feb. 25, 2016 (12 pages).

International Search Report and Written Opinion mailed on Mar. 3, 2015 for International Application No. PCT/US2014/054855, filed on Sep. 9, 2014 (11 pages).

International Search Report and Written Opinion mailed on May 15, 2013 for International Application No. PCT/US2012/062435, filed on Oct. 29, 2012 (9 pages).

International Search Report and Written Opinion mailed on May 18, 2020 for International Application No. PCT/US20/18123, filed on Feb. 13, 2020 (11 pages).

Ito, T., et al., "Evaluation of Acoustic Imaging System Using Correlation Division in Synthetic Transmit Aperture with Multicarrier Signals," IEICE Transactions on Fundamentals of Electronics, Communications and Computer Sciences, E94-A(10):1907-1919, Oct. 2011.

Jensen, J.A., et al., "Synthetic Aperture Ultrasound Imaging," Ultrasonics, 44(Suppl 1):e5-e15, Dec. 2006.

Koch, A., et al., "An Ultrasound Tomography System With Polyvinyl Alcohol (PVA) Moldings for Coupling: In Vivo Results for 3-D Pulse-Echo Imaging of the Female Breast," IEEE Transactions on Ultrasonics, Ferroelectrics, and Frequency Control, 62(2):266-279, Feb. 2015.

Kundur, D., et al., "A Novel Blind Deconvolution Scheme for Image Restoration Using Recursive Filtering," IEEE Transactions on Signal Processing, 46(2):375-390, Feb. 1998.

Laferriere et al. "Syntheses of Water-Soluble Polyacrylamide-Containing Sialic Acid." Methods in Enzymology, vol. 242, 1994, 10 pages.

Low, Z.W. et al., "The role of hydrogen bonding in alginate/poly(acrylamide-co-dimethylacrylamide) and alginate/poly(ethylene glycol) methyl ether methacrylate-based tough hybrid hydrogels." Royal Society of Chemistry, 2015, 5, 8 pages.

Low, Z.W. et al., Supporting Information. "The role of hydrogen bonding in alginate/poly(acrylamide-co-dimethylacrylamide) and alginate/poly(ethylene glycol) methyl ether methacrylate-based tough hybrid hydrogels." Royal Society of Chemistry, 2015, 5, 5 pages.

Misaridis, T., "Use of Modulated Excitation Signals in Medical Ultrasound. Part I: Basic Concepts and Expected Benefits," IEEE Transactions on Ultrasonics, Ferroelectrics, and Frequency Control, 52(2):177-191, Feb. 2005.

Misaridis, T., "Use of Modulated Excitation Signals in Medical Ultrasound. Part II: Design and Performance for Medical Imaging Applications," IEEE Transactions on Ultrasonics, Ferroelectrics, and Frequency Control, 52(2):192-207, Feb. 2005.

(56)                    References Cited

OTHER PUBLICATIONS

Misaridis, T., "Use of Modulated Excitation Signals in Medical Ultrasound. Part III: High Frame Rate Imaging," IEEE Transactions on Ultrasonics, Ferroelectrics, and Frequency Control, 52(2):208-219, Feb. 2005.

Notice of Reasons for Rejection mailed Sep. 26, 2023 in Japanese Patent Application No. 2021-552570, English Translation, 4 pages.

Notice of Requisition mailed Mar. 10, 2023 in Canadian Patent Application No. 2,977,975, 4 pages.

Notice of Requisition mailed Nov. 24, 2023 in Canadian Patent Application No. 2,977,975, 4 pages.

O'Donnell, M., "Coded Excitation for Synthetic Aperture Ultrasound Imaging," *IEEE Transactions on Ultrasonics, Ferroelectrics, and Frequency Control*, 52(2):171-176, Feb. 2005.

Office Action mailed Feb. 23, 2023 in Korean Patent Application No. 2017-7027091, 11 pages, with English Translation.

Office Action mailed Jan. 14, 2020 for Japanese Application No. 2017-563504, filed on Feb. 25, 2016 (14 pages).

Office Action mailed Jul. 12, 2022 in Chinese Patent Application No. 202080021490.7, with English translation, 18 pages.

Office Action mailed Jul. 28, 2022 in Korean Patent Application No. 2017-7027091, machine translation obtained from USPTO Global Dossier at <https://globaldossier.uspto.gov/#/>, 28 pages.

Office Action mailed Jun. 4, 2019 for Japanese Application No. 2017-187288, filed on Oct. 29, 2012 (3 pages).

Office Action mailed Mar. 29, 2024 in Chinese Patent Application No. 202080018988.8, 14 pages, English translation.

Office Action mailed Nov. 7, 2023 in Japanese Patent Application No. 2021-547164, 11 pages, with English translation.

Office Action mailed Oct. 29, 2019 for Japanese Application No. 2018-145683, filed on Sep. 9, 2014 (3 pages).

Office Action mailed Oct. 7, 2021 in Israel Patent Application No. 254158, 6 pages, with English translation.

Office Action mailed on Dec. 4, 2019 for Chinese Application No. 201680023999.9, filed on Feb. 25, 2016 (23 pages).

Office Action mailed on Jul. 3, 2018 for Japanese Application No. 2017-187288, filed on Oct. 29, 2012 (6 pages).

Office Action mailed on Sep. 13, 2016 for Japanese Application No. 2014-539114, filed on Oct. 29, 2012 (4 pages).

Office Action mailed on Sep. 19, 2017 for Japanese Application No. 2016-542050, filed on Sep. 9, 2014 (15 pages).

Office Action mailed on Sep. 2, 2015 for Chinese Application No. 201280065031.4, filed on Oct. 29, 2012 (26 pages).

Office Action mailed Sep. 23, 2020 in Israel Patent Application No. 254158, 3 pages.

Prokop A F et al., "Polyacrylamide gel as an acoustic coupling medium for focused ultrasound therapy." Ultrasound in Medicine and Biol, New York, NY, US, vol. 29, No. 9, Sep. 1, 2003, pp. 1351-1358.

Rui Silva, S., et al., "2 Synthetic Aperture Techniques for Sonar Systems," Advances in Sonar Technology, edited by Sergio Rui Silva, publisher I-Tech Education and Publishing, ISBN 978-3-902613-48-6, pp. 15-42, Feb. 2009.

Second Office Action issued Jul. 14, 2020 for Chinese Patent Application No. 201680023999.9 (41 pages).

Second Office Action mailed Jan. 3, 2023 in Chinese Patent Application No. 202080021490.7, English translation, 16 pages.

Singapore Exam Report mailed on Feb. 26, 2019 for Singapore Application No. 11201706953Y, filed on Feb. 25, 2016 (6 pages).

Singapore Search Report mailed on Sep. 24, 2018 for Singapore Application No. 11201706953Y, filed on Feb. 25, 2016 (13 pages).

Singapore Written Opinion mailed on Jul. 10, 2017 for Singapore Application No. 11201601906P, filed on Sep. 9, 2014 (8 pages).

Singapore Written Opinion mailed on Jun. 21, 2018 for Singapore Application No. 11201707641P, filed on Mar. 16, 2016 (8 pages).

Sun, J.Y. et al., "Highly stretchable and tough hydrogels," Nature, vol. 489, Sep. 6, 2012, 21 pages.

Third Office Action mailed Jul. 10, 2023 in Chinese Patent Application No. 202080021490.7, English translation, 14 pages.

Trots, I. et al., "Synthetic Aperture Method in Ultrasound Imaging," Chapter 3 of Ultrasound Imaging, edited by Masayuki Tanabe, 2011, pp. 37-56.

Zhu, S., et al., "SAS Autofocus Based on Phase Gradient Autofocus," IEEE 2011 Fourth International Workshop on Chaos-Fractals Theories and Applications (IWCFTA), pp. 298-301, Oct. 19-22, 2011.

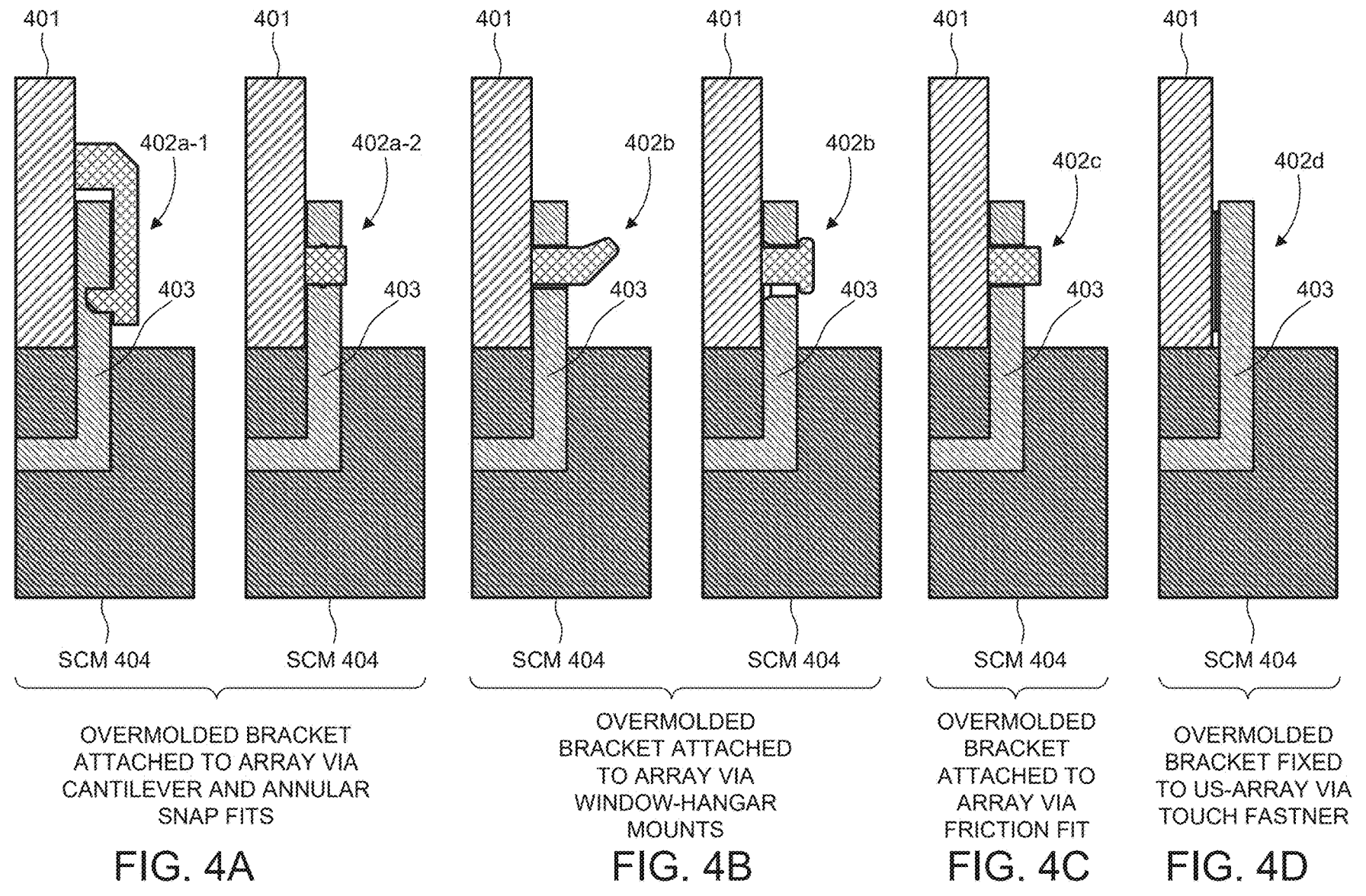

* cited by examiner 401
402d
403
SCM 404

OVERMOLDED
BRACKET FIXED
TO US-ARRAY VIA
TOUCH FASTNER

FIG. 4D 401
402c
403
SCM 404

OVERMOLDED
BRACKET
ATTACHED TO
ARRAY VIA
FRICTION FIT

FIG. 4C 401
402b
403
SCM 404

401
402b
403
SCM 404

OVERMOLDED
BRACKET ATTACHED
TO ARRAY VIA
WINDOW-HANGAR
MOUNTS

FIG. 4B 401
402a-2
403
SCM 404

401
402a-1
403
SCM 404

OVERMOLDED BRACKET
ATTACHED TO ARRAY VIA
CANTILEVER AND ANNULAR
SNAP FITS

FIG. 4A

Top View

Top View

Side View

ACOUSTIC COUPLANT DEVICES AND INTERFACE MEDIUMS

CROSS-REFERENCE TO RELATED APPLICATIONS

This patent document is a National Phase of International Patent Application No. PCT/US22/43386, titled "ACOUSTIC COUPLANT DEVICES AND INTERFACE MEDIUMS" and filed on Sep. 13, 2022, which claims priorities to and benefits of U.S. Provisional Patent Application No. 63/243,670, titled "ACOUSTIC COUPLANT DEVICES AND INTERFACE MEDIUMS" and filed on Sep. 13, 2021. The entire contents of the aforementioned patent applications are incorporated by reference as part of the disclosure of this patent document.

TECHNICAL FIELD

This patent document relates to systems, devices, and processes for acoustic energy diagnostics and therapies.

BACKGROUND

Acoustic imaging is an imaging modality that employs the properties of sound waves traveling through a medium to render a visual image. High frequency acoustic imaging has been used as an imaging modality for decades in a variety of biomedical fields to view internal structures and functions of animals and humans. High frequency acoustic waves used in biomedical imaging may operate in different frequencies, e.g., between 1 and 20 MHz, or even higher frequencies, and are often termed ultrasound waves. Some factors, including inadequate spatial resolution and tissue differentiation, can lead to less than desirable image quality using conventional techniques of ultrasound imaging, which can limit its use for many clinical indications or applications.

SUMMARY

Techniques, systems, and devices are disclosed for coupling acoustic signal transducers to body structures for transmitting and receiving acoustic signals in ultrasound imaging, range-Doppler measurements, and therapies.

In some aspects, a couplant device of the disclosed technology for transmission of acoustic energy between transducers and a target includes a housing body structured to present an array of transducer elements on a flat or curved section (e.g., curved lip) of the housing body (e.g., such as a semicircular or a circular portion that exposes the transducer elements of the array on a curved surface); and an acoustic coupling component including sonolucent coupling medium (SCM), e.g., a hydrogel material, which may be at least partially contained in an outer lining. The acoustic coupling component is operable to conduct acoustic signals between a transducer element disposed in the housing body and a receiving medium (e.g., skin of a subject) in contact with the acoustic coupling component to propagate the acoustic signal toward a target volume, such that the acoustic coupling component is capable to conform to the target volume such that there is an acoustic impedance matching (e.g., very low attenuation) between the receiving medium and the transducer element. For example, the target volume includes a biological structure of a subject (e.g., an organ or tissue), and the receiving medium can include skin of the subject. In implementations of the couplant device, for example, the receiving medium can include hair on the exterior of the skin.

In some aspects, an acoustic couplant device includes an array of transducer elements arranged in a housing and operable to transmit acoustic signals toward a target volume and to receive returned acoustic signals that return from at least part of the target volume; a housing body including a curved section on which the array of transducer elements are arranged; an acoustic coupling component coupled to the array of transducer elements and including a sonolucent coupling medium (SCM) material, the acoustic coupling component operable to conduct the acoustic signals between each transducer element coupled to the acoustic coupling component and a receiving medium when in contact with the acoustic coupling component to propagate the acoustic signals toward the target volume; and a coupling element attached to one of the acoustic coupling component or the housing of the array of transducer elements and attachable to the other of the acoustic coupling component or the housing to secure the acoustic coupling component to the array of transducer elements.

In some aspects, an acoustic couplant device includes an acoustic coupling component including a sonolucent coupling medium (SCM) material, the acoustic coupling component operable to conform to one or more transducer elements of an array of transducer elements and conduct acoustic signals between the one or more transducer elements and a receiving medium when the acoustic coupling component is in contact with the receiving medium to propagate the acoustic signals toward a target volume; and a coupling assembly to attach the acoustic coupling component to a housing of the array of transducer elements, the coupling assembly comprising: a bracket having a first portion at least partially embedded within the SCM material of the acoustic coupling component and a second portion at least partially extending out of the acoustic coupling component, and a fastener coupled to at least the second portion of the bracket and configured to attach the second portion of the bracket to the housing.

The subject matter described in this patent document can be implemented in specific ways that provide one or more of the following features.

BRIEF DESCRIPTION OF THE DRAWINGS

FIGS. 4A-4D show a schematic diagram of exemplary embodiments of fasteners for coupling an exemplary SCM to an ultrasound (US) array of the disclosed technology.

DETAILED DESCRIPTION

Figure 1:
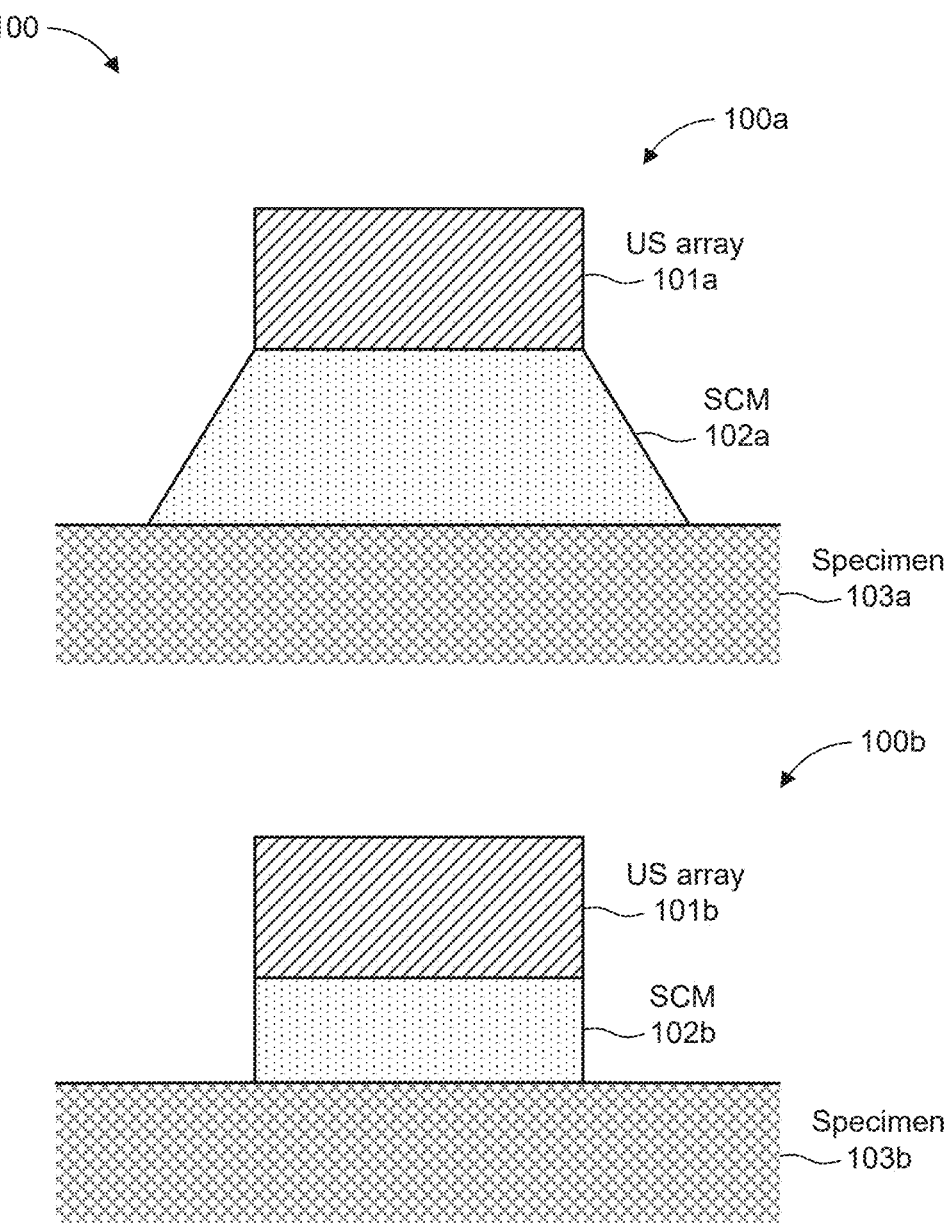
FIG. 1 shows a schematic diagram of exemplary embodiments and exemplary methods of manufacturing a sonolucent coupling medium (SCM) of disclosed technology.

Acoustic imaging can be performed by emitting an acoustic waveform (e.g., pulse) within a physical elastic medium, such as a biological medium, including tissue. The acoustic waveform is transmitted from a transducer element (e.g., of an array of transducer elements) toward a target volume of interest (VOI). A transducer element is a single individual component of the transduction of acoustic and electrical signals, which may be one part of an array of multiple transducer elements (components of the transduction). Propagation of the acoustic waveform in the medium toward the target volume can encounter structures that cause the acoustic waveform to become partly reflected from a boundary between two mediums (e.g., differing biological tissue structures) and partially transmitted. The reflection of the transmitted acoustic waveform can depend on the acoustic impedance difference between the two mediums (e.g., at the interface between two different biological tissue types). For example, some of the acoustic energy of the transmitted acoustic waveform can be scattered back to the transducer at the interface to be received, and processed to extract information, while the remainder may travel on and to the next medium. In some instances, scattering of the reflection may occur as the result of two or more impedances contained in the reflective medium acting as a scattering center. Additionally, for example, the acoustic energy can be refracted, diffracted, delayed, and/or attenuated based on the properties of the medium and/or the nature of the acoustic wave.

To achieve coupling between a non-linear, rigid or flexible acoustic transducer (e.g., Ultrasound (US)) array and a specimen of asymmetric, non-linear topography, a conformable and sonolucent coupling medium (SCM) can be used to efficiently transmit and receive US waves. A SCM has an acoustic impedance in-between the transducer matching layer, or transducer surface, and the specimen-SCM interface to transmit and receive US waves without the bulk of the US wave refracting away from the intended target. Hence, the speed of sound and density of the SCM is tailored to match the acoustic properties of the heterogeneous specimen, and the attenuation of the SCM is minimized in order to maximize the amount of acoustic energy transmitted and received. Since SCMs can be used in a medical setting, where sanitary instrumentation is important, the SCMs should be removable from the US array to sanitize or sterilize the US array before another examination. The SCM, therefore, is not permanently fixed to the array.

A plethora of methods can be used to couple a SCM to an acoustic transducer array (e.g., ultrasound transducers in an array, also referred to herein as "US array"); however, there are certain SCM design constraints and criteria for these methods. For example, the method used to couple the SCM should not interfere or impede with US transmission and US reception. This region, where the transducers can steer the US beam without obstruction, is called the US window. In addition, the method to couple the US array to the SCM should be robust for a variety of US arrays and SCM geometries to prevent the SCM from peeling off the surface of the US array. Methods to couple the US array to the SCM can include compressing the SCM against the array surface or adhere the SCM to the array surface. SCMs should be easy to install and be removable from the US array to encourage the operator to properly sanitize the US array before the next examination; thus, making the installation "quick and easy" lessens the risk of cross contamination. Finally, the SCM should be ergonomic. Cumbersome, floppy, awkward, and heavy SCMs can off-balance the US array, making the US examinations arduous and uncomfortable for both the patient and operator.

Disclosed are techniques, systems, devices, and articles for coupling acoustic signal transducers to a receiving body for transmitting and receiving acoustic signals in acoustic (e.g., ultrasound) imaging, range-Doppler measurements, and therapies. The disclosed acoustic signal transmission couplants can conform to the receiving body or medium (e.g., skin) of a subject such that there is an acoustic impedance matching between the receiving medium and the transducer.

Disclosed are various embodiments of an acoustic coupling medium including a sonolucent coupling medium (SCM) (e.g., a hydrogel formed from one or more polymerizable materials, a ballistic gel, a paraffin gel, or other) and capable of conforming or molding into specific three-dimensional shapes for use in tomographic ultrasound imaging, large aperture ultrasound imaging, and therapeutic ultrasound. Herein, the acoustic coupling medium is also referred to as an "acoustic signal transmission couplant" (or, simply, "acoustic couplant"), "acoustic coupling component."

Coupling Element(s) and Assembly

An acoustic coupling device in accordance with some example embodiments of the present technology comprises a sonolucent coupling medium (SCM) used to efficiently transmit and receive US waves. In some example embodiments, the SCM can include a hydrogel material, which can conduct acoustic signals between a transducer element and a specimen (e.g., skin of a subject) in contact with the SCM to propagate the acoustic signal toward a VOI, where the SCM is coupled to the transducer element via a coupling element (e.g., bracket and/or adhesive) or via a coupling assembly, such that the coupling element or coupling assembly causes the SCM to be compressed to the transducer element while capable to conform to the specimen to achieve acoustic impedance matching between the receiving medium and the transducer element. Other examples of the SCM that can be used in acoustic coupling devices in accordance with the present technology include, but are not limited to, (i) a ballistics gel material (e.g., comprising styrene-ethylene-butylene-styrene (SEBS)), (ii) a paraffin gel material (e.g., comprising alkanes between 20-40 carbon atoms), (iii) a thermoform or thermoset low-elastic modulus TPX elastomer material (e.g., comprising polymethylpentene), (iv) one or more bladders filled with one or more of a mineral oil, water, an aquagel, and/or a paraffin gel, and/or (v) a silicone material (e.g., including a Shore 00-durometer to Shore D-durometer silicone rubbers, with or without fillers).

A. Adhesion Attachment Assembly

FIG. 1 shows a two-dimensional side section view of a schematic diagram of a method 100a and method 100b for coupling a SCM to a US array of an acoustic probe for transmitting and receiving acoustic signals between the acoustic probe (having an array of ultrasound transducers) and a specimen, in accordance with embodiments of the present technology. In some embodiments, the SCM includes a first region configured to interface with one or more transducers of the US array and a second region configured to interface with the specimen. In some embodiments, for example, the body of the SCM from the second region to the first region can include a tapered body shape, e.g., where the second region includes a larger dimension (e.g., radius, length or width, and/or area) than the first region. In some embodiments, for example, the first region may optionally include a ledge or rim structure (illustrated later in FIG. 2) that spans outward from the body of the SCM, which can allow for a securement site of the SCM with a coupling element or coupling assembly. In the upper illustrated embodiment shown in FIG. 1, method 100a includes coupling a US array 101a to a tapered SCM 102a and applying the tapered SCM 102a to a surface of a specimen 103a (e.g., human patient). Similarly, in the lower illustrated embodiment shown in FIG. 1, method 100b includes coupling a US array 101b to a non-tapered SCM 102b and applying the non-tapered SCM 102b to a surface of a specimen 103b (e.g., human patient). A tapered SCM has more surface area coupled to the patient preventing slip (e.g., when SCM at the patient-SCM interface moves) and averting the SCM from rolling/folding underneath itself. Conversely, a non-tapered SCM has less mass and less surface, allowing the SCM to slip-and-slide around the scan area.

For example, the method 100a and method 100b (sometimes referred to collectively as "method 100") allows for an attachment and removal of the tapered SCM 102a and non-tapered SCM 102b (sometimes referred to collectively as "SCM 102") from the US array 101a and US array 101b (sometimes referred to collectively as "US array 101"). The SCM 102 can be easily attached and then removed by peeling off the SCM 102 from the US array 101 after an examination and removal of the SCM 102 from the surface of the specimen 103a and 103b (sometimes referred collectively as "specimen 103").

In some embodiments, for example, SCM 102 comprises an adhesive, e.g., where the methods can include formulating the SCM 102 material with an adhesive. For example, in some embodiments, the SCM 102 includes an adhesive that borders an exterior surface of the SCM 102, e.g., where the method 100 can include applying an adhesive to the SCM 102 after forming the SCM 102. In some embodiments, the adhesive borders a US window (e.g., region where the transducers can steer the US beam without obstruction) of the US array 101. The method 100 can include formulating the SCM 102 or coating the SCM 102 with a low elastic modulus polymer that adheres to the US array 101 surface. Tacky polymers (i.e., polymer with a low modulus of elasticity, or within the 'visco-elastic window') can wet the surface of the US array 101, adhering the SCM 102 to the US array 101 surface.

In some embodiments, the SCM 102 is a highly adhesive (e.g., "sticky") SCM used for long, static US examinations. A sticky SCM 102 refers to a SCM 102 formulated to be adhesive across the entire surface of the SCM. The example embodiments of a sticky SCM are particular suitable for long, static examinations because the US array 101 does not need to move while the SCM 102 is contacting a surface of the specimen 103 (e.g., human patient). Static examinations can include needle guided biopsies, surgeries, cardiac exams, respiratory exams, and other exams where the target location is known.

In some embodiments, the SCM 102 is a "one-sided adhesive" SCM used for a dynamic examination. A one-sided adhesive SCM 102 refers to a SCM having a strongly adhesive layer (e.g., "sticky SCM" layer) on one-side of the SCM 102. A one-sided adhesive SCM 102 contrasts with a sticky SCM 102 because, instead of the entire SCM being sticky (e.g., SCM is formulated to be adhesive), the SCM includes only one side having a sticky layer that adheres to the US array 101. The one-side adhesive SCM 102 is particular suitable for dynamic examinations because the one-side adhesive SCM 102 moves while in contact with a surface of a specimen (e.g., human patient). It is noted, however, movement of the SCM 102 during a dynamic examination increases a risk for adhesive failure because the SCM 102 relies solely on adhesion to US array 101 and as such, the edges of the SCM contacting the specimen 103 can roll under the SCM 102 itself, causing the SCM 102 to peel away from the transducer interface. As such, in some embodiments, the method 100 includes applying a sonolucent lubricant (e.g., US gel) to the SCM 102 to reduce friction between the SCM 102 and specimen 103. With only one sticky side, the one-sided adhesive SCM 102 can perform dynamic scans to search for trauma or perform CT-examinations to generate 3D-models of the specimen morphology and anatomy.

In some embodiments, the method 100 includes adhering a SCM 102 to a US array 101 such that the SCM 102 does not bow or sag under the unsupported weight from gravity when the SCM 102 is held parallel to the floor. Geometry and material properties (e.g., Young's compressive modulus, Young's elastic modulus, shear modulus, and density) that constitute the SCM 102 influence the degree of bowing or sagging. For example, a SCM with a rectangular cross-section (e.g., 43.83 mm H×71.6 mm L) composed of freeze-thawed crosslinked poly(vinyl alcohol) hydrogel (e.g.

ρ=1.13 g/cc, E=120 kPa) mounted to a semicircular array (e.g., 200 mm ID, 180°) with a clamshell retainer will sag uniformly from its own weight, roll under itself, and peel away from the transducer surface during a dynamic scan of an adult male's neck (e.g. ~40 cm circumference). Therefore, a SCM 102 that sticks to the US array 101 ("one-sided adhesive SCM") should be limited to moderately thick SCMs for dynamic US examinations, but a SCM formulated with an adhesive material ("sticky SCM") can be thicker for long, static examinations.

B. Retainer and Fastener

Figure 2:
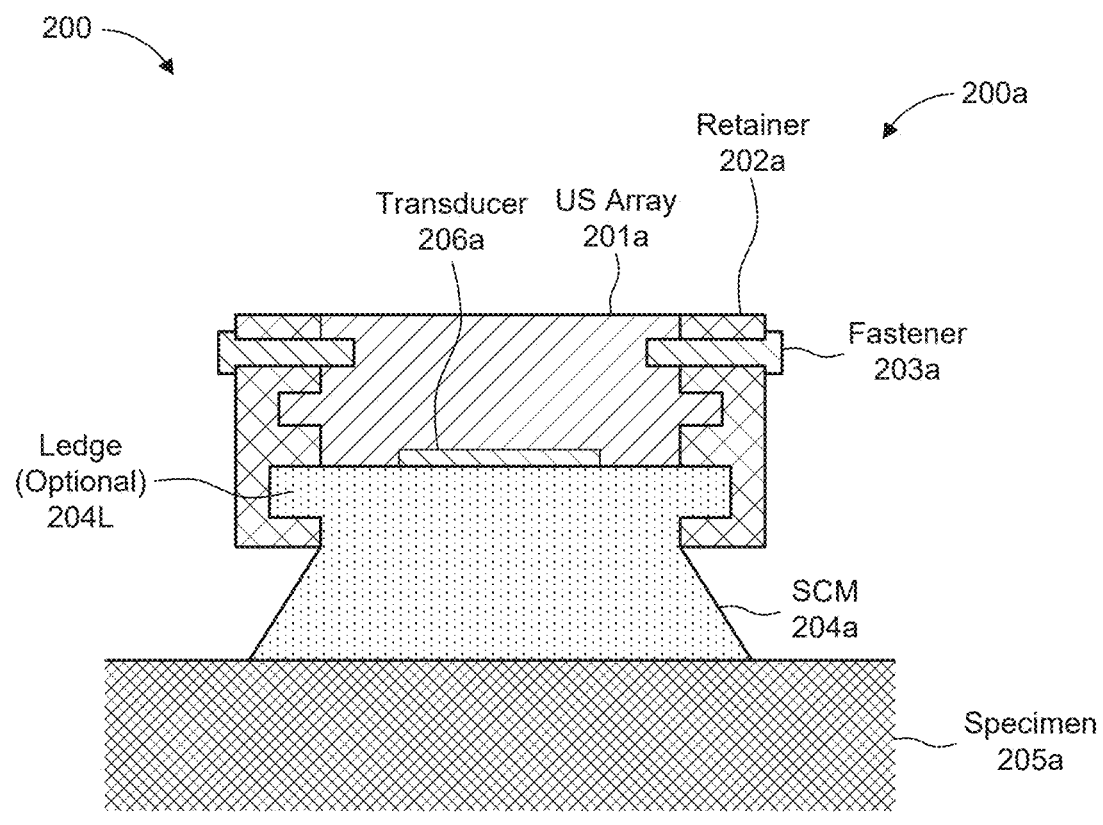
FIG. 2 shows a schematic diagram of exemplary embodiments and exemplary methods of manufacturing a SCM of disclosed technology.
Figure 2:
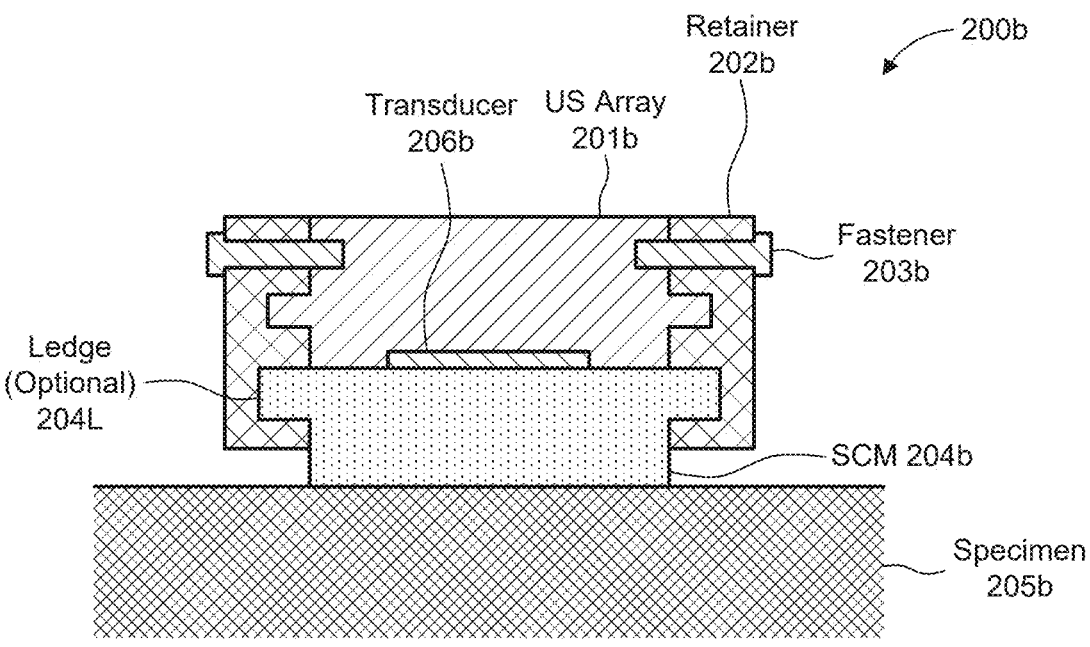

FIG. 2 shows a two-dimensional side section view schematic diagram of a method 200a and method 200b for coupling a SCM to a US array in accordance with embodiments of the present technology. In the illustrated embodiment, method 200a includes coupling a US array 201a to a tapered SCM 204a using fasteners 203a (e.g., screws, rivets, clips, etc.) and a retainer 202a (e.g., clamshell brackets, that close around the US array 201a) and then, applying the tapered SCM 204a to a specimen 205a (e.g., human patient), where a transducer 206a is placed between the US array 201a and SCM 204a. Similarly, in the illustrated embodiment, method 200b includes coupling a US array 201b to a non-tapered SCM 204b using fasteners 203b and a retainer 202b (e.g., clamshell brackets, that close around the US array 201b) and then, applying the non-tapered SCM 204b to a specimen 205b (e.g., human patient), where a transducer 206b is placed between the US array 201b and SCM 204b. Optionally, for example, in some embodiments, the SCM 204a and/or SCM 204b can be structured to have a ledge structure 204L at a first end of the SCM that is configured to interface with the transducer element(s) of the US array 201a and/or 201b, respectively, where the retainer 202a and/or 202b can secure the SCM 204a and/or 204b, respectively, via a recess portion of the retainer 202a and/or 202b that at least partially surrounds the ledge structure 204L of the SCM 204a and/or 204b so as to couple it to the transducer element(s) of the US array 201a and/or 201b, respectively. Optionally, in some embodiments, the fastener 203a and/or 203b can be applied to a portion of the retainer 202a and/or 202b (e.g., upper portion) to couple the SCM 204a and/or 204b to a portion of the US array 201a and/or 201b, respectively. In some implementations, for example, the fastener 203a and/or 203b is coupled to a housing or frame structure of the overall array of transducer elements or to a housing or structure of a transducer element of the array.

In the illustrated embodiments, the method 200a and method 200b (sometimes referred to collectively as "method 200") include using retainer 202a and 202b (sometimes referred to collectively as "retainer 202") and fasteners 203a and 203b (sometimes referred to collectively as "fasteners 203") that close around the US array 201a and 202b (sometimes referred to collectively as "US arrays 201") to form a cavity that compresses the SCM 204a and 204b (sometimes referred to collectively as "SCM 204") against the US array 201. The method 200 can include securing the retainer 202 to the US array 201 by fastening the retainer 202 (e.g., via fasteners) to the US array 201 or by fastening the fasteners (e.g., clamshell brackets) together to clamp around the US array 201. In some embodiments, the fasteners are clamshell brackets fastened together around a retention feature on a US array 201 (e.g., a ridge or groove), e.g., which can make cleaning and sanitation easier.

The retention force exerted on the US array 201 by the SCM 204 in the retainer 202 is dependent upon the SCM 204 material properties and the cavity dimensions of the retainer 202. For example, a SCM 204 made from low modulus of compression, tension, and shear viscoelastic materials-such as soft gels, soft hydrogels, soft elastomers, and other soft polymers—quickly relax, or creep, once inserted into the cavity and is compressed between the retainer and fasteners. In contrast, a SCM 204 made from high modulus of compression, tension, and shear elastomer behaving materials is securely retained against the US array 201 and experiences miniscule relaxation.

In some embodiments, SCM 204 used in conjunction with retainer 202 are suited for dynamic US examinations since the SCM 204 can glide over a surface of the specimen 205 during a US scan. However, because the SCM 204 is non-adhesive, this makes the non-adhesive SCM 204 more prone to slip and sliding, a detriment for long, static US examinations. Thus, retainer 202 fixation methods are better suited for protocols where the SCM 204 needs to be exchanged multiple times during a dynamic examination to couple the US array 201 to a multitude of variegated topographies on the specimen 205.

In some embodiments, the retainer and fastener assembly are used in the manufacture of small, one-handed, non-linear US arrays.

C. Overmolded Bracket Assembly

Figure 3:
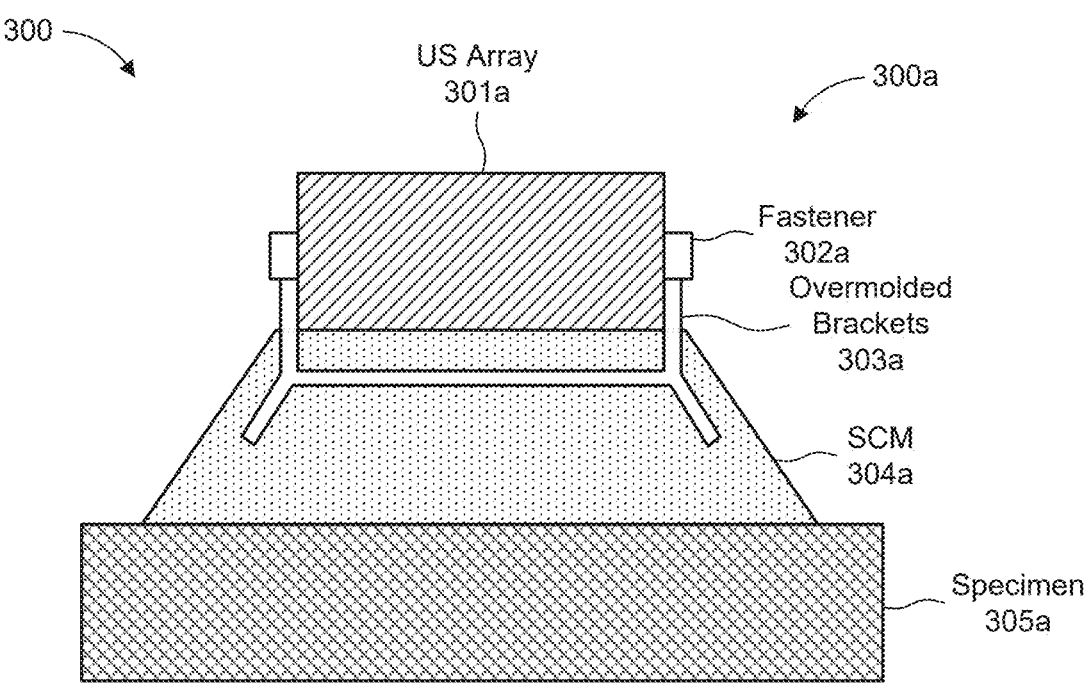
FIG. 3 shows a schematic diagram of exemplary embodiments and exemplary methods of manufacturing a SCM of disclosed technology.
Figure 3:
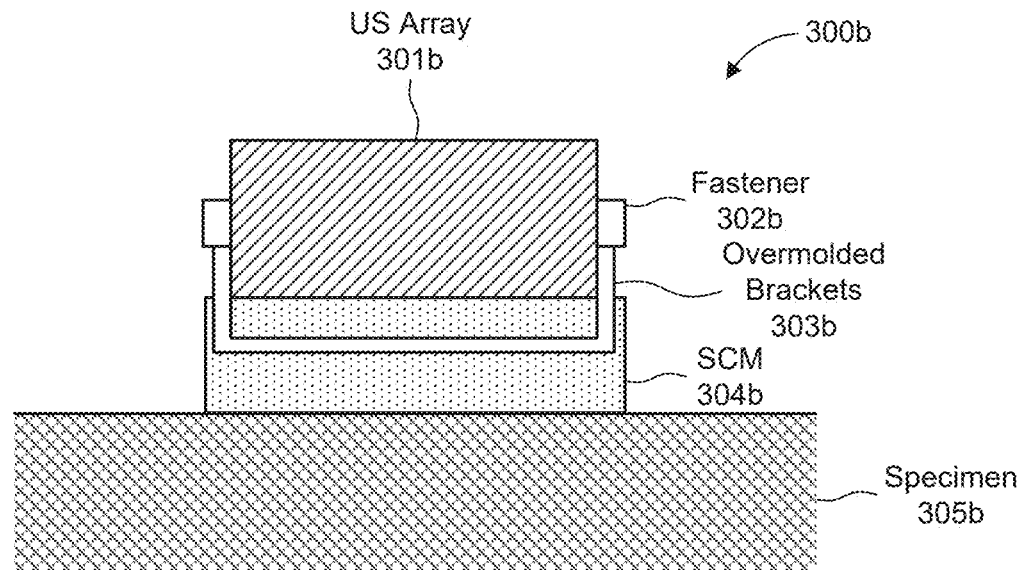

FIG. 3 shows a two-dimensional side section view schematic diagram of a method 300a and method 300b for coupling a SCM to a US array in accordance with embodiments of the present technology. In the illustrated embodiment, method 300a includes coupling a US array 301a to a tapered SCM 304a using an overmolded bracket 303a and a fastener 302a and then, applying the tapered SCM 304a to a specimen 305a. Similarly, in the illustrated embodiment, method 300b includes coupling a US array 301b to a non-tapered SCM 304b using an overmolded bracket 303b and a fastener 302b and then, applying the non-tapered SCM 304b to a specimen 305b.

In some embodiments, the method 300a and the method 300b (sometimes referred to collectively as "method 300") include embedding the overmolded bracket 303a and overmolded 303b (sometimes referred to collectively as "overmolded bracket 303") into a medium used to manufacture the SCM 304a and SCM 304b (sometimes referred to collectively as "SCM 304") when the SCM medium is pour-casted (e.g., a solution undergoing curing while poured into an open mold) or injection molded. The overmolded bracket 303 can provide both reinforcement against sagging, and a way to securely fasten, or mount, the SCM 304 to the US array 301a and US array 301b (sometimes referred to collectively as "US array 301"). In some embodiments, the overmolded bracket 303 is semi-flexible. In some embodiments, the overmolded bracket 303 comprises plastics with living hinges, elastomers with bridges, or fibrous polymer weaves that flex to accommodate a range of curvilinear, splined, and discontinuous US array geometries.

In some embodiments, the overmolded bracket 303 comprises a living hinge (e.g., a thin web of material connecting two larger bodies of the same material to allow an otherwise inflexible material to bend and distort without breaking). In some embodiments, the overmolded bracket 303 comprising a living hinge includes a plastic that does not deflect when applying a load horizontally and/or laterally to the SCM 304, preventing the SCM 304 from sagging. The rigidity of the plastic overmolded bracket 303 is especially useful if a large SCM 304 needs to extend far from the US array 301 to couple to an anatomic feature that would otherwise not fit a regular SCM 304 for that specific US array 301 geometry. For example, for a semi-circular array with a 180 degree arc length and 200 mm inner diameter (ID), an unsupported 4 cm-thick SCM cannot scan the cervical vertebrae because of poor SCM coupling to the neck. Air gaps between the neck and SCM are due to the oblong geometry of the neck (e.g., ~130 mm inner diameter for a human male). Increasing the SCM thickness to 8 cm and supporting the SCM with a 5 cm-deep overmolded plastic bracket fills in all the air gaps between the SCM and the specimen (e.g., patient's neck) and prevents the SCM from sagging. In some embodiments, the overmolded bracket 303 includes a plastic that reliably deforms and is resistant to chemical attack. For example, in some embodiments, the overmolded bracket 303 comprises poly(ethylene-vinyl acetate) (EVA), poly(ethylene) (PE), and/or poly(propylene) (PP) plastics.

In some embodiments, the overmolded bracket 303 comprises an elastomer ("elastomer overmolded bracket"). Elastomer overmolded brackets can connect rigid regions via semi-flexible bridges—sections of material with low moments of inertia connected to regions of material with high moments of inertia. By varying the cross-section geometry and dimensions, the stiffness of the elastomer bracket can be adjusted so that the bracket is flexible until it is installed on the US array 301. Once installed, the tabs protruding from the SCM 304 are buttressed against the US array 301 housing and are pulled taut when fastened to the US array 301 while simultaneously compressing the SCM 304 against the array housing, causing the tabs to become rigid under tension. The flexibility to create regions stiffer to normal loads in one direction and less so in others allows for the design of extra features, like wings, to stiffen regions of the SCM 304 prone to sagging, while still allowing the bracket 303 to deform as the SCM 304 is compressed.

In some embodiments, the elastomer overmolded brackets comprise thermoplastic elastomer (TPEs), liquid silicone rubbers (LSRs), natural rubbers, acrylonitrile butadiene styrene rubber (Nitrile rubber), and/or butyl rubber. For example, brackets can either be extruded, thermoformed, die cut, additive manufactured, cast, or injection molded. The range of materials and manufacturing methods provide a number of processing methods to tailor the mechanical properties of the elastomer overmolded bracket.

In some embodiments, the overmolded bracket 303 comprises a textile and/or fiber (e.g., "woven overmolded brackets"). In some embodiments, the method 300 includes imbedding the woven overmolded bracket 303 in the SCM 304 during the casting process and compressing the SCM 304 against the US array 301 by applying tension to the tabs on the woven overmolded bracket 303 when fastened to the US array 301 housing; however, unlike elastomer overmolded brackets, woven brackets comprise natural or artificial polymer fibers, e.g., including but not limited to gauze and canvas, which do not add to resistance against compressive strain or sagging of SCM 304. Consequently, design configurations cannot utilize winglet reinforcement. Instead, the woven fiber bracket provides resistance and additional strength only in tension while the elastomer bracket resists the SCM 304 deforming in tension and compression. Because the woven bracket exerts no resistance in compression, the SCM 304 can compress up to its maximum compressive strain. The compressive strain of the SCMs with a woven bracket is the same as the one-sided adhesive and sticky SCMs, and can more robustly attach to the US array 301 than the sticky and adhesive SCMs which solely rely on their adhesive properties to couple to the US array 301.

In some embodiments, the overmolded SCM design configurations include a fastener 302a and fastener 302b (sometimes referred to collectively as "fastener 302") installed on the US array 301 and the overmolded bracket 303 to compress the SCM 304 against the US array 301 to enhance acoustic coupling.

FIGS. 4A-4D show diagrams of exemplary fasteners, e.g., example embodiments of fastener 302, labeled as fasteners 402a-1, 402a-2, 402b, 402c, and 402d, which can be implemented for coupling a SCM 404 having an overmolded bracket 403 to an ultrasound (US) array 401, in accordance with the disclosed technology. Table 1 lists example advantages for each of the exemplary fasteners shown in FIGS. 4A-4D. The diagram of FIG. 4A illustrates the overmolded bracket 403 extending outside of the SCM 404 and attached to cantilever snap-fit fastener 402a-1 (right diagram of FIG. 4A) or to annular snap fit fastener 402a-2 (left diagram of FIG. 4A) to secure the SCM 404 to the US array 401. The diagram of FIG. 4B illustrates the overmolded bracket 403 extending outside of the SCM 404 and attached to example embodiments of a window-hangar mount fastener 402b (left and right diagrams of FIG. 4B) to secure the SCM 404 to the US array 401. The diagram of FIG. 4C illustrates the overmolded bracket 403 extending outside of the SCM 404 and attached to friction fit fastener 402c to secure the SCM 404 to the US array 401. The diagram of FIG. 4D illustrates the overmolded bracket 403 extending outside of the SCM 404 and attached to touch fastener 402d, which can be configured as push-to-connect or slide-to-connect touch fasteners, to secure the SCM 404 to the US array 401.

TABLE 1

List of Fastening Methods and Corresponding Advantages

| Fastening Method | Example Advantages | FIG. |
|---|---|---|
| Annular Snap Fit | Continuous connections Midsize SCM | FIG. 4A (right diagram) |
| Cantilever Snap-Fit | Plastic or elastomer overmolded bracket Large SCM | FIG. 4A (left diagram) |
| Window-Hangar Mount | Woven, plastic, or elastomer overmolded bracket Large SCM | FIG. 4B |
| Friction Fit Mounts | Easy SCM swapping Small SCM | FIG. 4C |
| Push-to-Connect Fasteners | Plastic or elastomer overmolded bracket Large SCM | FIG. 4D |
| Slide-to-Connect Fasteners | Easy SCM swapping Woven, plastic or elastomer overmolded bracket Midsize SCM | FIG. 4D |

In some embodiments, the bracket and fastener assembly are used in the manufacture of large, non-linear US arrays.

SCM Mounting/Fastening Methods

The acoustic coupling medium (e.g., SCM) of the disclosed technology can be mounted and/or fastened to a portion of an array of transducer element (e.g., the array's housing and/or a transducer element's housing) using various example embodiments of the fastener 302, including but not limited to (A) snap fits 401; (B) window-hangars 402; (C) friction fits 403; and/or (D) touch fasteners 404. In designing an appropriate mounting and/or fastening method, the criteria enumerated in Table 2 are considered.

TABLE 2

SCM Mounting/Fastening Method Criteria

| Criterium | Description |
|---|---|
| Sanitary | Mounting methods should avoid the following features: Pathogens protected by contaminant accretion on Rough and Porous Surfaces. Undercuts, Grooves, and Crevices shelter residual pathogens that can be overlooked during cleaning and sterilization. Threads and Teeth shelter pathogens that would require tedious cleaning and hazardous sterilization agents. Mounting method should have the following constraints: Array mating surface and mating fastener shall be Smooth and Non-Porous Array surface shall be Impermeable to bodily fluids, pathogens, fungi, and disinfection/sterilization methods. Array shall Not Have Hard-To-Clean Female Features that impede cleaning, sanitization, and sterilization protocols and methods typically used in clinical environments. Array mounting features shall Not Have Undercuts to clean and sterilize male and female mounting features on the array easier. Assembled mounting feature interface at array shall be Sealed, Glued, or Welded to prevent fluid wicking into crevices between the array and mounting feature. Hardware used to join the mounting feature to the array (e.g., screws, bolts, pins, and etc.) shall be Sealed to prevent fluid wicking between male and female threads. Mounting methods shall Not Use Threaded Fasteners to attach mounting hardware to array because female threads are difficult to clean and sterilize. Mounting features with teeth or grooves shall be a Removable Component of the mounting system for cleanability and sterilizability. |
| Usability | Mounting methods should avoid the following features: Non-Intuitive Design (e.g., Excessive Design) that can cause installation failure by the operator/user Prolonged pre-op or examination times due to Difficult Installation and Disassembly. General hassle from Obstruction of other equipment setup and operation. Mounting method should have the following constraints: Mounting the SCM to the array shall be Intuitive evinced by mounting mechanism design and simplicity Mounting mechanism installation and disassembly shall be simple for a Single Operator. For each use case SCM material properties (e.g., tackiness, toughness, compressibility, elongation, deflection, etc.) and user environment (e.g., exposure to lubricants, disinfection/sterilization solutions, and acoustic coupling agents, operating temperature, target size, SCM and Array geometry, and etc.) shall be Parameterized for Ease of Use. Mounting features and overmolded bracket shall Not Impede Clinical Procedure or Operator Efficacy. Mounting features and overmolded bracket shall Not Obstruct Array and Other System Functions. |
| Strong and Tough | Mounting methods should avoid the following: Geometries that induce Stress Risers in mounting mechanism. Weak Materials that break overmolded bracket or mounting features. In-adequate Chemical Resistance of the overmolded bracket or array mounting feature. In-adequate SCM Adhesion, Bond, or Mechanical Coupling Strength to the overmolded bracket. SCM Material Properties effect the max bend |

TABLE 2-continued

SCM Mounting/Fastening Method Criteria

| Criterium | Description |
|---|---|
| | radius and cross-section geometry of the SCM and overmolded bracket material and structure. Mounting methods should have the following constraints: Corners shall be Filleted to reduce stress risers. Thermoformed plastic cantilever fastener features protruding from the array shall have Imbedded Reinforcement to prevent catastrophic failure from impact. Overmolded bracket materials shall be Resistant to Chemical Attack by SCM and operating environment factors. SCM material shall be Elastic, Compressible, and Tough to fit array without tearing or delaminating from the overmolded bracket. Overmolded bracket mounting features shall Not Deform under load generated from SCM deformation. 3D-printed part Print Orientation shall be in the direction that maximizes part strength to prevent layer delamination and subsequent failure. |
| Fatigue and Wear Resistant | Mounting methods should avoid the following: Fatigue from repeated deformation leading to premature failure of mounting mechanism or the overmolded bracket. Array fastener Crazing from chemical exposure and/or thermal cycling causing premature failure. Wear or Abrasion from overmolded bracket fastener rubbing against complimentary mounting feature on array. Mounting methods should have the following constraints: Fastener features on the array shall be comprised of Rigid, Strong, and Tough Materials to prevent wear after repeated use. Rough, porous, and/or metallic surfaces on the array mounting features shall be Coated and Polished to prevent crack nucleation, and to protect against corrosion and chemical attack. Thermoform plastic cantilever fastener features on the array shall have Filler and/or Imbedded Reinforcement to resist creep and cracking from cyclic loading. |
| Cheap and Disposable | Mounting methods should avoid the following: Overmolded bracket or SCM materials (e.g., metals or thermoset plastics) that complicate, or are incompatible with, Biohazardous Disposal. Overcomplicated mounting mechanisms difficult and expensive to manufacture. Mounting methods should have the following constraints: Overmolded brackets shall be comprised of Disposable elastomers, plastics, or woven weaves for biohazardous waste processing. Array and overmolded bracket mounting features shall be easy to manufacture via current Conventional Manufacturing Methods available (e.g., injection molding, extrusion, die-cutting, vacuum forming, additive manufacturing, casting, 3-axis machining, and etc.). Overmolded brackets and mounting features shall be comprised of Inexpensive Materials and Components intended for disposal or incineration. |
| Robust Coupling | Mounting methods should avoid the following: Lack of SCM compression at the SCM-array interface that forms an Airgap. Excessive SCM compression at the SCM-array interface causing the SCM to Burst. Inclusion of air at patient-SCM interface from SCM Rolling/Folding underneath itself. Excessive Weight causing SCM to tear away from the overmolded bracket, or causing the acoustic couplant to detach from the array. Non-homogenous SCM material properties could cause refraction or reflections that Impeded Acoustic Transmission. |

TABLE 2-continued

SCM Mounting/Fastening Method Criteria

| Criterium | Description |
| --- | --- |
|  | Mounting methods should have the following constraints: Overmolded bracket shall Retain SCM against the array to expurgate trapped air and retain the SCM against the transducer face for good acoustic coupling. SCM and overmolded bracket Size, Design, and Material shall be predicated on required SCM properties for a given array design for a given clinical application. |

A. Snap Fits

In some embodiments of the fastener 302, a snap fit fastener can be used to secure the overmolded bracket to the array of transducer elements, e.g., via the array housing or a rigid structure (e.g., frame, housing, etc.) of one or more transducer elements. Snap-fits—also called "snap-joints"—lend to manufacturability by negating tools and fasteners for assembly. Example snap-fits can include protruding studs, hooks, or beads that deflect or cause deflection of the mating part. Snap-fits inserted into a mating part are strained until feature. Once the tip is completely pushed into the catch feature, the cantilever snaps back to its undeformed state and hooks the tip against the catch feature. Table 2 provides example constraint designs and parameters for cantilever snap-fits design which influence its applicability.

A permanent attachment can be achieved with a 90° relief angle (e.g., the relief slope where the cantilever joins the tip to hook into the catch feature). However, snap-fit components with a 90° relief can be removed if a disassembly feature is included. Typically, cantilever snap-fit with a 30° relief angle can be removed as easily as it was inserted because taper on the tip usually has the same slope (e.g., 30°). A relief angle between 80° and 35° will not be permanent but will require more force to remove. For clinical applications, for example, a relief angle of 90° can be used to secure the overmolded bracket tabs against the array.

Figure 5:
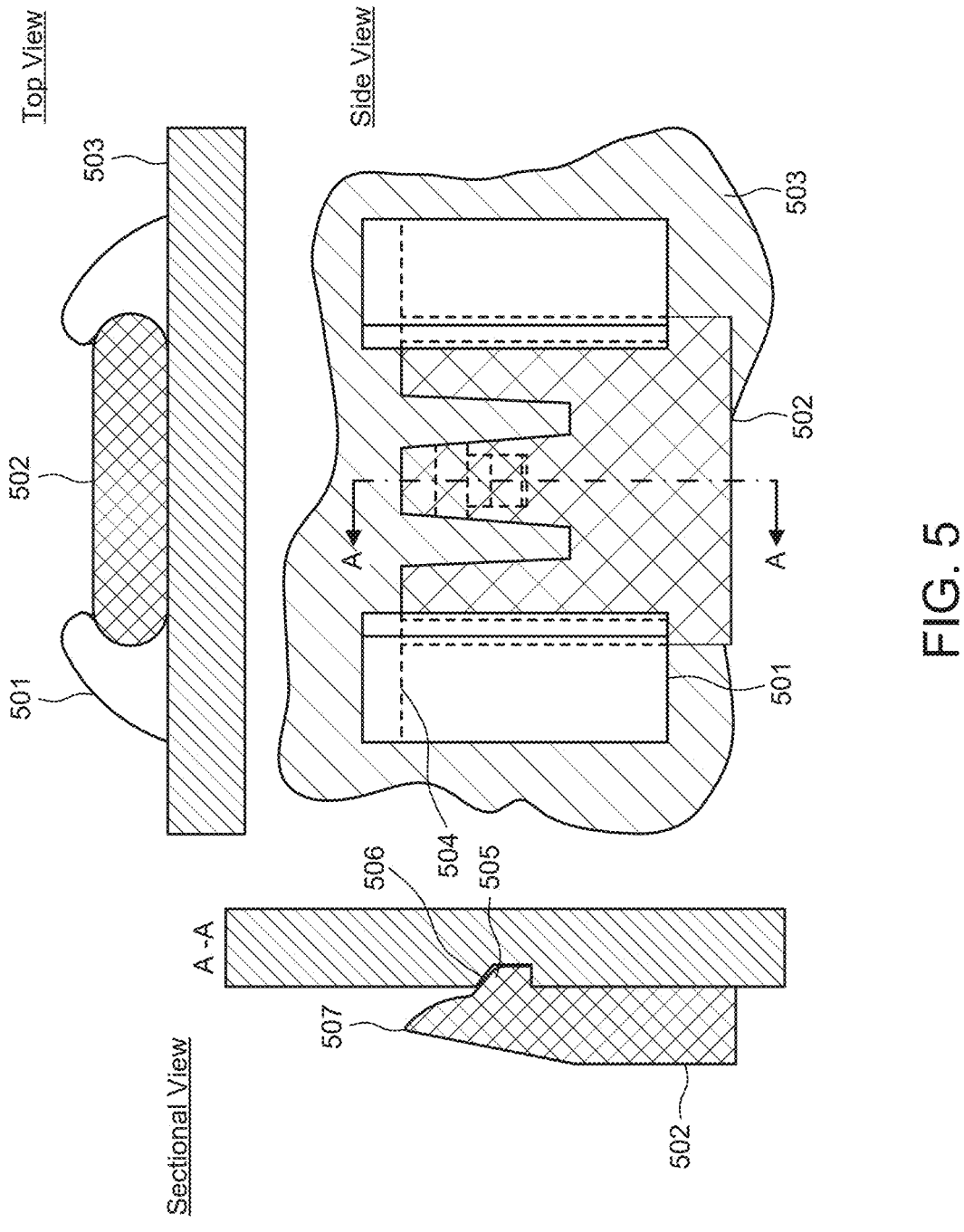
FIG. 5 shows an exemplary embodiment of an acoustic couplant mounting and/or fastening method including a front/side, cross-sectional, and top view of a cantilever snap-fit for an example plastic overmolded bracket tab of the disclosed technology.

FIG. 5 shows a diagram exhibiting a top view, a front view, and a sectional view of a cantilever snap-fit fastener for a plastic overmolded bracket tab that follows the cantilever snap-fit design constraints in Table 3 and the SCM mounting/fastening method criterium in Table 2.

TABLE 3

Cantilever Snap-Fit Design Constraints

| Constraint | Parameters | Reason |
| --- | --- | --- |
| Cantilever Minimum Fillet Radius | $>=\frac{1}{2} \times$ thickness of the cantilever base removes stress risers | Sharp corners at cantilever base lead to stress risers and premature failure |
| Cantilever Deflection | 30%-to-50% of the material yield strain for maximum deflection. | Additional stresses due to installation misalignment, manufacturing defects, and other anomalies could break the cantilever. |
| Cantilever Taper | Taper the cantilever 30-50% to match the flow of force streams to improve deflection and reduce stress | Non-uniform force streams generated from cantilever deflection causes excessive strain |
| Cantilever Width | Clip width >=5 mm to disperse loads from disassembly and assembly of mating components | Clip quickly fatigues after repetitive use if too thin. |
| Dovetail/Catch Material | Rigid plastic, or metal, with high fatigue strength | Frequent loading and use will cause deflected component to undergo fatigue strain |
| Overmolded Bracket Material | Plastic with high yield strain, tensile strength, and shear strength. | Plastic cantilever must be able to defect and hold the SCM under load without plastic deformation or breaking. | released in a "catch feature" (e.g., a pocket or female impression of the male geometry) which constrains the mated geometry—e.g., the clip on a bicycle helmet. A good snap-fit design is free of pre-load when parts are mated together especially for plastic or elastomer components which lose preload from creep.

Snap-fit fasteners can be configured as a permanent or a temporary fastener for a SCM. For some example SCM applications, the male snap-fit features are able to be configured for temporary connections in a female receptacle of the overmolded bracket to secure the SCM to the array via the overmolded bracket/fastener connection. The two types of snap-fits illustrated in FIG. 4A include: cantilever snap-fits and annular snap-fits.

Cantilever Snap-Fits

An example of a cantilever snap-fit design fastener includes a cantilever beam with a tapered hook that slides into the catch feature. The chamfered tip deflects the cantilever as it is pushed through a recess leading to the catch The diagram of FIG. 5 shows a dovetail assembly 501 fixed to surface 503 of the housing of the array of transducers can retains a tab 502 of an overmolded bracket to secure the SCM (not shown) to the transducer element(s) (not shown) of the array. For instance, the overmolded bracket tab 502 includes a cantilever hook 505 that can be guided, via the dovetail assembly 501, into a catch feature 506 in the array housing surface 503. In some embodiments, for example, to prevent the tab 502 from sliding past and out of the catch feature 506, a stop 504 is built into the end of the dovetail 501. To remove the tab 502 from the array 503, for example, a user can easily pull on a fingerhold 507 of the overmolded bracket tab 502 to lift hook 505 out of catch 506 while pulling tab 502 out of dovetails 501.

Robust coupling can be achieved through a rigid, semi-permanent connection from the dovetails 501 and array housing surface 503 constraining movement of the overmolded bracket tab 502 in all directions, with the only release mechanism normal to, and supported against, gravity. Only when the array is held in line with gravity does the cantilever experience the total distributed SCM weight and is in line with the strongest orientation of the cantilever snap-fit. When the array is held parallel to the floor (e.g., normal to gravity), all of the SCM weight is distributed across the overmolded bracket tabs 502 buttressed against the array housing body and dovetails 501. When the array is held at an angle, a combination of loading on the tabs and cantilever snap-fits is experienced.

To prevent cracking or deformation, for example, the cantilever width and thickness can be tapered to reduce deflection and stress at the fulcrum (e.g., the base of the cantilever). Dovetails 501 can be configured to be smooth and continuous, filleted, and use a shallow overhang for easy cleaning and sterilization. For example, the dovetails 501 can be made of low thermal expansion, high tensile strength, and high shear modulus plastic or metal to prevent crazing, cracking, deformation, and abrasion from cyclic loading and high-temperature sterilization. A coating can be applied to resist chemical attack from aqueous disinfectants and sterilizing agents. In addition, for example, the dovetails 501 can make installation an easy and intuitive process.

Annular Snap-Fits

Similar to retention rings, annular snap-fits can be used to join elliptical or circular features comprising of a male protrusion (e.g., plug) and a conjugate female feature (e.g., hub) to secure the SCM to the transducer element(s) of the US array. In some embodiments of an annular snap fit fastener assembly, for example, a ridge around the circumference of a male or female insertion feature snaps into a groove (e.g., catch feature) of a stationary, conjugate feature. As the ridge is pushed into or around the mating component hoop-strain is exerted. Once the ridge hooks into the catch feature, all hoop strain is relieved. Unlike cantilever snap-fits or torsion snap-fits, for example, the annular snap-fit fastener assembly can allow components to rotate if the plug and hub geometry is circular.

In some embodiments, for example, permanent mechanical attachment is determined by the relief angle of the ridge (e.g., the slope of the ridge that catches into the groove). For example, a 90° relief angle will permanently join two components together. A 30° relief angle is usually the same as the ridge insertion taper (e.g., 30°) and will require as much force to remove as it was to insert. A typical relief angle between 75° and 35° will not be permanent but will require more force to disassemble. For clinical applications, insertion force should be minimal (e.g., <300N), and removal force should be greater (e.g., 300-to-500N) to retain the overmolded bracket against the array. Insertion force is also dependent on the plug or hub being the deformable insertion feature, and material deflection and secant modulus derived from expected strain. An example of an annular snap-fit attachment for an elastomer overmolded bracket is given in FIG. 6 which abides annular snap-fit design constraints in Table 4 and mounting method criteria in Table 2.

TABLE 4

Annular Snap-Fit Design Constraints

| Constraint | Parameters | Reason |
|---|---|---|
| Hub Yield Strain | 50%-to-70% of the material yield strain for maximum deflection. | Misalignment when assembling annular snap-fits can exert greater deflections than anticipated, generating hoop-stresses past the |

16

TABLE 4-continued

Annular Snap-Fit Design Constraints

| Constraint | Parameters | Reason |
|---|---|---|
| Assembly Force | <=300N insertion force to reduce over stressing the flexible, stationary feature. | material yield point. Excessive force plus misalignment during assembly could generate enough shear stress to break the plug or hub housing. |
| Hub Groove/Ridge Distance | >1.8*(d*t)^(0.50) distance from the ridge or groove to the plug or hub base where d is the diameter of the hub or plug, and t is the hub wall thickness. | Ridges or grooves placed close to the base will be retained by less adjacent wall thickness and are prone to pull out when compared to ridges or grooves placed at the end. |
| Overmolded Bracket Material | Elastomer with high tensile strength, yield strain, and shear strength. | Plug will expand the undersized hub causing deflection, tension, and friction that could cause plastic deformation or catastrophic failure. |
| Plug Material | Rigid plastic, or metal, with high fatigue strength and high shear modulus | Frequent loading and deflection can cause component to fatigue and fail. |

Figure 6:
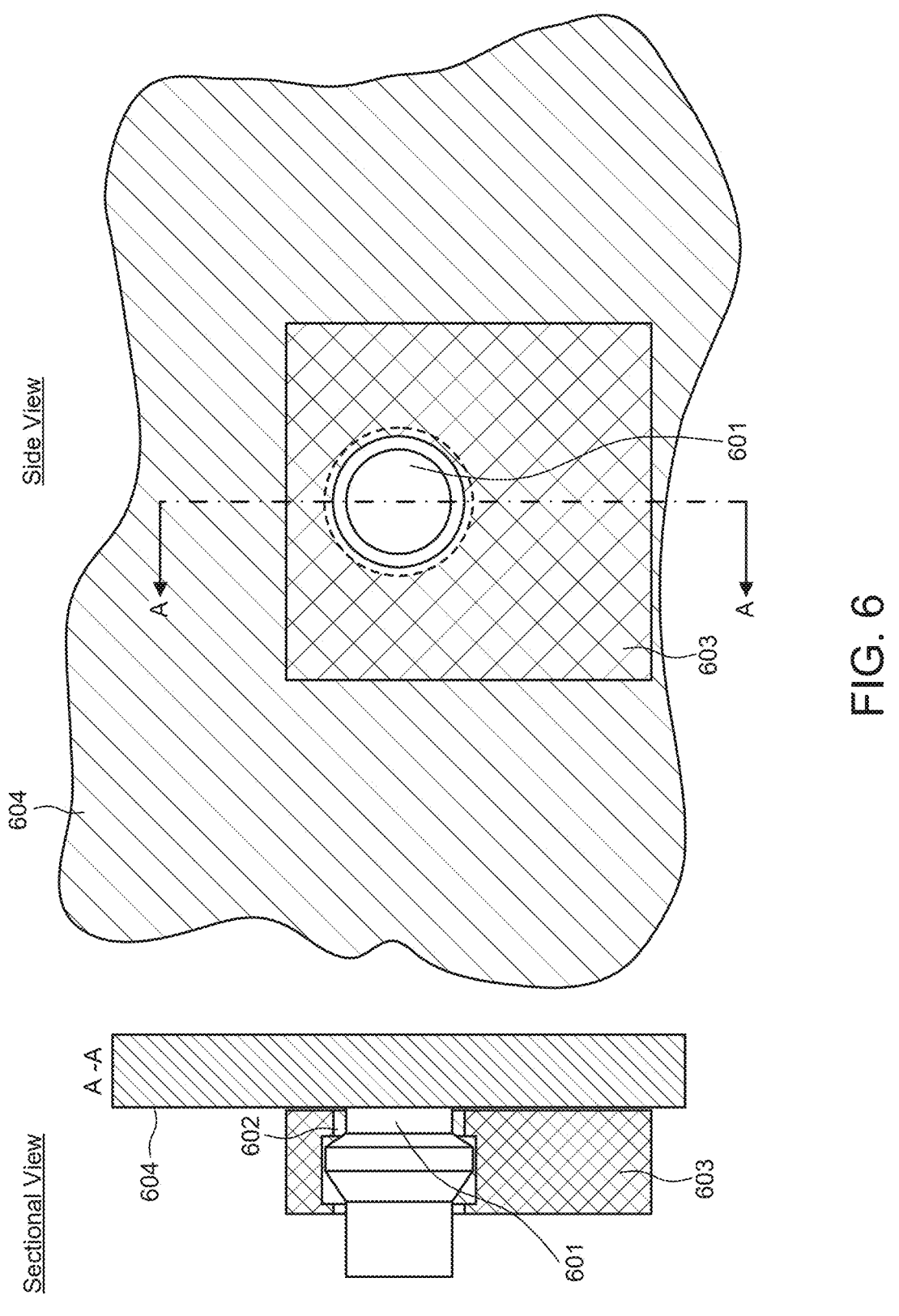
FIG. 6 shows an exemplary embodiment of an acoustic couplant mounting and/or fastening method including a front/side and cross-sectional view of an annular snap-fit for an example elastomer overmolded bracket tab of the disclosed technology.

FIG. 6 shows a side and cross-sectional view of an annular snap-fit fastener assembly for an overmolded bracket tab of an example SCM. As shown in the diagram, the annular snap-fit fastener can include a male protrusion 601 (e.g., plug, spanning from one of the array housing or overmolded bracket of the SCM) that inserts within a female recess 602 (e.g., hub: channel or groove, on the other of the array housing or overmolded bracket of the SCM). In some examples of the annular snap-fit fastener shown in FIG. 6, when tab 603 of an example overmolded bracket is mounted to array housing 604, little insertion force is needed as a shallow chamfer on a ridge of plug 601 gradually deflects the elastomer until plug 601 snaps into a groove or channel of the hub 602 (e.g., catch feature). Because the relief is steeper than the chamfer, more force is required to remove tab 603 from array housing 604, creating a secure connection. The base of tab 603 can then be peeled and twisted away from array housing 604 to decouple hub 602 from the plug 601.

When tabs are clicked into place, the flexible overmolded bracket becomes taut under tension, like a cable bridge, from compressing the SCM against the transducer element(s) of the array. For example, when array housing 604 is held parallel to the ground (e.g., perpendicular to gravity) the SCM weight is asymmetrically distributed to annular snap-fits under transverse load and tabs 603 buttressed against the top of array housing 604 which reduce axial-load on annular snap-fits on the bottom of array housing 604. When array housing 604 is held in line with gravity (e.g., parallel to gravity), all annular snap-fits are under transverse load to retain the SCM against array housing 604. When the array is held at an angle, a combination of loading on the annular snap-fits is experienced.

In some examples, the plug(s) 601 (configured on the array housing 603) can be made of thermoset plastic, metal, or thermoform plastic with imbedded reinforcement to provide multiple manufacturing options. Coatings can be applied to prevent corrosion, reduce friction, and improve surface finish. In some embodiments, for example, the plugs are features on the array housing instead of features on the overmolded bracket tabs to avoid undercuts that trap and accrete contaminants. Thus, cleaning and sterilizing the array surface can be a simple procedure.

Example elastomer tabs can prevent severe plastic deformation or failure of the hub during insertion and removal. Adjusting the groove distance from the end of the tab adjusts the groove wall thickness in contact with the ridge, thus tuning the insertion and removal force. In the exemplary illustration, the groove is placed near the end of the tab to increase the removal force for a robust mechanical and acoustic coupling between the SCM and array. In addition, contaminants entrapped within hub undercuts (e.g., body fluids, disinfectants, sterilizing agents, lubricants, etc.) can be simply disposed with the overmolded bracket, eliminating tedious cleaning and risk of patient-to-patient cross contamination.

B. Window-Hangars

In some embodiments of the fastener 302, hangars, or "hooks" are designed to be mechanisms that temporarily catch, anchor, or pull an item without additional fastener structures or tools. An example "window-hangar" connection is comprised of a "hangar" (e.g., a rigid cantilever with a lip) that catches and anchors a "window" (e.g., cutout in the overmolded bracket tabs) under tension as the SCM is secured to (e.g., compressed against) the array. In such embodiments, for example, a deep lip prevents the window unhooking from the hangar when the SCM is maximally compressed.

In various embodiments, a hangar can be elliptical or rectangular in cross-section. Elliptical hangars constrain window movement to 4-degrees of freedom (DOF): allowing only rotation about the hangar and up and down translation. Resistance to rotation increases as eccentricity increases. Tab rotation about the hangar can relieve strain on the elastomer bridge, plastic living hinge, or woven fabric when installing and removing the overmolded bracket. Rectangular hangars constrain window movement to 5-DOF: allowing only up and down translation. As a result, rectangular hangars create more rigid connections than elliptical hangars.

Windows are the same geometry as the hangar but are enlarged to allow the window to hook over the hangar. As the window is pulled over the hangar, the maximum experienced strain is exerted on the SCM (e.g., "overload"). Once over, the window rests on the hangar and the SCM remains in compression, acting as a spring that generates tension in the overmolded bracket.

Figure 7:
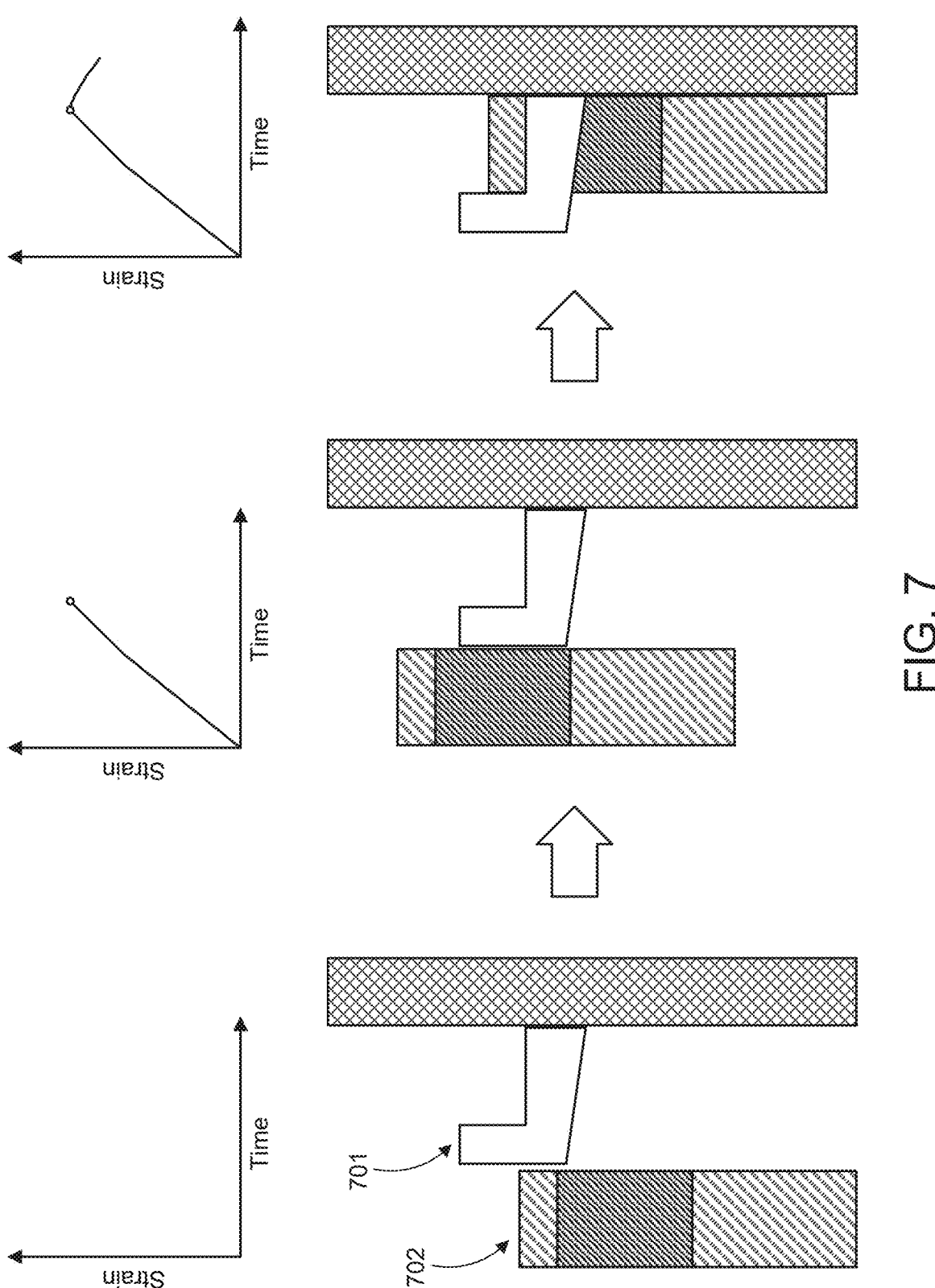
FIG. 7 shows an exemplary embodiment of a mounting and/or fastening method that generates tension in and example overmolded bracket of the disclosed technology.
Figure 8:
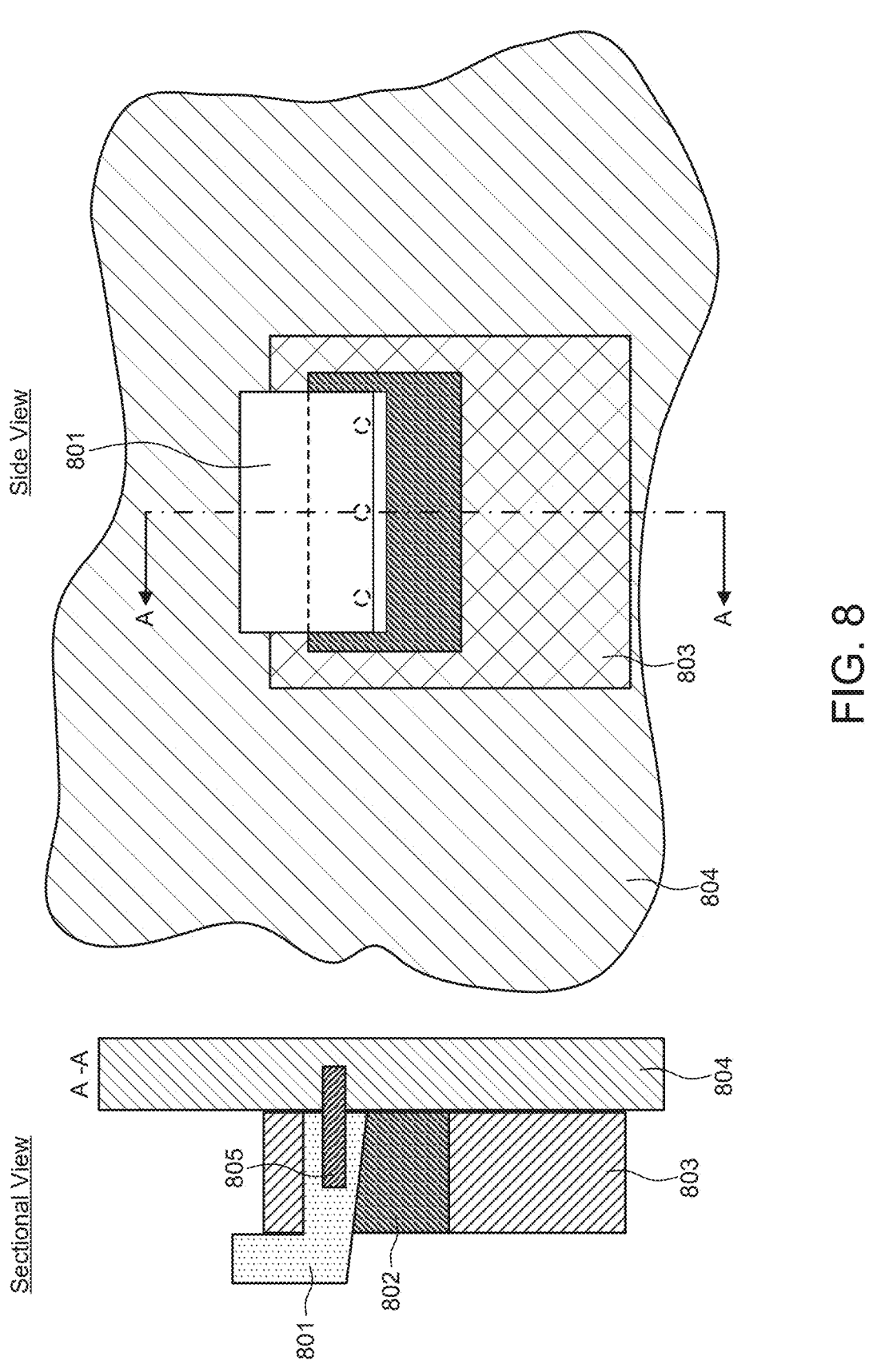
FIG. 8 shows an exemplary embodiment of an acoustic couplant mounting and/or fastening method including a front/side and cross-sectional view of a hangar for an example plastic overmolded bracket tab of the disclosed technology.

FIG. 7 shows a series of diagrams featuring a mounting and/or fastening method that generates tension in an example window-hanger fastener assembly in accordance with the disclosed technology. The graphs in the image series of FIG. 7 demonstrate how SCM strain changes as window 702 is hooked onto hangar 701. An example embodiment of a hangar-window connection is also shown in FIG. 8, which abides by the example hangar design constraints listed in Table 5 and the example mounting method criteria listed in Table 2.

TABLE 5

Hangar mount design constraints

| Constraint | Parameters | Reason |
|---|---|---|
| SCM compressive yield strain | Overload <=75% SCM compressive yield strain. | Low yield SCM could plastically deform or fail during overload - e.g., the maximum experienced SCM strain and tab stress during installation |

TABLE 5-continued

Hangar mount design constraints

| Constraint | Parameters | Reason |
|---|---|---|
| | | and removal). |
| Hangar Material | Rigid plastic, or metal, with high fatigue strength and high shear modulus | Frequent loading and deflection can cause component to fatigue and fail. |
| Overmolded Bracket Material | Woven, plastic, or elastomer materials that have high tensile strength and high tear strength. | The mass of the SCM and the tensile load from the SCM under compression could deform or rupture the window. |

FIG. 8 shows a diagram depicting a front/side view and cross-sectional view of an example embodiment of a window-hanger fastener assembly. The window-hanger fastener includes a rectangular window 802 hooked over a rectangular hangar 801, which can rigidly mount overmolded bracket tabs 803 to array housing 804. To remove the overmolded bracket (via tabs 803) from the array housing 804, for example, the window structures 802 are unhooked from the hangars 801.

In some implementations, for example, when array housing 804 is held parallel to the ground (e.g., perpendicular to gravity) the SCM weight is asymmetrically distributed to window-hangar connections under transverse load and overmolded bracket tabs 803 buttressed against the top of array housing 804 which reduce axial-load on window-hangar connections on the bottom of array housing 804. When array housing 804 is held in line with gravity (e.g., parallel to gravity), all window-hangar connections are under transverse load to retain the SCM against array housing 804. Steel locating pins 805 reinforce hangars 801 under transverse load. When the array is held at an angle, a combination of loading on the annular snap-fits is experienced.

Hangars can be injection molded from thermoform plastic (e.g., nylon), located onto the array via steel locating pins that double as reinforcement, then welded into place. Reinforcing hangars prevent creep, crazing, and cracking from cyclic loading. Thermoplastic film (e.g., 3-10 mil thick PETG) can be die cut to make the overmolded bracket 2D-profile (e.g., US-window, tabs, frame, windows, etc.) and then bent to form 3D-features (e.g., tabs, wings, etc.). Thus, a simple and cheap manufacturing processes can be utilized.

In some embodiments, for example, hangars do not have undercuts, crevices, or grooves which make cleaning and sterilization simple. To prevent chemical attack, for example, hangar and array surfaces can be coated to prevent crazing, cracking, and embrittlement. For autoclaving, thermoplastic hangars should be made of high glass transition temperature (e.g., >220° C.), high deflection temperature (e.g., >200° C. @ 0.46 Mpa), and high intermittent service temperature (e.g., >190° C. @ 100,000 cycles and 3 min/cycle) plastic to prevent thermal degradation and dimension change at elevated pressure (e.g., 1.0-2.0 bar). Fillers (e.g., glass beads, glass fiber, etc.) can be added to improve thermal-mechanical properties, rigidity, and dimensional stability.

Adjusting the hangar lip relief height will change the force needed to lift the window over the hangar. Tall reliefs require more force, suitable for long examinations or protocols that need only one SCM. Shorter require less force, reliable for short examinations with multiple SCM swaps. The maximum relief height is dependent on the overload during installation and removal. Overload must be beneath the maximum SCM compressive yield strain to prevent plastic deformation.

C. Friction Fits

In some embodiments of the fastener 302, a friction fit, or "interference" or "press" fit, can be used to produce a joint held together by friction. The amount of interference effects the magnitude of experienced friction and case of joint separation. For example, for mounting the SCM, a friction fit connection may comprise of a "pin" (e.g., rigid cylindrical shaft) or "core" (e.g., rigid non-cylindrical projection) inserted into a conjugate "cavity" (e.g., deformable inverse of core/pin geometry).

The friction fit can either comprise of a core or pin. The pin can be a single structure such as a metal shaft joined to the array housing, or an integrated feature on the array housing (e.g., stamped, thermoformed, etc.). Pins will allow 4-DOF: allowing tab rotation about the pin and axial translation. Tab rotation about the pin can relieve strain on the elastomer bridge when installing and removing the overmolded bracket. Cores can vary geometrically to change the case of insertion and difficulty of removal. As such, cores typically constrain 5-DOF: allowing axial translation. As a result, core friction fits tend to be more rigid than pin friction fits.

Figure 9:
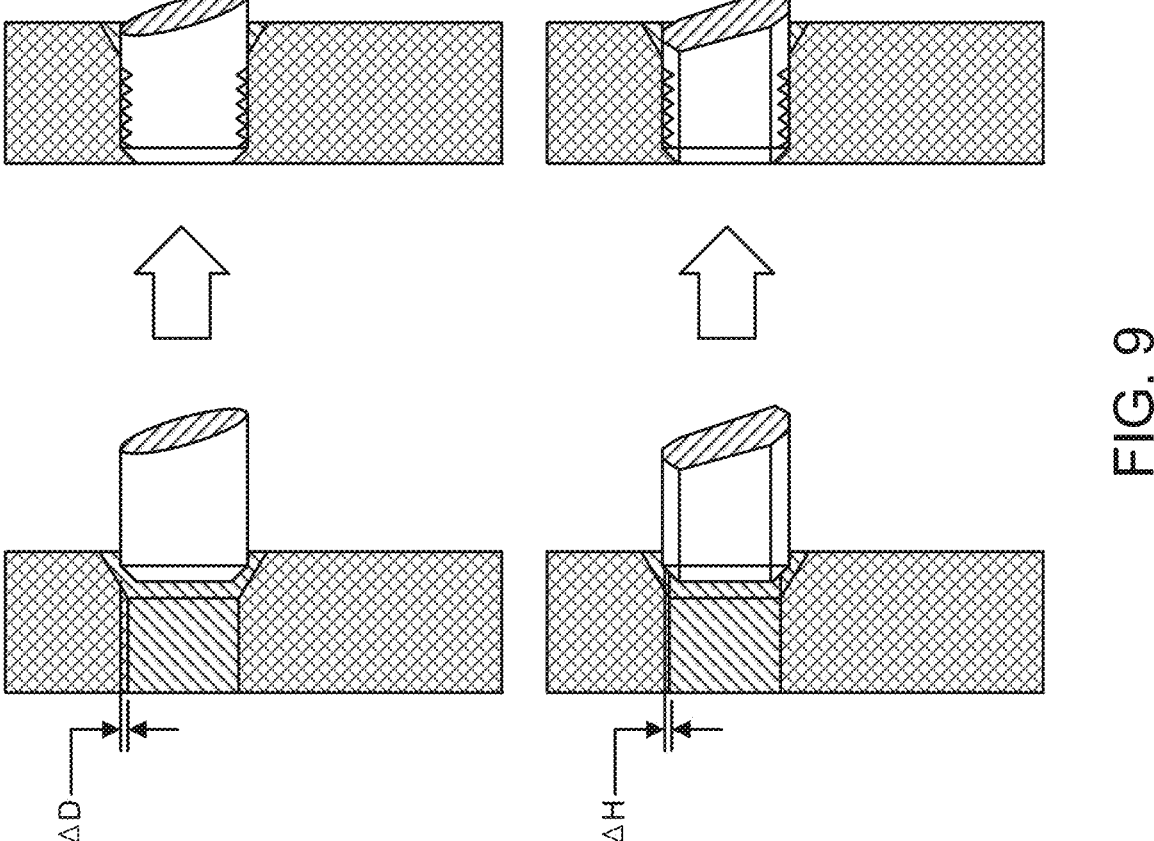
FIG. 9 shows an exemplary embodiment of a cross-sectional view of an interference fit comprised of a pin and rectangular core, and an example elastomer cavity of the disclosed technology.

FIG. 9 shows a diagram depicting a cross-sectional view of an interference fit fastener comprised of a pin and rectangular core, interfacing with an elastomer cavity. Cavities have the same geometry as the core or pin but are undersized for interference. As demonstrated in FIG. 9, the cavity deforms from its nominal dimensions and compresses against the pin or core for a tight friction fit. Chamfering enables pin or core self-alignment into the cavity, making location easier during installation. An example of a friction fit connection is given in FIG. 9, which abides friction fit design constraints in Table 6 and mounting method criteria in Table 2.

TABLE 6

Friction fit design constraints

| Constraint | Parameters | Reason |
|---|---|---|
| Cavity Yield Strain | 50-to-80% of elastomer yield strain for max interference fit of the cavity | Exceeding the yield strain of the elastomer cavity could cause plastic deformation, relaxation, or rupture that cause joint failure. |
| Assembly Force | <=500N insertion force to reduce over stressing the core or pin. | Excessive force could injure the operator or can cause damage to the pin or the core. |
| Deburred, Tapered, and Chamfered | Pin and cores should be deburred and tapered, and cavity should be chamfered to self-align joint during assembly. | Misalignment and burrs will cause the edge of the pin or core to catch onto the cavity walls, increasing insertion force. |
| Pin/Core Material | Rigid plastic, or metal, with high fatigue strength and high shear modulus | Frequent loading and deflection can cause component to fatigue and fail. |
| Overmolded Bracket Material | Elastomer with high tensile strength, yield strain, coefficient of friction, and shear strength. | Pin or core will expand the undersized cavity causing deflection, tension, and friction that could cause plastic deformation or catastrophic failure. |

Figure 10:
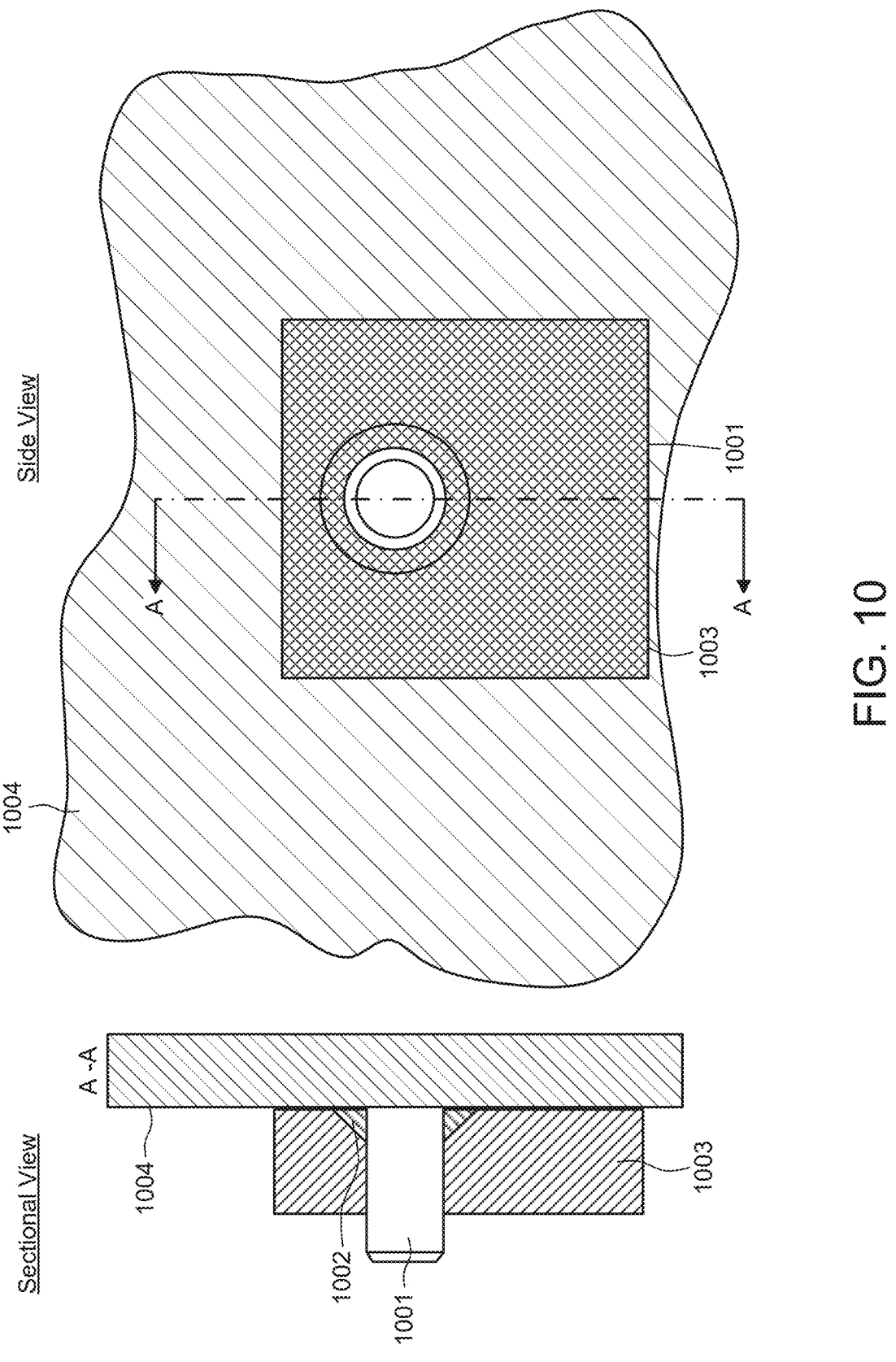
FIG. 10 shows an exemplary embodiment of an acoustic couplant mounting and/or fastening method including a front/side and cross-sectional view of friction fit for an example elastomer overmolded bracket of the disclosed technology.

FIG. 10 shows a diagram depicting a front/side view and cross-sectional view of an example embodiment of a friction fit fastener assembly. The friction fit fastener includes a pin 1001 spanning from one of the array housing or the overmolded bracket of the SCM that is pushed into circular cavity 1002 within the array housing or the overmolded bracket to mount overmolded bracket tabs 1003 to array housing 1004. Once mounted, the SCM is compressed against the array exerting tension on the overmolded bracket. Friction generated from the elastomer cavity 1002 compressing the rigid pins 1001 prevents the joint from separating under axial load. To remove the overmolded bracket from the array, tabs 1003 are pulled away from array housing 1004.

For example, when array housing 1004 is held parallel to the ground (e.g., perpendicular to gravity) the SCM weight is asymmetrically distributed to friction fits under transverse load and tabs 1003 buttressed against the top of array housing 1004 which reduce axial-load on friction fits on the bottom of array housing 1004. When array housing 1004 is held in line with gravity (e.g., parallel to gravity), all friction fits are under transverse load to retain the SCM against array housing 1004. When the array is held at an angle, a combination of transverse and axial load is experienced.

Metal pins (e.g., stainless steel locating pins) can be press fit, fastened, or welded to the array housing. Low profile, coated metal pins projecting from the array will not deflect under load, will withstand thermal cycling (e.g., autoclaving), and can withstand multiple cleaning and sterilizing methods (e.g., alcohols, liquid chemical sterilization, vaporized hydrogen peroxide, ethylene oxide, low temperature plasma, etc.). The overmolded bracket can be composed of a semi-flexible thermoplastic elastomer with high coefficient of friction (e.g., thermoplastic styrene-block-copolymers) to compress and grip the pins.

In some implementations, for example, increasing pin-cavity interference increases the insertion and removal force, and static friction. Axial translation of the tab along the pin is solely resisted by cavity compression and friction. One-handed, non-linear arrays for dynamic scanning require thinner SCMs; thus, less insertion force is needed to retain the SCM against the array. Conversely, dynamic examinations with large, non-linear arrays demand bigger SCMs; as a result, more insertion force is required to prevent premature disengagement of the joint. For general static examinations, less insertion force is necessitated.

D. Touch Fasteners

Hook-and-loop (HnL) fasteners can be used for mounting static, non-critical components across multiple industries, commercial applications, and residential settings. In medical settings, however, woven synthetic fabric and micro-hooks provide haven for pathogenic and adventitious particulates during cleaning and sterilization that lead to patient-patient cross contamination. A derivative of HnL fasteners resolves cross contamination issues: touch fasteners.

Similar to its parent, touch fasteners form a joint by interlocking a hook feature and a "catch" feature (e.g., a pocket or another hooking feature). Touch fastener features are macroscopic ensuring entire hook and catch engagement in comparison to HnL fasteners which have random, indeterminate engagement (e.g., typically 30% of loops catch into the hooks). Because macroscopic features are easier to clean and are stronger than microscopic features, touch fasteners provide a viable method to mount the SCM to the array.

Depending on the hook and catch feature geometry, touch joints can be strong under transverse and/or axial loads. Exceptional strength can be achieved if hook and catch features are on rigid substrates to prevent bending and flexion of the joint. To remove the SCM from the array, the touch hook or catch feature on the overmolded bracket tabs are peeled away from the conjugate mating component.

Two types of touch fasteners included among the example embodiments of the fastener 302 include: push-to-connect and slide-to-connect.

Push-to-Connect

In some embodiments of the fastener 302, Push-to-Connect (PtC) fasteners use strong interlocking features that deflect and snap back into their unloaded conformation: like snap-fits. Unlike snap-fits, however, PtC fasteners have several interlocking features to form a secure joint. The cumulative PtC connections increase the joint strength to form a rigid and unyielding connection. For example, some quick-to-install and release fasteners have matts with hundreds, or thousands, of small mushroom shaped features that slide past one another and snap back to form a joint. Again, for medical applications, macroscopic mating features are needed for cleaning and sterilization; thus, small intermeshing features cannot be used without posing risk of patient-to-patient cross contamination.

Figure 11:
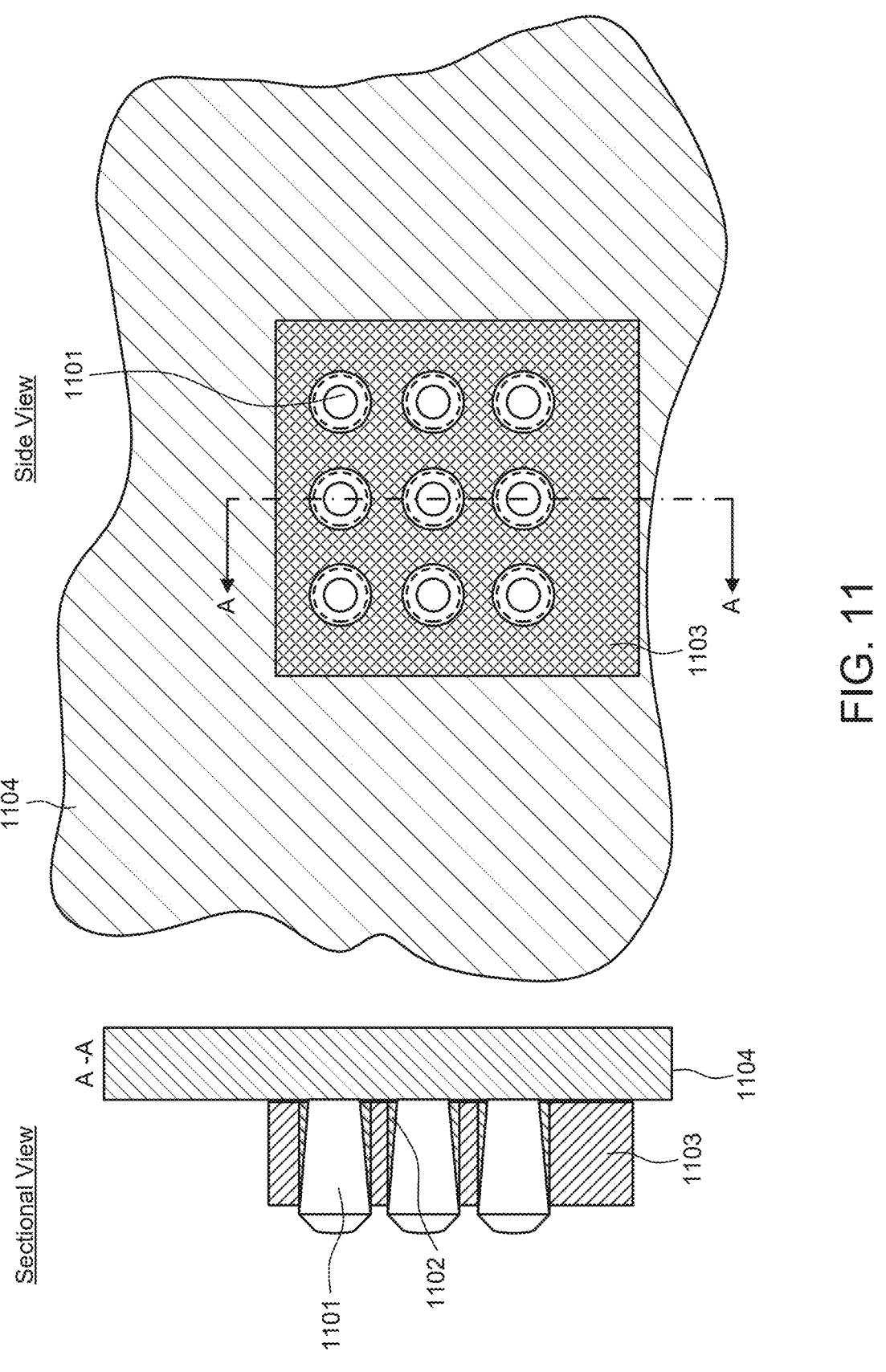
FIG. 11 shows an exemplary embodiment of an acoustic couplant mounting and/or fastening method including a front/side and cross-sectional view of a Push-to-Connect fastener for an example elastomer overmolded bracket tab of the disclosed technology.

A PtC fastener concept is presented in FIG. 11 which abides PtC design constraints in Table 7 and mounting method criteria in Table 2.

TABLE 7

| Slide-to-Connect (StC) design constraints | | |
| --- | --- | --- |
| Constraint | Parameters | Reason |
| Male StC Material | Rigid plastic, or metal, with high fatigue strength and high shear modulus. | Frequent loading and deflection can cause component to fatigue and fail. |
| Overmolded bracket material | Semi-flexible elastomers or rigid plastic with high fatigue strength and elastic modulus. | Male StC feature will wedge into the female StC feature causing deflection and tension that could cause plastic deformation or rupture the overmolded bracket. |

FIG. 11 shows a diagram depicting a front/side view and cross-sectional view of an example embodiment of a PtC fastener assembly. The PtC fastener includes a plurality of studs 1101 spanning from one of the array housing or overmolded bracket of the SCM to interface with a corresponding plurality of perforations 1102 within one of the array housing or overmolded bracket of the SCM. For example, to mount overmolded bracket tabs 1103 to array housing 1104, the studs 1101 are pushed into the perforations 1102 causing the perforations to deflect and expand. Once studs 1101 pass through overmolded bracket tab 1103, strain exerted on perforations 1102 is relieved and overmolded bracket tab 1103 is retained against the relief of stud 1101. Once mounted, the SCM is compressed against the array, generating tension in the overmolded bracket.

When array housing 1104 is held parallel to the ground (e.g., perpendicular to gravity) the SCM weight is asymmetrically distributed to PtC connections under transverse load and tabs 1103 buttressed against the top of array housing 1104 which reduce axial-load on PtC connections on the bottom of array housing 1104. When array housing 1104 is held in line with gravity (e.g., parallel to gravity), all PtC connections are under transverse load to retain the SCM against array housing 1104. When the array is held at an angle, a combination of loading on the annular snap-fits is experienced.

The cumulative PtC connections constrain tab movement to axial translation along the studs during installation and removal, forming a robust and immobile joint. Adding more studs will increase the holding strength of the joint and vice versa. The stud relief slope is dependent upon the stud relief diameter and tab thickness. Increasing the relief slope increases PtC disjoin resistance. To demount the joint, tabs are peeled away from array.

Studs 1101 can be integrated into the array housing 1104 cast from thermoset plastic (e.g., polyurethane) for increased strength. Additional fillers and imbedded reinforcement can be added to improve rigidity and reduce heat deflection. Perforated overmolded brackets can be injection molded or additive manufactured from a thermoform semi-flexible elastomer (e.g., thermoplastic polyurethane) for strength and elasticity.

In some embodiments, for example, there are no undercuts, nooks, crevices, nor crannies on the array mounting features to harbor adventitious fluids or particulates during cleaning and sterilization.

Slide-to-Connect Fasteners

In some embodiments of the fastener 302, Slide-to-Connect (StC) fasteners are similar to HnL fasteners where a hook feature snags an undercut that locks and meshes the two parts together. The principle is similar to a burr hooking onto tangled animal fur, or how the teeth like morphology on spider feet allow spiders to climb rough surfaces. Some products use fenestrated islands that link together via meshing undercuts like how the hollows in zipper teeth stack on top of one another. While viable for several cases, undercuts pose patient-patient cross contamination risk. Thus, cleaning and sterilization requirements necessitate undercuts and hollows to be located only on the overmolded bracket.

To mount the SCM, hollows with undercuts are located on the overmolded bracket tabs to engage hook features located on the array. Hooks are filleted, smooth, and seamless to prevent adventitious particulates and fluids from wicking or accreting. Hollows are oversized to align StC features. Once aligned, the hooks are slid until engaged in the undercut, creating the joint. A StC fastener concept is presented in FIG. 12 which abides StC design constraints in Table 7 and mounting method criteria in Table 2.

Figure 12A:
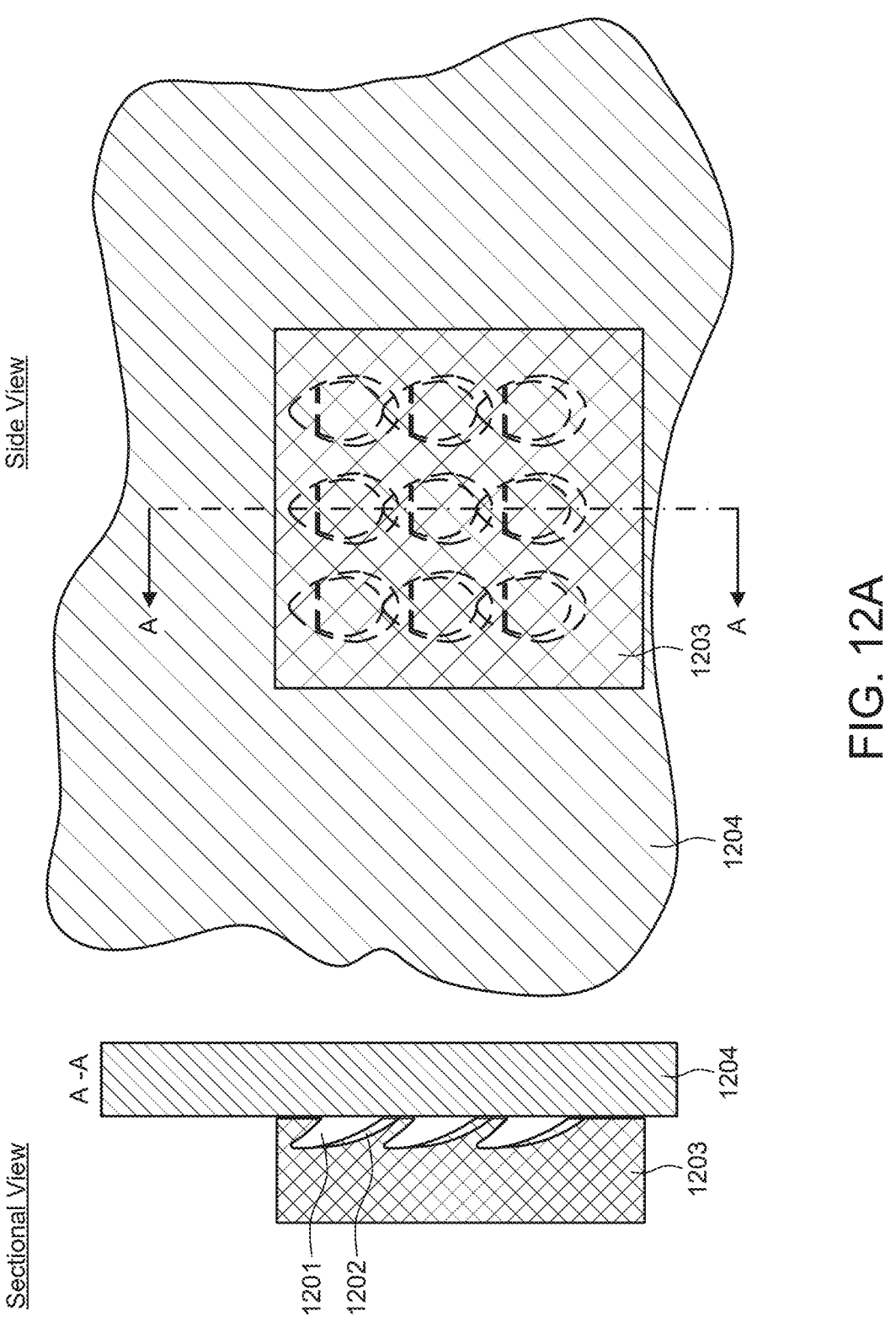
FIGS. 12A and 12B show an exemplary embodiment of an acoustic couplant mounting and/or fastening method including a front, cross-sectional, and top view of Slide-to-Connect fastener for an example elastomer overmolded bracket of the disclosed technology.
Figure 12B:
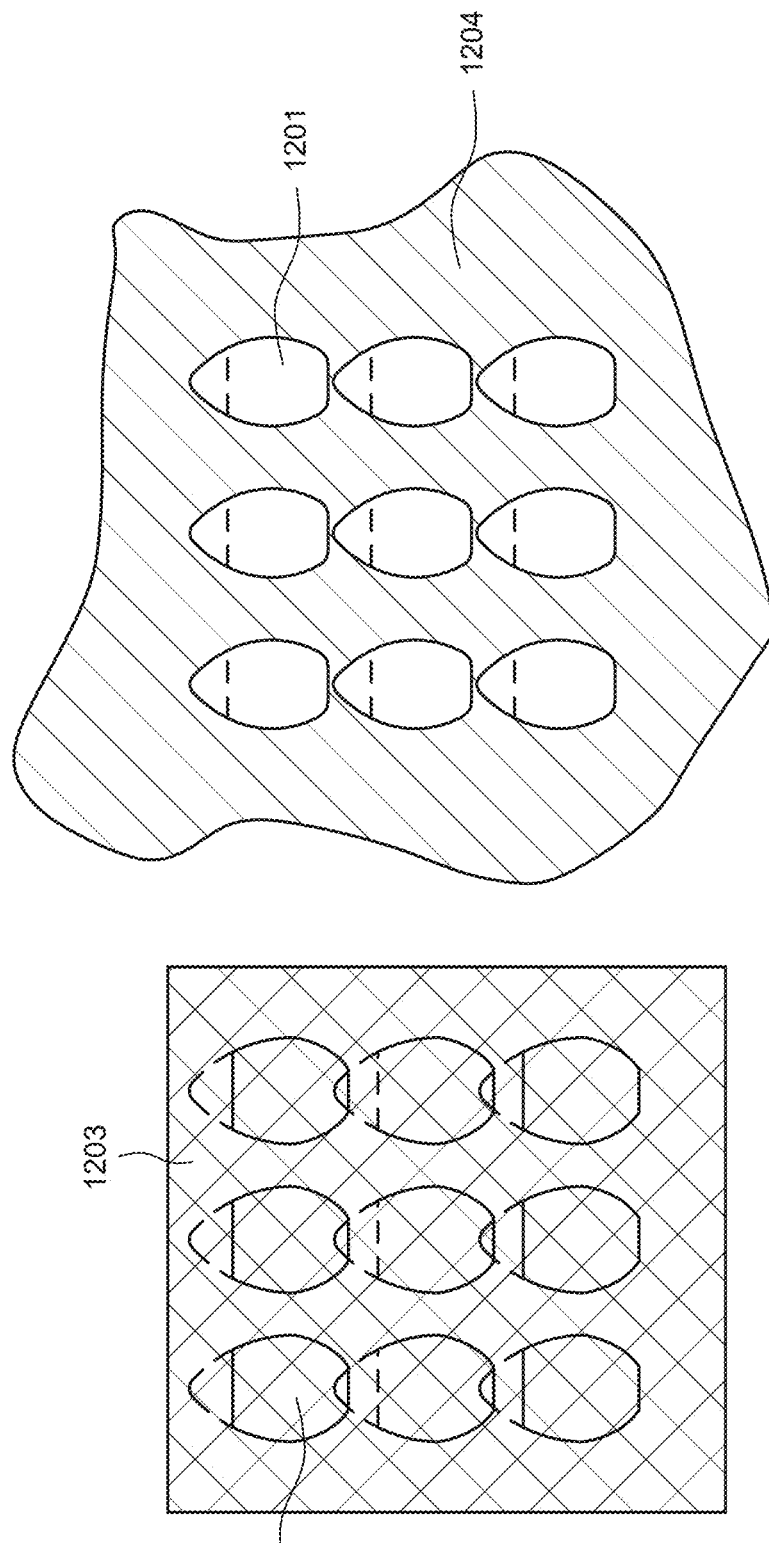

FIGS. 12A and 12B show diagram depicting a front/side view and cross-sectional view of an example embodiment of a StC fastener assembly. The StC fastener includes a plurality of hooks 1201 spanning from one of the array housing or overmolded bracket of the SCM to interface with a corresponding plurality of hollow alignments 1202 (e.g., cavities of similar shape, size of hooks) within one of the array housing or overmolded bracket of the SCM. For example, to mount overmolded bracket tabs 1203 to array 1204, example oval-shaped hooks 1201 are aligned into the oversized tear-drop hollows 1202. Once the hooks 1201 are aligned in hollows 1202, tab 1203 is slid down in order for hooks 1201 to engage the undercut. Once mounted, the SCM is compressed against the array, generating tension in the overmolded bracket. To demount the SCM, tabs 803 are pulled up and peeled away.

When array housing 1204 is held parallel to the ground (e.g., perpendicular to gravity) the SCM weight is asymmetrically distributed to StC connections under transverse load and tabs 1203 buttressed against the top of array housing 1204 which reduce axial-load on StC connections on the bottom of array housing 1204. When array housing 1204 is held in line with gravity (e.g., parallel to gravity), all StC connections are under transverse load to retain the SCM against array housing 1204. When the array is held at an angle, a combination of loading on the annular snap-fits is experienced.

Hooks can be integrated into the array housing cast from thermoset plastic (e.g., polyolefin) for impact resistance, rigidity, and strength. Overmolded brackets can be injection molded, cast, or additive manufactured from thermoplastic (e.g., polypropylene) for living-hinge flexibility and tab rigidity. Because the hooks and hollows are rigid, the StC joint cannot be flexed or slid undone unless intended.

The cumulative StC connections constrain tab movement to up-and-down translation during installation and removal, producing a robust and immobile joint once installed. Adding hooks increases the holding strength of the joint and vice versa. The relief angle of the hook is dependent upon the hook and overmolded bracket material, tab thickness, and hook shape. Reducing the relief angle increases the contact area in the StC joint, increasing the force to disjoin the StC connection and vice versa. The same principles and criterium apply to the relief slope of the hollow undercut. Consequently, StC connections can be used in circumstances where low mounting profiles and high holding strength are demanded.

Acoustic Coupling Device

The acoustic coupling medium (e.g., SCM) of the disclosed technology can be configured in an acoustic couplant device and operable to conduct acoustic signals between a transducer element disposed in a housing body of the couplant device and a receiving specimen (e.g., skin of a subject) in contact with the acoustic coupling medium to propagate the acoustic signal toward a target volume. The disclosed acoustic coupling medium is capable to conform to the target volume such that there is an acoustic impedance matching (e.g., very low reflection) between the receiving medium and the transducer element.

A. Acoustic Coupling Device Comprising an Elastomer Overmolded Bracket

Figure 13A:
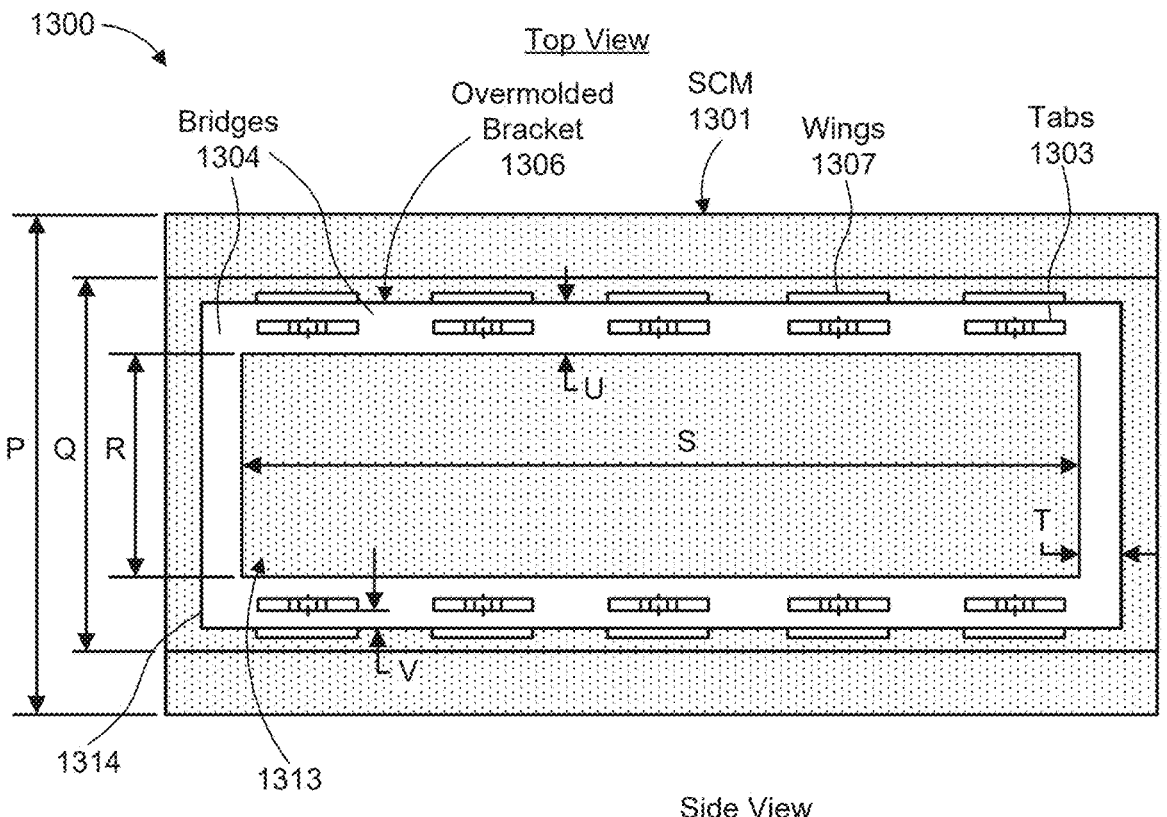
FIGS. 13A and 13B show an exemplary embodiment of an acoustic coupling device comprising an elastomer over-molded bracket of the disclosed technology.
Figure 13A:
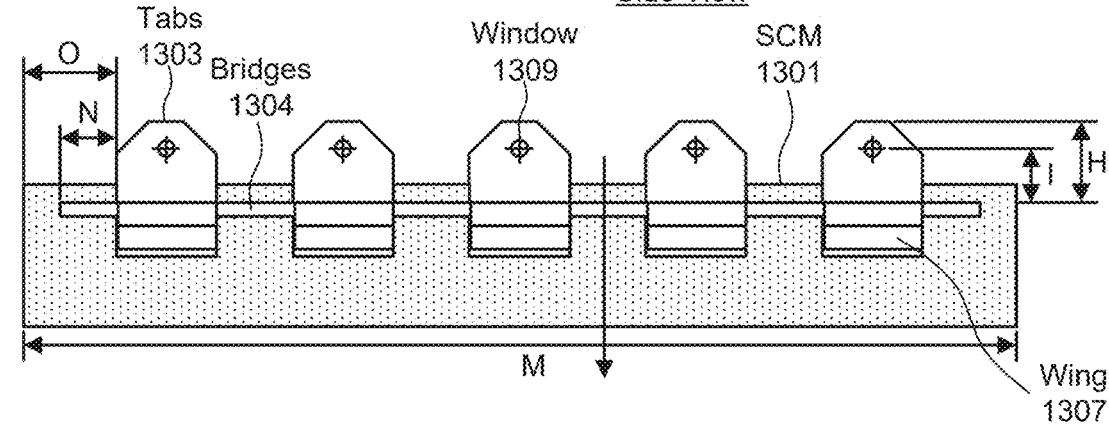
Figure 13A:
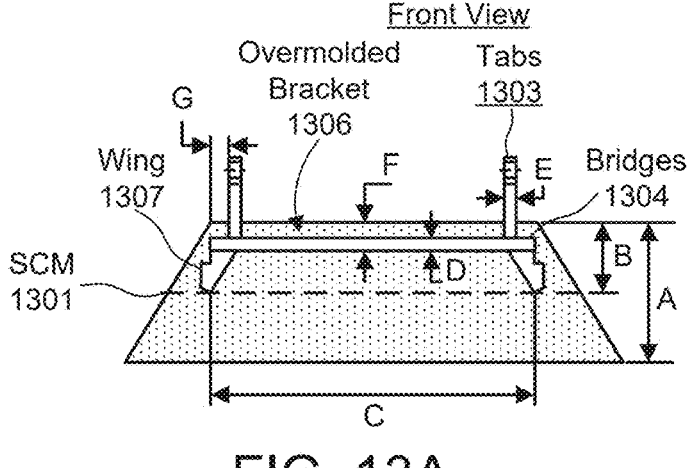
Figure 13B:
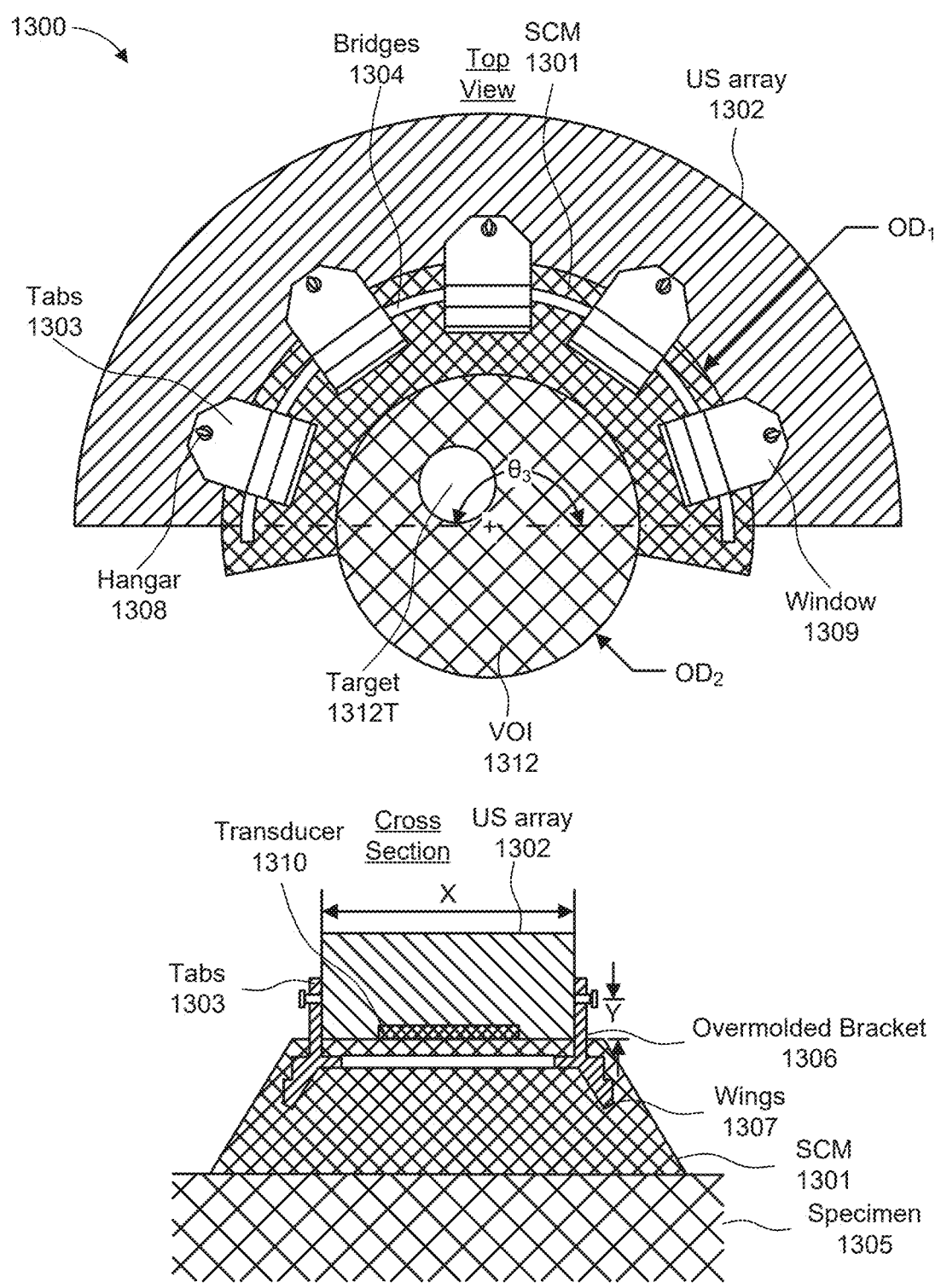
Figure 13C:
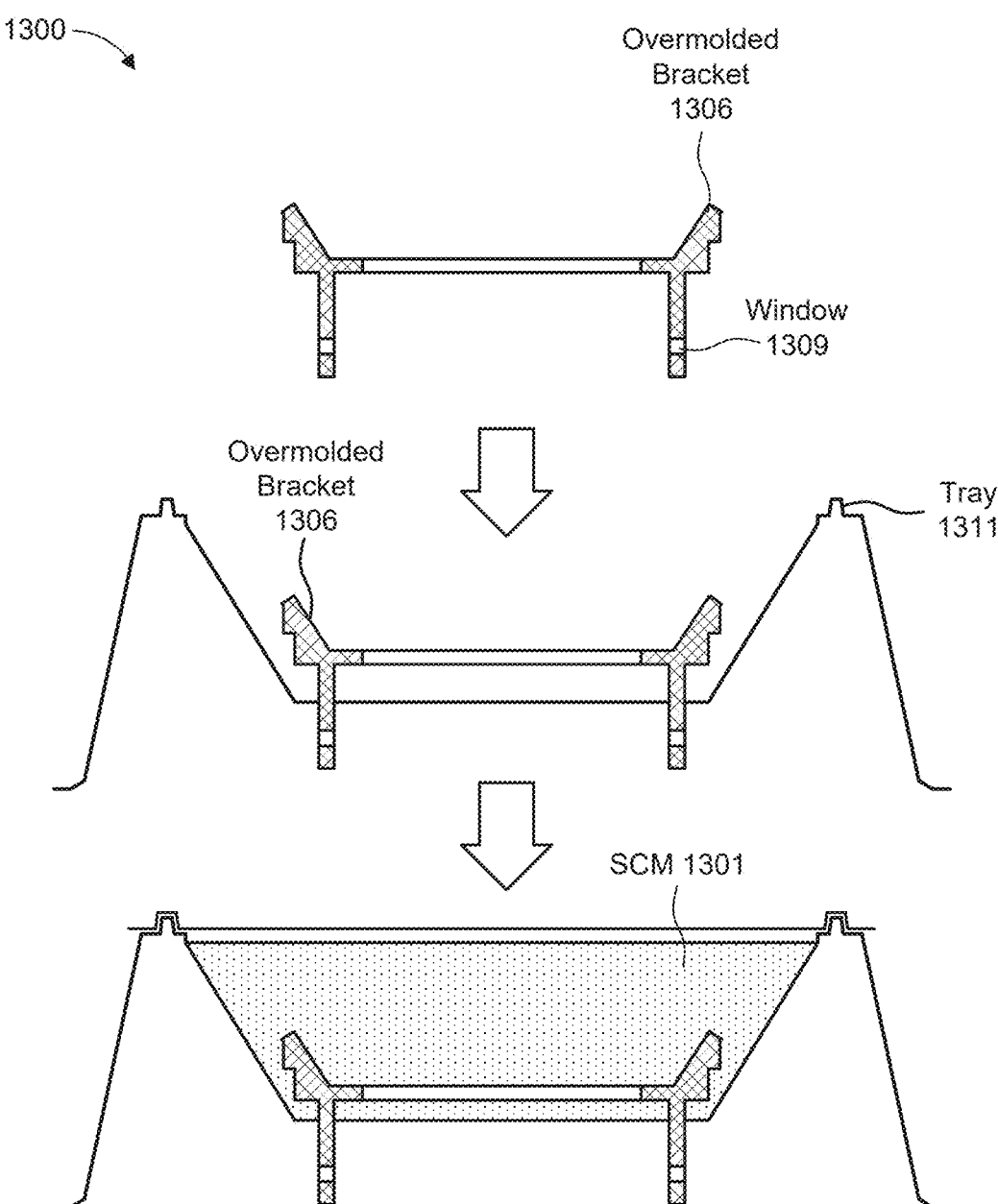
FIG. 13C shows a schematic diagram of a method for preparing an exemplary SCM of the acoustic coupling device of FIGS. 13A and 13B of the disclosed technology.

FIGS. 13A-13C show a schematic diagram of an acoustic coupling device 1300 of the present disclosure comprising a SCM (e.g., hydrogel, or other SCM material) with an imbedded elastomer overmolded bracket (e.g., similar to the overmolded bracket 303 of FIG. 3), with example features and/or characteristics enumerated in Table 8.

TABLE 8

Properties of Exemplary SCM 1301
with Elastomer Overmolded Bracket

| | Poly(Vinyl Alcohol) Hydrogel | Conditions |
|---|---|---|
| SCM | 100% elongation | SATP |
| | 50% compression | SATP |
| | 55 kPa compression modulus | SATP |
| | 55 kPa elastic modulus | — |
| | 1535 m/s speed of sound | 2.25 MHz non-focused center frequency @ SATP |
| | ≤0.16 dB/cm · MHz acoustic attenuation | 2.25 MHz non-focused center frequency @ SATP |
| | 1.13 specific gravity | SATP |
| Bracket | Thermoplastic Poly(Urethane) | — |
| | 1.22 g/cc density | ASTM D792 |
| | 0.18% Moisture Absorption | ASTM D570 24 hrs |
| | 9 MPa Tensile Yield Strength | ASTM D638 |
| | 39 MPa Ultimate Tensile Strength | ASTM D638 |
| | 26 MPa tensile modulus | ASTM D638 |
| | 55% Elongation at Yield | ASTM D638 |
| | 580% Elongation at Break | ASTM D638 |
| | 117.2 m · N/m$^3$ × 10$^6$ | ASTM D638 |

TABLE 8-continued

Properties of Exemplary SCM 1301
with Elastomer Overmolded Bracket

| Poly(Vinyl Alcohol) Hydrogel | Conditions |
|---|---|
| Toughness | |
| 95 Shore-A Hardness | ASTM D2240 |
| 19.1 kJ/m$^2$ Notch Izod Impact Strength | ASTM D256 |
| 0.06 g Abrasion Resistance | ASTM D4060 |
| 220° C. Melting Point | DSC |

Abbreviations: standard temperature and pressure (STP)

FIG. 13A shows a schematic diagram of top view, side view, and front sectional view of an example embodiment of an acoustic coupling device 1300. In the illustrated embodiment, the acoustic coupling device 1300 includes a SCM 1301 and an example embodiment of an overmolded bracket 1306 embedded within the SCM 1301.

The overmolded bracket 1306 includes an embedded frame (embedded within the SCM 1301) having a perimeter 1314 that encompasses an opening 1313. For example, the opening 1313 can be configured to a size larger than the one or more transducers, such that the overmolded bracket 1306 surrounds the acoustic signal transmission field and does not obstruct acoustic signals transmitted and received by the one or more transducer elements of the US array 1302. The perimeter 1314 (and/or the opening 1313) can be shaped in various ways, including but not limited to rectangular, elliptical, or other forms, which can be based on the array of transducer elements to be interfaced with the acoustic coupling device 1300.

The overmolded bracket 1306 includes a plurality of tabs 1303, disposed on the perimeter 1314, which span upward so as to extend away from the embedded portion to outside of the SCM 1301. In some embodiments of the overmolded bracket 1306, there is a single tab structure on each side of the perimeter 1314 to constitute the plurality of tabs 1303; whereas in some embodiments, there are multiple tab structures on a set of opposing sides of the perimeter 1314 to constitute the plurality of tabs 1303 (like that shown in FIG. 13A). In such embodiments of the plurality of tabs 1303 comprising multiple tab structures on the set of opposing sides of the perimeter 1314, the intervening portions of the perimeter 1314 between the multiple tab structures of the plurality of tabs 1303 can be bridges 1304, which interconnect the tabs 1303 to the overmolded bracket 1306 in a manner that provides flexibility and/or bendability of the overmolded bracket 1306. For example, the bridges 1304 allow for the overmolded bracket 1306 to bend when the SCM 1301 is bended, e.g., such as when conformed to a curved array of transducer elements and/or conformed to a curved body structure, such as an abdomen, neck, extremity or other body part of a subject, like Volume of Interest (VOI) 1312 illustrated in FIG. 13B. In some embodiments, for example, the bridges 1304 include a flexible and/or bendable material to provide for the flexibility and/or bendability of the overmolded bracket 1306; and/or, in some embodiments, the bridges 1304 include a pivot joint to provide for the flexibility and/or bendability of the overmolded bracket 1306. The example designs allow for flexibility of the SCM and conformability to a specimen (e.g., skin of a human).

Referring back to FIG. 13A, in some embodiments of the acoustic coupling device 1300, the overmolded bracket 1306 may optionally include a plurality of wings 1307 (also referred to as "winglets") that are connected to the outer perimeter, e.g., on a side and/or on a bottom, to span outward from the perimeter of the overmolded bracket within the SCM 1301. For example, the winglets can provide lateral support against sagging when the SCM is oriented parallel to the ground. In addition, the bracket is flexible prior to installation, becoming fixed rigidly to the array after installation similar to a cable bridge under tension.

Table 9 lists a set of example dimensions of the acoustic coupling device 1300 shown in FIG. 13A.

TABLE 9

Elastomer Overmolded Bracket Dimensions from FIG. 13A

| Dimension ID | Description | Dimension | |
|---|---|---|---|
| A | SCM height | 30.00 | mm |
| B | SCM max compression | 15.00 | mm |
| C | Overmolded bracket inside winglet width | 65.50 | mm |
| D | Frame thickness at end of frame | 3.00 | mm |
| E | Tab thickness | 3.00 | mm |
| F | Frame depth in SCM | 5.00 | mm |
| G | Bracket tab depth | 5.00 | mm |
| H | Tab height | 26.50 | mm |
| I | Tab window height | 11.00 | mm |
| J | Tab width | 30.00 | mm |
| K | Bridge length | 37.70 | mm |
| L | Bridge thickness | 3.00 | mm |
| M | SCM length | 314.16 | mm |
| N | Bracket overhang | 3.10 | mm |
| O | SCM overhang | 8.10 | mm |
| P | SCM width #1 | 76.30 | mm |
| Q | SCM width #2 | 111.00 | mm |
| R | US- Window width | 50.30 | mm |
| S | US- Window length | 276.00 | mm |
| T | Frame Width at end of frame | 4.50 | mm |
| U | Frame Width | 5.00 | mm |
| V | Lip | 4.00 | mm |
| W | Hangar height | 14.00 | mm |
| X | Array width | 60.30 | mm |

FIG. 13B shows a schematic diagram of the acoustic coupling device 1300 configured on a specimen 1305 and including an example embodiment of an elastomer overmolded bracket 1306. In the illustrated embodiment, the acoustic coupling device 1300 comprises a US array 1302 having a half-circle geometry (e.g., 180° Arc) with a large inner diameter (e.g., 200 mm inner diameter (ID)) used to scan patient extremities (e.g., specimen 1305). The specimen 1305 includes a Volume of Interest (VOI) 1312, within which may be a target of interest 1312T, for acoustic interrogation (e.g., imaging). In some embodiments, the acoustic coupling device 1300 includes 20-transducers equally spaced along the US array 1302. The transducer aperture centroids can be coplanar with the mid-plane of the US array 1302. Each transducer can dither the US beam (e.g., 30°) to scan a region of interest, e.g., VOI 1312 of specimen 1305. Several targets of varying dimensions (e.g., 170 mm-146 mm outer diameter (OD)) can couple to the US array 1302 via the SCM 1301. To couple to the specified range of targets, a geometric configuration was developed for both the SCM 1301 and the overmolded bracket 1306 based on the example material specifications listed in Table 8.

In some example embodiments, the acoustic coupling device 1300 includes the bridges 1304 that connect the tabs 1303 together to form the embedded frame on the overmolded bracket 1306, which retains the SCM 1301. In turn, the elastomer frame can be sized to retain the SCM against the array while providing enough room for the US-window such that no acoustic interference occurs. In some example embodiments, the (optional) wings 1307 of the overmolded bracket 1306 and SCM 1301 are tapered outward from the US array 1302 (e.g., ~20 degrees) to enlarge the acoustically coupled scanning area and to also avoid acoustic interference during beam steering. Wings 1307 on the overmolded bracket 1306 also provide rigidity along the tapered sides of the SCM 1301 to prevent the SCM material from sagging when the US array 1302 is held parallel to the ground. The wings 1307 are imbedded just above maximum compression point of the SCM 1301 (e.g., ~50%) and will flex outward as the SCM 1301 compresses. In addition, the wings 1307 can include "staircase" features that include one or more step structures on at least one surface of the wings 1307 to provide resistance to overmolded bracket 1306 from separating from the SCM 1301 during installation and US examinations.

The example overmolded bracket design is capable of securing the SCM 1301 to the array housing 1302 under tension via tabs 1303 attached to a corresponding fastener assembly, e.g., such as a hangar/window fastener. In this manner, for example, the overmolded bracket 1306 easy to install and remove from the array.

FIG. 13C shows a schematic diagram of a process for securing the SCM 1301 to a US array 1302 for manufacturing an example acoustic coupling device 1300. To secure the SCM 1301 to the US array 1302, windows 1309 in the overmolded bracket tabs 1303 click into a US array hanger 1308 (shown in FIG. 13B). When fastened to the array housing 1302, the SCM 1301 between the overmolded bracket frame and the array is compressed (e.g., ~50% strain), generating a spring force (e.g., 27.5 kPa) that pulls the tabs taut under tension, keeping the overmolded bracket 1306 rigidly fixed to the US array 1302.

In some embodiments, the overmolded bracket 1306 is manufactured using filament deposition modeling (FDM) 3D-printing. The overmolded bracket 1306 can be oriented on the build plate to deposit the hot-melt along the length of the frame to maximize the bridge strength. Once printed, the overmolded bracket 1306 is placed into a tray with the tabs inserted down into female grooves in tray 1311. Tabs 1303 compress against the grooves to make a hermetic seal against liquid SCM 1301 from completely encasing the tabs 1303 (e.g., fastening features) used to fasten the SCM 1301 to the US array 1302. In some embodiments, a high impact polystyrene (HIPS) thermoformed tray is used as both the mold and packaging when casting the SCM 1301.

B. Acoustic Coupling Device Comprising a Woven Overmolded Bracket

FIGS. 14A-14D show diagrams of an acoustic coupling device 1400 of the present disclosure comprising a SCM 1401 (e.g., hydrogel, or other SCM material) with an example embodiment of a woven overmolded bracket 1403 (e.g., similar to the overmolded bracket 303 of FIG. 3), with example features and/or characteristics enumerated in Table 10.

The woven overmolded bracket 1403 can be composed of a fibrous material having threads weaved together to form a fabric (e.g., cloth or textile). If unwoven, the cloth is randomly entangled. If woven, the threads are weaved in a manner to optimize strength and flexibility, which can provide requisite structure for the overmolded bracket. For example, weaved fabrics can have anisotropic or isotropic properties depending on the weave pattern.

TABLE 10

| Properties of Exemplary SCM 1400 with Woven Overmolded Bracket | | |
| --- | --- | --- |
| | Poly(Dimethyl Acrylamide) - Sodium Alginate Double Interpenetrating Network Hydrogel (DMA) | Conditions |
| SCM | 1000% elongation | SATP |
| | 100% compression | SATP |
| | 37 kPa compression modulus | SATP |
| | 35 kPa elastic modulus | |
| | 1548 m/s speed of sound | 2.25 MHz non-focused center frequency @ SATP |
| | ≤0.12 dB/cm · MHz acoustic attenuation | 2.25 MHz non-focused center frequency @ SATP |
| | 1.12 specific gravity | SATP |
| Bracket | Plain-Woven Poly(Lactic Acid) | — |
| | 1.43 g/cc density | — |
| | 18 cN/tex (116.15 MPa) tenacity | — |
| | 5% elongation | — |

Abbreviations: standard temperature and pressure (STP)

Figure 14A:
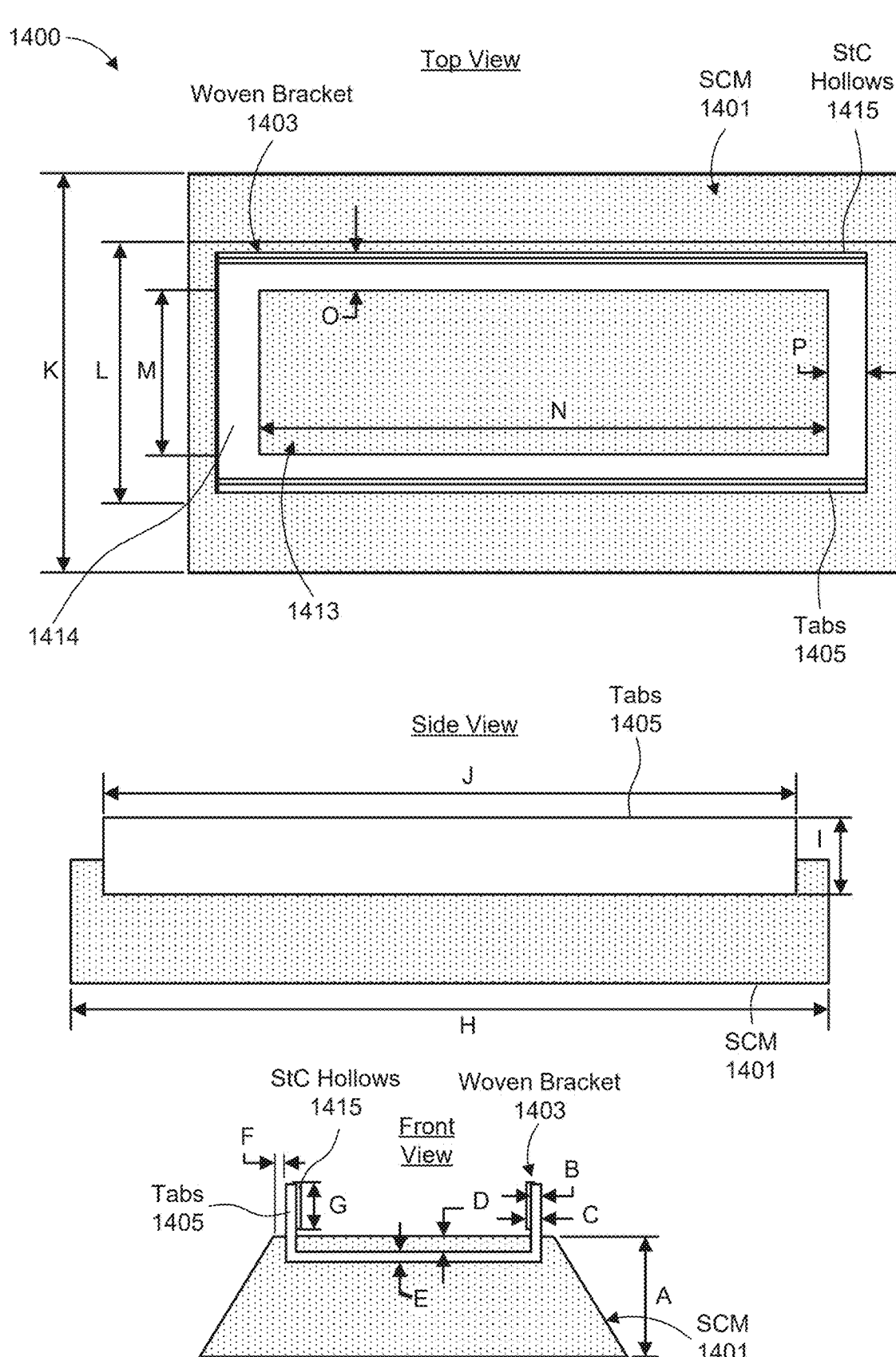
FIGS. 14A and 14B show an exemplary embodiment of an acoustic coupling device comprising woven overmolded bracket of the disclosed technology.

FIG. 14A shows a schematic diagram of top view, side view, and front section views of an example embodiment of an acoustic coupling device 1400. In the illustrated embodiment, the acoustic coupling device 1400 includes a SCM 1401 and an example embodiment of a woven bracket 1403 embedded within the SCM 1401.

The overmolded bracket 1403 includes an embedded portion (embedded within the SCM 1401) having a perimeter 1414 that encompasses an opening 1413. For example, the opening 1413 can be configured to a size larger than the one or more transducers, such that the woven overmolded bracket 1403 surrounds the acoustic signal transmission field and does not obstruct acoustic signals transmitted and received by the one or more transducer elements of the US array 1402. The perimeter 1414 (and/or the opening 1413) can be shaped in various ways, including but not limited to rectangular, elliptical, or other forms, which can be based on the array of transducer elements to be interfaced with the acoustic coupling device 1400.

The woven overmolded bracket 1403 includes a plurality of tabs 1405 disposed, disposed on the perimeter 1414, which span upward so as to extend away from the embedded portion to outside of the SCM 1401. In some embodiments of the woven overmolded bracket 1403, there is a single tab structure on each side of the perimeter to constitute the plurality of tabs 1405; whereas in some embodiments, there are multiple tab structures on each side of the perimeter 1414 to constitute the plurality of tabs 1405 (similar to the tabs configuration shown in FIG. 13A). The structure of the woven overmolded bracket 1403 allows for the overmolded bracket 1403 to bend when the SCM 1401 is bended, e.g., such as when conformed to a curved array of transducer elements and/or conformed to a curved body structure, such as an abdomen, neck, extremity or other body part of a subject, like Volume of Interest (VOI) 1404 illustrated in FIG. 14B. This design allows for flexibility of the SCM and conformability to a specimen (e.g., skin of a human).

The example woven overmolded bracket design is capable of securing the SCM 1401 to the US array 1402 under tension via tabs 1405 attached to a corresponding fastener assembly, e.g., such as a hangar/window fastener. In this manner, for example, the woven overmolded bracket 1403 easy to install and remove from the array. For example, in some embodiments of the acoustic coupling device 1400, the woven overmolded bracket 1403 may optionally include a StC fastener assembly including StC hooks 1407 (spanning off the tabs 1405) and corresponding StC hollows 1415 (e.g., on an interfacing surface of the array housing of the US array 1402). In some example embodiments, like that illustrated in FIG. 14C, the optional StC fastener assembly can include the StC hollows 1415 (e.g., which can be configured as pocket structures spanning off of the tabs 1405), and the StC hooks 1407 can be configured on the US array 1402, e.g., spanning off the interfacing surface of the array housing of the US array 1402. Other example embodiments of fastener 303 can be implemented for the acoustic coupling device 1400. Some examples of the optional StC fastener assembly for the acoustic coupling device 1400 includes the examples discussed in connection with FIGS. 12A-12B. Table 11 lists a set of example dimensions of the acoustic coupling device 1400 shown in FIG. 14A.

TABLE 11

| Woven Overmolded Bracket Dimensions from FIG. 14A | | | |
| --- | --- | --- | --- |
| Dimension ID | Description | Dimension | |
| A | SCM height | 15.00 | mm |
| B | Tab thickness | 2.03 | mm |
| C | Hook + Tab thickness | 4.61 | mm |
| D | Frame depth | 5.00 | mm |
| E | Frame thickness | 2.03 | mm |
| F | Tab depth | 5.00 | mm |
| G | Hook height | 6.35 | mm |
| H | SCM length | 157.10 | mm |
| I | Tab height | 14.00 | mm |
| J | Woven bracket length | 147.10 | mm |
| K | SCM width #1 | 74.40 | mm |
| L | SCM width #2 | 91.70 | mm |
| M | US-window width | 50.30 | mm |
| N | US-window length | 100.00 | mm |
| O | Frame width | 7.03 | mm |
| P | End of frame width | 4.50 | mm |
| Q | Loop Height | 10.50 | mm |
| R | Array width | 60.30 | mm |

Figure 14B:
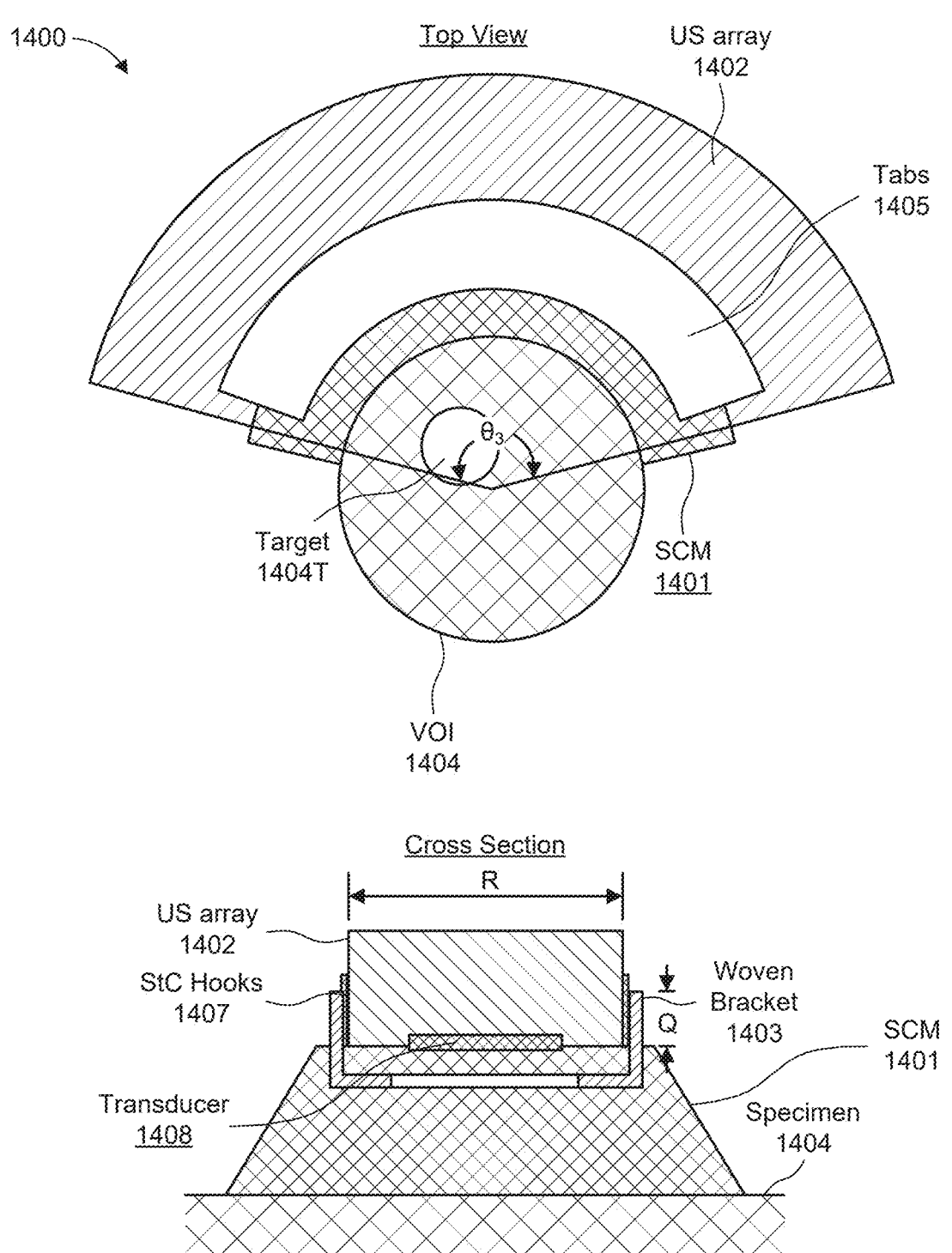

FIG. 14B shows a schematic diagram of the acoustic coupling device 1400 configured to a specimen and including the example woven overmolded bracket 1403. In the illustrated embodiment, the acoustic coupling device 1400 includes the SCM 1401 with an example embodiment of an embedded woven overmolded bracket 1403. In this example, the US array 1402 has a semi-circular geometry (e.g., 120° Arc) with a small inner diameter (e.g., 100 mm ID) used to scan the neck, shoulder regions, and/or joints of a patient (e.g., specimen). The specimen includes a VOI 1404, within which can be a target of interest 1404T, for acoustic interrogation (e.g., imaging). In some embodiments, like in the example shown in FIG. 14B, the acoustic coupling device 1400 includes a plurality (e.g., nine) transducers 1408 (e.g., 11 mm OD) equally spaced along the US array 1402. The transducer aperture centroids can be coplanar with the top-bottom mid-plane of the US array 1402. Each transducer can dither the US beam (e.g., 45°) to scan a region of interest. Several targets of varying dimensions (e.g., 97 mm-85 mm OD) can be coupled to the US array 1402 via the SCM 1401. To couple to the specified range of targets, a geometric configuration was developed for both the SCM and the overmolded bracket based on the example material specifications listed in Table 10.

In some example embodiments, the acoustic coupling device 1400 includes an overmolded bracket die cut from a fibrous weave (e.g., plain-woven poly(lactic acid) (PLA)) to make the tabs and US-window. In some embodiments, for example, the woven overmolded bracket comprises PLA; in some embodiments, for example, the woven overmolded bracket comprises poly(ethylene terephthalate) (PETG). In some example embodiments, the woven overmolded bracket comprises one or more of PLA, PETG, canvas, linen, vinyl, nylon, polyethylene (PE), thermoplastic polyurethane (TPU), polystyrene (PS), high-density polyethylene (HDPE), low-density polyethylene (LDPE), and/or polyvinyl chloride (PVC). Applying heat, pressure, and moisture while bending the edges of the overmolded bracket 1403 forms a permanent crease to make the tabs 1405. In some embodiments, the tabs 1405 fasten the SCM 1401 to the US array 1402 via hooks StC 1407 of the Slide-to-Connect (StC) fastener assembly. In the example embodiment shown in FIG. 14B, an array of StC hollows 1413 is configured on woven overmolded bracket 1403 to affix the tabs 1405 to the StC hooks 1407 on US array 1402. In this embodiment, for example, the StC hollows 1413 are on overmolded bracket 1403 instead of the US array 1402 because the undercuts and female features can trap adventitious materials: a sanitation hazard. When fastened to the US array 1402, the SCM 1401 is under compression (e.g., ~50% strain) and can generate a spring force (e.g., 18.5 kPa) that pulls the tabs taut under tension which keeps the bracket 1403 rigidly fixed to the US array 1402. Non-limiting, example dimensions of the acoustic coupling device 1400 shown in FIG. 14A are enumerated in Table 11.

Figure 14C:
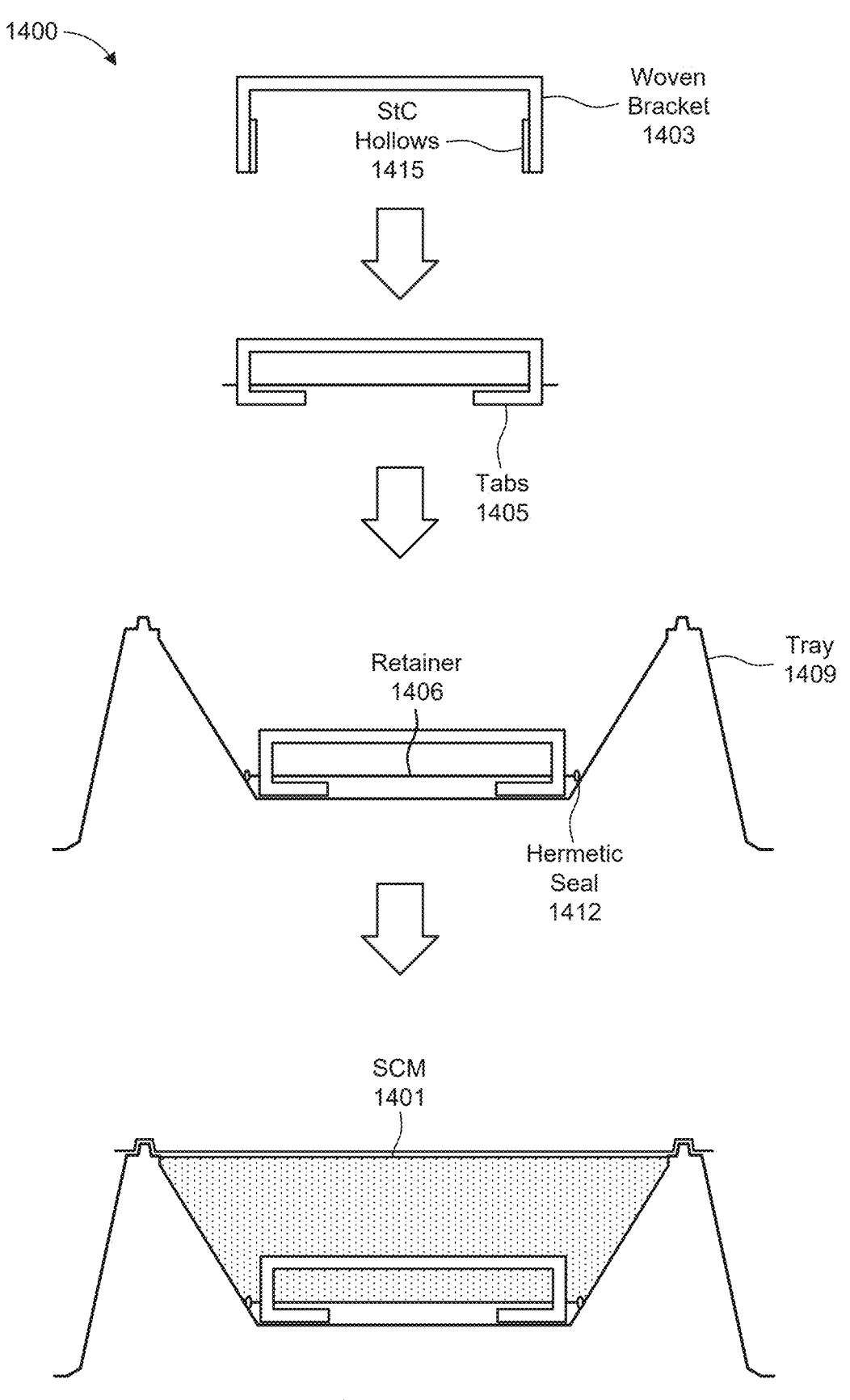
FIGS. 14C and 14D shows a schematic diagram of a method for preparing an exemplary SCM of the acoustic coupling device of FIGS. 14A and 14B of the disclosed technology.
Figure 14D:
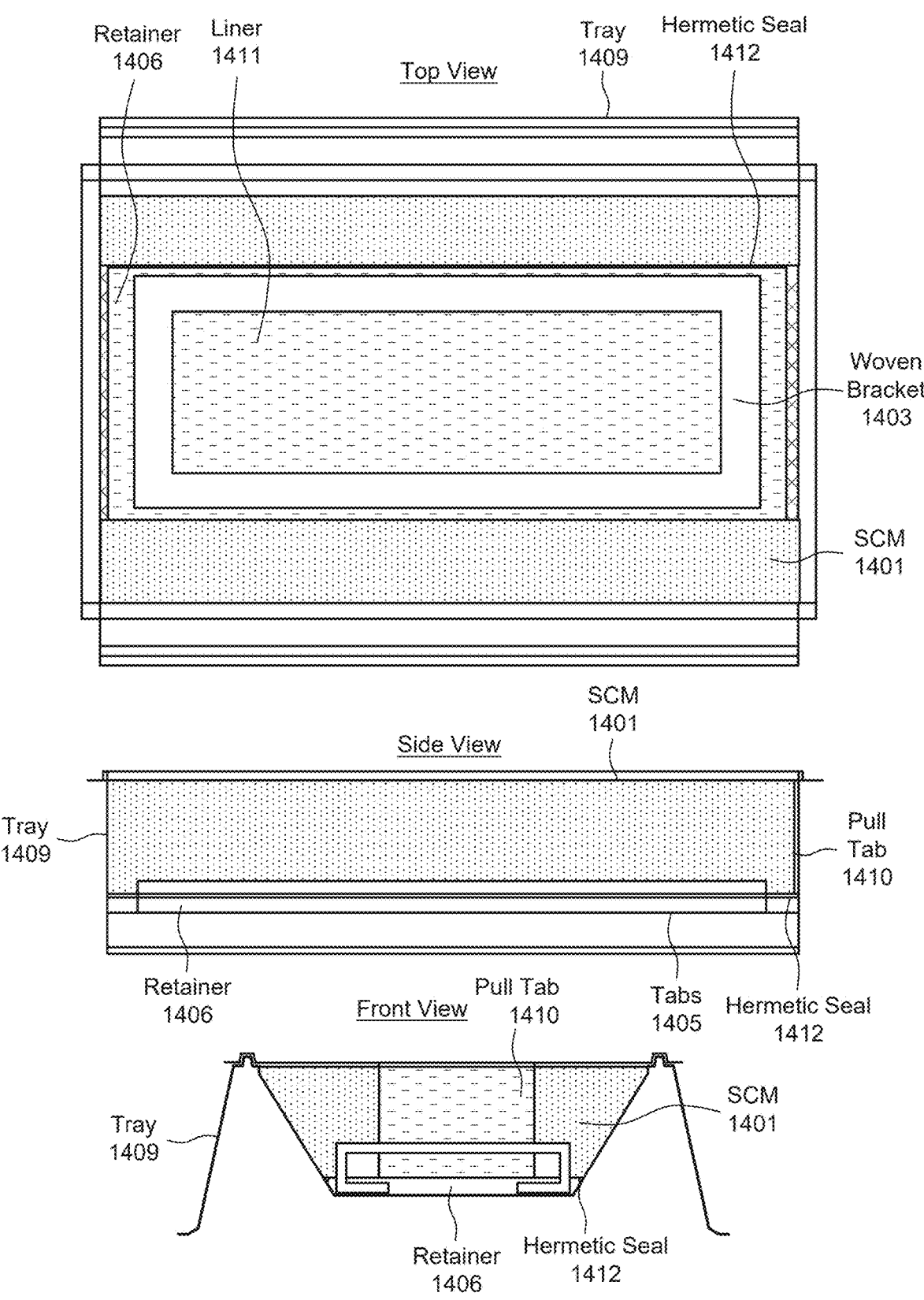

FIGS. 14C and 14D show schematic diagrams of a process for securing the SCM 1401 to a US array 1402 for manufacturing the acoustic coupling device 1400. In some embodiments, the woven overmolded bracket 1403 is manufactured by die cutting the perimeter and US-window, then bending the ends of the material to form tabs 1405. In some embodiments, the woven overmolded bracket 1403 comprises a synthetic PLA plain-woven weave. A synthetic PLA plain-woven weave can provide enhanced characteristics as compared to a non-woven, braided, or knitted PLA weaves as plain-woven weaves absorb less aqueous liquid and are almost completely inelastic when compared to anisotropic, stretchable, loose weave patterns. Also, the isotropic plain-weave rigidity adds dimensional stability to the woven bracket 1403 in contrast to the other weave patterns that collapse when unsupported against gravity after forming the tabs. As such, to preclude free standing features on the woven overmolded bracket 1403 from collapsing during pour-casting, like the joining ends of the window frame, woven overmolded bracket 1403 comprises plain-woven fabric (e.g., synthetic PLA plane-woven weave).

In some embodiments, the methods include gluing, taping, or adhering the tabs 1405 to a thermoformed, PETG retainer 1406 before pour-casting. Retainer 1406 can be used to form a lacuna between tray 1409 and the retainer 1406 to prevent the tabs 1405 imbedding in SCM 1401 during pour-casting. Tabs 1405 are pulled through undersized slits in the retainer 1406 to anchor the overmolded bracket 1403 at the specified frame depth in tray 1409 and act as a plug to prevent gel-sol from filling the lacuna between retainer 1406 and tray 1409. In some embodiments, methods include pulling tabs 1405 through retainer 1406 until the frame is at depth (e.g., dimension D), like the examples specified in Table 11. Retainer 1406 is then inlaid inside a thermoformed PETG tray 1409 and sealed with permanent snap fits, adhesive, or US welding (e.g., hermetic seal 1412) along the perimeter, creating the lacuna beneath retainer 1406, and the negative open cast cavity above retainer 1406. Gel-sol is poured into the mold, submerging the overmolded bracket 1403. Once poured, a foil barrier is rolled onto the gel-sol surface followed by a PETG lid. Finally, the cured SCM

1401 is inspected for air bubbles, fisheyes, and detritus before sending to storage or shipping out.

Perforations running from the edges of plastic retainer 1406 to the slit form an "easy to tear" plastic liner 1411, like that shown in the diagram of FIG. 14D. To remove SCM 1401 from tray 1409, a user can pull the liner tab 1410 (also referred to as "pull tab"). Liner 1411 sticks to the transducer side of the SCM 1401 when pulled out of the tray 1409 to protect the US window from dust and debris and to aid in handling. Once pulled out of the tray 1409, liner 1411 can be removed from the SCM 1401 just prior to fastening the SCM 1401 to the US array 1402, e.g., via the StC fastener assembly.

In some embodiments, the SCM 1401 comprises a hydrogel including DMA. DMA hydrogels are particular suitable for stationary US examinations of musculoskeletal joint anatomy because DMA hydrogels are tacky and highly conformable (e.g., the entire SCM 1401 is sticky). In some embodiments, the methods include applying water to the scanning region prior to conducting the stationary US examination so wet the SCM 1401 comprising DMA. The SCM can then slid over the wetted region several times to push out trapped air before the DMA hydrogel absorbs the water. After the water is absorbed, an airtight, air-free, acoustically coupled seal can formed between the patient's skin and SCM 1401. When SCM 1401 needs to be removed, a wet towel gently dabbing the skin around the SCM can remove the DMA hydrogel from the patient's skin without leaving residue. Additionally, with negligible force, DMA hydrogels can compress up to their entire thickness without bursting, essentially enveloping the target site with the SCM 1401 for excellent, stationary acoustic coupling. This is due in part to the woven bracket almost collapsing on itself completely while the SCM 1401 is compressed up to the US array 1402. As a result, the combination of the SCM tackiness and conformability allows the operator to "stick" onto variegated topographies around the target location to observe the patient's physiology during a static scan.

Some example embodiments of the disclosed acoustic signal transmission couplants may include features and aspects of compositions, articles, and devices for hydrogels and/or method of hydrogel fabricating and/or use in acoustic imaging as described in U.S. Patent Publication No. 2022/0106424A1 and PCT Patent Publication No. WO2020/168087A1) and described in U.S. Patent Publication No. 2022/0134608A1 and PCT Patent Publication No. WO2020/181213A1, the contents of which are incorporated by reference as part of this patent document for all purposes. Some example embodiments of the disclosed acoustic signal transmission couplants can be implemented in acoustic imaging probe devices, methods, and systems as described in APPENDIX C (i.e., U.S. Pat. No. 10,743,838, the content of which is incorporated by reference as part of this patent document for all purposes.

EXAMPLES

The following examples are illustrative of several embodiments of the present technology. Other exemplary embodiments of the present technology may be presented prior to the following listed examples, or after the following listed examples.

In some embodiments in accordance with the present technology (example A1), a couplant device for transmission of acoustic energy between transducers and a target includes an array of transducer elements to transmit acoustic signals toward a target volume and to receive returned acoustic signals that return from at least part of the target volume; a housing body including a curved section on which the array of transducer elements are arranged; an acoustic coupling component including a hydrogel material, the acoustic coupling component operable to conduct the acoustic signals between a transducer element disposed in the housing body and a receiving medium in contact with the acoustic coupling component to propagate the acoustic signals toward the target volume; and a coupling element for compressing the acoustic coupling component including the hydrogel to the array, wherein the acoustic coupling component is capable to conform to the receiving medium and the transducer element such that there is an acoustic impedance matching between the receiving medium and the transducer element.

Example A2 includes the device of any of examples A1-A9, wherein the coupling element includes a bracket that compresses the acoustic coupling component to the array.

Example A3 includes the device of example A2 or any of examples A1-A9, wherein the coupling element further includes a retainer element applied to an external surface of the bracket to compress the acoustic coupling component to the array.

Example A4 includes the device of any of examples A1-A9, wherein the coupling element includes a bracket embedded within the acoustic coupling medium that compresses the acoustic coupling medium to the array.

Example A5 includes the device of example A4 or any of examples A1-A9, wherein the coupling element further includes a fastener applied to the embedded bracket to compress the acoustic coupling component to the array.

Example A6 includes the device of example A4 or any of examples A1-A9, wherein the bracket includes an elastomer.

Example A7 includes the device of example A6 or any of examples A1-A9, wherein the elastomer includes poly(urethane).

Example A8 includes the device of example A4 or any of examples A1-A9, wherein the hydrogel material includes poly(dimethyl acrylamide).

Example A9 includes the device of any of examples A1-A8, wherein the acoustic coupling medium comprises an adhesive material.

In some embodiments in accordance with the present technology (example B1), an acoustic couplant device includes an array of transducer elements arranged in a housing and operable to transmit acoustic signals toward a target volume and to receive returned acoustic signals that return from at least part of the target volume; a housing body including a curved section on which the array of transducer elements are arranged; an acoustic coupling component coupled to the array of transducer elements and including a sonolucent coupling medium (SCM) material, the acoustic coupling component operable to conduct the acoustic signals between each transducer element coupled to the acoustic coupling component and a receiving medium when in contact with the acoustic coupling component to propagate the acoustic signals toward the target volume; and a coupling element attached to one of the acoustic coupling component or the housing of the array of transducer elements and attachable to the other of the acoustic coupling component or the housing to secure the acoustic coupling component to the array of transducer elements.

Example B2 includes the device of any of examples B1-B21, wherein the acoustic coupling component is structured to have a ledge structure at a first end of the acoustic coupling component that is configured to interface with the array of transducer elements, wherein the coupling element includes a retainer element having a recess portion that at least partially surrounds the ledge structure of the acoustic coupling component so as to couple the acoustic coupling component to the array of transducer elements.

Example B3 includes the device of example B2 or any of examples B1-B21, wherein the coupling element further includes a fastener applied to an external surface of the retainer element to couple the coupling element to the housing of the array of transducer elements.

Example B4 includes the device of any of examples B1-B21, wherein the coupling element includes a bracket embedded within the SCM material of the acoustic coupling component.

Example B5 includes the device of example B4 or any of examples B1-B21, wherein the device comprises a coupling assembly including the bracket and a fastener, wherein the fastener is attachable to a portion of the embedded bracket.

Example B6 includes the device of example B5 or any of examples B1-B21, wherein the fastener is reversibly attachable to the portion of the embedded bracket.

Example B7 includes the device of any of examples B2-B6 or any of examples B1-B21, wherein the coupling element is coupled to the acoustic coupling component so as to compress the acoustic coupling component to the array of transducer elements.

Example B8 includes the device of any of examples B4-B7 or any of examples B1-B21, wherein the bracket includes an elastomer material.

Example B9 includes the device of example B8 or any of examples B1-B21, wherein the elastomer includes poly (urethane).

Example B10 includes the device of any of examples B4-B7 or any of examples B1-B21, wherein the SCM material includes at least one of a hydrogel; a ballistics gel; a paraffin gel; a thermoform or thermoset low-clastic modulus TPX elastomer material; a bladder filled with one or more of a mineral oil, water, an aquagel, or a paraffin gel; or a silicone material.

Example B11 includes the device of any of examples B4-B7 or any of examples B1-B21, wherein the bracket includes a weave formed of a fibrous material.

Example B12 includes the device of example B11 or any of examples B1-B21, wherein the fibrous material includes poly(lactic acid).

Example B13 includes the device of any of examples B5-B12 or any of examples B1-B21, wherein the fastener includes at least one of a snap-fit fastener, a window-hangar fastener, a friction-fit fastener, or a touch fastener.

Example B14 includes the device of any of examples B1-B21, wherein the acoustic coupling component includes a tapered body, where a first side of the acoustic coupling component having a first area is coupled to the array of transducer elements, and a second side of the acoustic coupling component having a second area larger than the first area is couplable to the receiving medium.

Example B15 includes the device of any of examples B1-B21, wherein the acoustic coupling component comprises an adhesive material.

Example B16 includes the device of example B15 or any of examples B1-B21, wherein the adhesive material is an adhesive layer attached to a body of the SCM material at an exterior surface of the acoustic coupling component.

Example B17 includes the device of example B16 or any of examples B1-B21, wherein the adhesive material includes a low elastic modulus polymer operable to adhere to the array of transducer elements by wetting an outer surface of the transducer elements and attaching the acoustic coupling component to the transducer elements.

Example B18 includes the device of example B16 or any of examples B1-B21, wherein the acoustic coupling component is able to be moved along a surface of the receiving medium while being statically fixed to the array of transducer elements based on adhesion of the adhesive layer to the array of transducer elements.

Example B19 includes the device of example B15 or any of examples B1-B21, wherein the adhesive material is integrated in a body of the SCM material to provide an adhesive external surface uniformly along an outer surface of the acoustic coupling component.

Example B20 includes the device of example B19 or any of examples B1-B21, wherein the acoustic coupling component is configured to spatially fix the array of transducer elements to the receiving medium to prohibit relative movement between the array of transducer elements and the receiving medium.

Example B21 includes the device of any of examples B1-B20, wherein the acoustic coupling component is capable to couple to the receiving medium so as to morphologically conform to both the receiving medium and one or more transducer elements of the array such that there is an acoustic impedance matching between the receiving medium and the transducer element.

In some embodiments in accordance with the present technology (example B22), an acoustic couplant device includes an acoustic coupling component including a sonolucent coupling medium (SCM) material, the acoustic coupling component operable to conform to one or more transducer elements of an array of transducer elements and conduct acoustic signals between the one or more transducer elements and a receiving medium when the acoustic coupling component is in contact with the receiving medium to propagate the acoustic signals toward a target volume; and a coupling assembly to attach the acoustic coupling component to a housing of the array of transducer elements, the coupling assembly comprising: a bracket having a first portion at least partially embedded within the SCM material of the acoustic coupling component and a second portion at least partially extending out of the acoustic coupling component, and a fastener coupled to at least the second portion of the bracket and configured to attach the second portion of the bracket to the housing.

Example B23 includes the device of any of examples B22-B49, wherein the fastener is reversibly attachable to the second portion of the bracket.

Example B24 includes the device of any of examples B22-B23 or any of examples B22-B49, wherein the coupling assembly is operable to attach the acoustic coupling component to the housing so as to compress the acoustic coupling component to the one or more transducer elements of the array.

Example B25 includes the device of any of examples B22-B24 or any of examples B22-B49, wherein the bracket includes an embedded frame having a perimeter that encompasses an opening, and a plurality of tabs disposed on the embedded frame that extend away from the perimeter and outward of the of the acoustic coupling component.

Example B26 includes the device of example B25 or any of examples B22-B49, wherein the opening is configured to have a size larger than the one or more transducer elements of the array of transducer elements.

Example B27 includes the device of example B25 or any of examples B22-B49, wherein the plurality of tabs comprises a first set of tabs and a second set of tabs disposed on opposing sides of the perimeter of the embedded frame.

Example B28 includes the device of example B27 or any of examples B22-B49, wherein intervening portions of the perimeter between the first set of tabs and the second set of tabs provides flexibility and/or bendability of the acoustic coupling device to conform to a geometry of the array of transducer elements.

Example B29 includes the device of example B28 or any of examples B22-B49, wherein the geometry of the array of transducer elements includes a curved geometry.

Example B30 includes the device of example B25 or any of examples B22-B49, wherein the plurality of tabs comprises a first tab and a second tab disposed on opposing sides of the perimeter of the embedded frame.

Example B31 includes the device of example B25 or any of examples B22-B49, wherein the bracket further includes a plurality of wings connected to an outer surface of the perimeter that span outward and/or laterally within the SCM material.

Example B32 includes the device of example B31 or any of examples B22-B49, wherein the plurality of wings includes one or more step structures on at least one surface of the wings that provide resistance for the bracket from separating from the SCM material.

Example B33 includes the device of any of examples B22-B32 or any of examples B22-B49, wherein the bracket includes an elastomer material.

Example B34 includes the device of example B33 or any of examples B22-B49, wherein the elastomer includes poly (urethane).

Example B35 includes the device of any of examples B22-B24 or any of examples B22-B49, wherein the bracket includes a woven bracket comprising a fibrous material having threads weaved together.

Example B36 includes the device of example B35 or any of examples B22-B49, wherein the woven bracket includes an embedded frame portion having a perimeter that encompasses an opening, and a plurality of tabs disposed on the embedded frame portion that extend away from the perimeter and outward of the of the acoustic coupling component.

Example B37 includes the device of example B36 or any of examples B22-B49, wherein the opening is configured to have a size larger than the one or more transducer elements of the array of transducer elements.

Example B38 includes the device of example B36 or any of examples B22-B49, wherein the plurality of tabs comprises a first set of multiple tab structures and a second set of multiple tab structures disposed on opposing sides of the perimeter of the embedded frame portion.

Example B39 includes the device of example B36 or any of examples B22-B49, wherein the plurality of tabs comprises a first single tab and a second single tab disposed on opposing sides of the perimeter of the embedded frame portion.

Example B40 includes the device of example B36 or any of examples B22-B49, wherein the plurality of tabs includes at least one hole or at least one protrusion structure configured to interact with a corresponding structure of the fastener.

Example B41 includes the device of any of examples B35-B40 or any of examples B22-B49, wherein the fibrous material includes at least one of poly(lactic acid) (PLA) or poly(ethylene terephthalate) (PETG).

Example B42 includes the device of any of examples B35-B40 or any of examples B22-B49, wherein the fibrous material includes one or more of PLA, PETG, canvas, linen, vinyl, nylon, polyethylene (PE), thermoplastic polyurethane (TPU), polystyrene (PS), high-density polyethylene (HDPE), low-density polyethylene (LDPE), and/or polyvinyl chloride (PVC).

Example B43 includes the device of any of examples B22-B42 or any of examples B22-B49, wherein the fastener includes at least one of a snap-fit fastener, a window-hangar fastener, a friction-fit fastener, or a touch fastener.

Example B44 includes the device of any of examples B22-B43 or any of examples B22-B49, wherein the SCM material includes at least one of a hydrogel; a ballistics gel; a paraffin gel; a thermoform or thermoset low-elastic modulus TPX elastomer material; a bladder filled with one or more of a mineral oil, water, an aquagel, or a paraffin gel; or a silicone material.

Example B45 includes the device of example B44 or any of examples B22-B49, wherein the hydrogel includes at least one of poly(dimethyl acrylamide) (PDMA) or sodium alginate (SA).

Example B46 includes the device of any of examples B22-B45 or any of examples B22-B49, wherein the acoustic coupling component includes a tapered body, where a first side of the acoustic coupling component having a first area is coupled to the array of transducer elements, and a second side of the acoustic coupling component having a second area larger than the first area is couplable to the receiving medium.

Example B47 includes the device of any of examples B22-B46 or any of examples B22-B49, wherein the acoustic coupling component comprises an adhesive material.

Example B48 includes the device of example B47 or any of examples B22-B49, wherein the adhesive material is an adhesive layer attached to a body of the hydrogel material at an exterior surface of the acoustic coupling component.

Example B49 includes the device of any of examples B22-B48, wherein the acoustic coupling component is capable to couple to the receiving medium so as to morphologically conform to both the receiving medium and one or more transducer elements of the array such that there is an acoustic impedance matching between the receiving medium and the transducer element.

As noted earlier, some of the disclosed embodiments relate to an acoustic coupling medium including a hydrogel formed from one or more polymerizable materials and capable of conforming or molding into specific three-dimensional shapes for use in tomographic ultrasound imaging, large aperture ultrasound imaging, and therapeutic ultrasound.

Hydrogel materials contain mostly water; thus, the acoustic wave speed of the hydrogel is dominated by water. The acoustic wave speed in water is approximately proportional to temperature through a high order empirically determined polynomial relationship from 0 to 100° C. The acoustic wave speed of pure water varies from 1482 m/s to 1524 m/s from 20° C. to 37° C., respectively. Thus, the acoustic wave speed in a polymeric material will vary with temperature.

A material with a calibrated acoustic wave speed may be used in combination with a delay-and-sum beamformer to correct the propagation times on transmission and reception in order to reduce image distortion created by uncalibrated coupling materials. For example, the location of a structure such as a tissue-bone interface is ambiguous without knowledge of the average acoustic wave speed between the array and the bone. The true location of the bone may be deeper or shallower than it measures on the ultrasound image.

A material with a temperature calibrated acoustic wave speed such that the material may be heated in order to provide a more comfortable interface to the patient without creating image distortion. Besides patient comfort, a heated material also supports increased blood flow in the region in contact with the patient and in regions peripheral to the region in contact, thus facilitating more accurate Doppler measurements. A material with a calibrated acoustic wave speed will also function optimally at a target temperature (e.g. 37° C.) or target range of temperatures (e.g. 20-37° C.).

Thermocouples, thermistors, fiber-optic thermometers, or other temperature sensing devices may be implanted into the hydrogel to provide real-time temperature feedback. Additionally, wires, resistors, thermopiles, electrical current, infrared radiation, water pipes, conduction, or other means to heat the hydrogel may be utilized to heat the gel. A temperature feedback and control device may be utilized to control the temperature of the hydrogel precisely and accurately.

The disclosed acoustic coupling medium can be employed in acoustic imaging, range-Doppler measurement, and therapeutic systems to transfer emitted and returned acoustic waveforms between such acoustic systems and a receiving medium, such as tissue of a living organism.

In some implementations of the disclosed acoustic coupling technology, for example, a hydrogel acoustic coupling medium of the present technology can provide spatially-varying acoustic absorption for use with acoustic imaging, diagnostic and/or therapeutic devices or systems to provide tomographic ultrasound imaging, large aperture ultrasound imaging arrays, and therapeutic ultrasound arrays for such acoustic devices and systems. In some implementations of the disclosed technology, the hydrogel acoustic coupling medium can couple acoustic waves from acoustic energy sources into the hydrogel acoustic coupling medium and subsequently into secondary media with acoustic sound speeds ranging from 1400 m/s up to 1700 m/s. Examples of the secondary media include, but are not limited to, mammalian tissues and water. The secondary media may contain structures with sound speeds outside the sound speed range of the coupling medium, e.g., such as bone, implanted devices, plastics, ceramics, glass, and metals.

In practical applications of ultrasound imaging, particularly for imaging human and nonhuman animals, ultrasound image formation typically occurs in the near field of an acoustic emission aperture, which poses several challenges for obtaining high resolution and quality ultrasound images. For example, in such ultrasound imaging applications, generally, one or more transducer elements are included in an acoustic imaging device, forming an array, to generate the acoustic aperture. These transducer elements typically require several wavelengths to transition from the near field to the far field regime following an acoustic emission, thus requiring an acoustic buffer region, also known as an acoustic standoff. For example, this acoustic buffer region or acoustic standoff may be necessary for image formation close to the acoustic aperture. Furthermore, focused image formation typically requires that the ratio of the focal depth divided by the aperture size (e.g., also known as the f-number) be greater than one, e.g., for points of the image formation closest to the acoustic aperture. Likewise, the acoustic standoff is necessary for image formation close to the acoustic aperture in order to satisfy the f-number condition.

In implementations of the disclosed technology, the image formation is generated using combinations of the transducer elements, in which a selected group of transducer elements are used to produce an acoustic emission followed by reception of return acoustic echoes on some, the same, and/or other transducer elements of the group. For example, the transducer elements producing the acoustic emission are referred to as transmit elements. Likewise, the transducer elements that receive the return acoustic echoes are referred to as receive elements. In some examples, the combinations may be divided into combinations of individual pairs of transmit and receive elements such that the linear combination of the pairs produces an approximately equivalent image as obtained using the combinations of one or more elements on both transmit and receive. For example, each time sample of an echo recorded from the pair of transmit and receive elements is an integration of acoustic reflectivity over the corresponding round-trip time or time delay corresponding to the time sample. The integration is a line integral over linear paths of the constant round-trip time or time delay. The linear paths can be circular or elliptical as determined by the location of the pair of transmit and receive elements. In practice, for example, the circular or elliptical paths may extend to highly reflective interfaces including, but not limited to, the interface between the acoustic coupling medium and a low acoustic impedance material, e.g., such as air or plastic, or the interface between the acoustic coupling medium and a high acoustic impedance material, e.g., such as metal or ceramic.

Acoustic reflections from the interfaces, also known as specular reflections, contaminate the line integrals of reflectivity and the corresponding echo samples obtained from the transmit and receive combinations. In general, for the acoustic reflections observed for the combination of transmit and receive elements, the angle of incidence measured from the transmit element to a point on the reflective interface to the surface normal vector for a point lying on the reflective interface equals the angle of reflection measured from the same normal vector to the vector defined by the point on reflective interface to the receive element. The acoustic reflection can have mirror or amphicheiral symmetry. The acoustic reflection has power equal to the acoustic impedance of the secondary medium minus the acoustic impedance of the coupling medium, divided by the acoustic impedance of the secondary medium plus the acoustic impedance of the coupling medium, as described in Equation (1).

$$P_r = \frac{(Z_{2m} - Z_{cm})}{(Z_{2m} + Z_{cm})} \qquad (1)$$

The contamination caused by the acoustic reflection can preclude the use of the transmit and receive combinations in beamformers based on delayed and summed echo samples, also known as a delay-and-sum beamformer. Such preclusion of echo samples can result in removal of the transmit and receive combination from the delay-and-sum beamformer, thus limiting the quality of the image pixel corresponding to the delay-and-sum beamformer. The image pixel quality is a function of the point-spread-function of the limited set of transmit and receive combinations. Such preclusion of echo samples can also reduce the signal-to-noise ratio (SNR) for the image pixel. Additionally, for the apertures with an array pitch greater than one-half wavelength, the image pixel locations that require transmitter and receiver combinations to steer away from zero degrees (0°) will be increasingly subject to grating lobes with increasing steering angle and increasing array pitch. Such grating lobes add to the sensitivity and complexity of the specular reflections.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. An acoustic couplant device, comprising:
an acoustic coupling component including a sonolucent coupling medium (SCM) material, the acoustic coupling component operable to conform to one or more transducer elements of an array of transducer elements and conduct acoustic signals between the one or more transducer elements and a receiving medium when the acoustic coupling component is in contact with the receiving medium to propagate the acoustic signals toward a target volume; and
a coupling assembly to attach the acoustic coupling component to a housing of the array of transducer elements, the coupling assembly comprising:
a bracket having a frame at least partially embedded within the SCM material of the acoustic coupling component, and a plurality of tabs at least partially extending out of the acoustic coupling component, and
a fastener coupled to at least the plurality of tabs and configured to attach the bracket to the housing,
wherein the frame of the bracket includes an opening and has a perimeter that encompasses the opening,
wherein the plurality of tabs comprises a first tab and a second tab or a first set of tabs and a second set of tabs disposed on opposing sides of the perimeter of the frame.

2. The device of claim 1, wherein the coupling assembly is operable to attach the acoustic coupling component to the housing so as to compress the acoustic coupling component to the one or more transducer elements of the array.

3. The device of claim 1, wherein:
the opening of the frame of the bracket is configured to have a size larger than at least one transducer element of the array of transducer elements.

4. The device of claim 1, wherein the bracket further includes a plurality of wings connected to the frame that spans outward and/or laterally within the SCM material, wherein the plurality of wings includes one or more step structures on at least one surface of the wings that provide resistance for the bracket from separating from the SCM material.

5. The device of claim 1, wherein the fastener is reversibly attachable to the plurality of tabs of the bracket.

6. The device of claim 1, wherein the bracket includes an elastomer material.

7. The device of claim 6, wherein the elastomer includes poly(urethane).

8. The device of claim 1, wherein the fastener includes at least one of a snap-fit fastener, a window-hangar fastener, a friction-fit fastener, or a touch fastener.

9. The device of claim 1, wherein the SCM material includes at least one of a hydrogel; a ballistics gel; a paraffin gel; a thermoform or thermoset low-elastic modulus TPX elastomer material; a bladder filled with one or more of a mineral oil, water, an aquagel, or a paraffin gel; or a silicone material.

10. The device of claim 9, wherein the hydrogel includes at least one of poly(dimethyl acrylamide) (PDMA) or sodium alginate (SA).

11. The device of claim 1, wherein the acoustic coupling component includes a tapered body, where a first side of the acoustic coupling component having a first area is coupled to the array of transducer elements, and a second side of the acoustic coupling component having a second area larger than the first area is couplable to the receiving medium.

12. The device of claim 1, wherein the acoustic coupling component comprises an adhesive material.

13. The device of claim 12, wherein the adhesive material is an adhesive layer attached to a body of the SCM material at an exterior surface of the acoustic coupling component.

14. The device of claim 1, wherein the acoustic coupling component is capable to couple to the receiving medium so as to morphologically conform to both the receiving medium and the one or more transducer elements of the array such that there is an acoustic impedance matching between the receiving medium and the one or more transducer elements.

15. An acoustic couplant device, comprising:

an acoustic coupling component including a sonolucent coupling medium (SCM) material, the acoustic coupling component operable to conform to one or more transducer elements of an array of transducer elements and conduct acoustic signals between the one or more transducer elements and a receiving medium when the acoustic coupling component is in contact with the receiving medium to propagate the acoustic signals toward a target volume; and a coupling assembly to attach the acoustic coupling component to a housing of the array of transducer elements, the coupling assembly comprising:

a bracket including a frame at least partially embedded within the SCM material of the acoustic coupling component, a plurality of tabs at least partially extending out of the acoustic coupling component, and a plurality of wings connected to the frame that spans outward and/or laterally within the SCM material, wherein the plurality of wings includes one or more step structures on at least one surface of the wings that provide resistance for the bracket from separating from the SCM material, and a fastener coupled to at least the plurality of tabs and configured to attach the bracket to the housing, wherein the frame of the bracket includes an opening and has a perimeter that encompasses the opening.

16. The device of claim 15, wherein the plurality of tabs comprises a first tab and a second tab or a first set of tabs and a second set of tabs disposed on opposing sides of the perimeter of the frame.

17. The device of claim 15, wherein the coupling assembly is operable to attach the acoustic coupling component to the housing so as to compress the acoustic coupling component to the one or more transducer elements of the array.

18. The device of claim 15, wherein the opening of the frame of the bracket is configured to have a size larger than at least one transducer element of the array of transducer elements.

19. The device of claim 15, wherein the fastener is reversibly attachable to the plurality of tabs of the bracket.

20. The device of claim 15, wherein the acoustic coupling component includes a tapered body, where a first side of the acoustic coupling component having a first area is coupled to the array of transducer elements, and a second side of the acoustic coupling component having a second area larger than the first area is couplable to the receiving medium.

* * * * *